(12) United States Patent
Nomura et al.

(10) Patent No.: US 8,278,650 B2
(45) Date of Patent: Oct. 2, 2012

(54) ORGANIC SEMICONDUCTOR, PHOTOELECTRIC CONVERSION ELEMENT AND IMAGE DEVICE

(75) Inventors: Kimiatsu Nomura, Kanagawa (JP); Tetsuro Mitsui, Kanagawa (JP); Hideyuki Suzuki, Kanagawa (JP); Rui Shen, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 228 days.

(21) Appl. No.: 12/465,727

(22) Filed: May 14, 2009

(65) Prior Publication Data
US 2009/0283758 A1 Nov. 19, 2009

(30) Foreign Application Priority Data

May 14, 2008 (JP) .................................. 2008-127591

(51) Int. Cl.
*H01L 35/24* (2006.01)
(52) U.S. Cl. ................. 257/40; 257/37; 257/38; 257/39; 257/431; 257/E51.026; 257/291
(58) Field of Classification Search ............. 257/40, 257/431, E51.026
See application file for complete search history.

(56) References Cited

U.S. PATENT DOCUMENTS

| 4,256,819 A | 3/1981 | Webster |
| 5,965,875 A | 10/1999 | Merrill |
| 7,129,466 B2 | 10/2006 | Iwasaki |
| 2003/0209651 A1 | 11/2003 | Iwasaki |
| 2007/0290195 A1* | 12/2007 | Forrest .............................. 257/40 |
| 2008/0035965 A1* | 2/2008 | Hayashi et al. ................ 257/291 |

FOREIGN PATENT DOCUMENTS

| JP | 54-024025 A | 2/1979 |
| JP | 2003-332551 A | 11/2003 |
| JP | 2006-086160 A | 3/2006 |
| JP | 2006-100502 A | 4/2006 |

OTHER PUBLICATIONS

Dolotov et al, Photochromism of indoline spiropyrans of the coumarin series in polymeric matrices, Russian Chemical Bulletin, International Edition, vol. 56, No. 5, pp. 904-909, May 2007.*

* cited by examiner

*Primary Examiner* — Mamadou Diallo
(74) *Attorney, Agent, or Firm* — Sughrue Mion, PLLC

(57) ABSTRACT

An organic semiconductor includes: a compound represented by formula (I):

Formula (I):

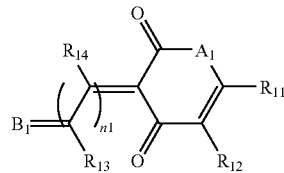

wherein $A_1$ represents O, S or N—$R_{15}$; each of $R_{11}$, $R_{12}$, $R_{13}$, $R_{14}$ and $R_{15}$ independently represents a hydrogen atom or a substituent W as defined in the specification, $R_{11}$ and $R_{12}$ may be linked to form a ring; $B_1$ represents a ring structure containing at least one nitrogen atom; and n1 represents an integer of 0 to 2.

8 Claims, 14 Drawing Sheets

ORGANIC SEMICONDUCTOR, PHOTOELECTRIC CONVERSION ELEMENT AND IMAGE DEVICE

BACKGROUND OF THE INVENTION

1. Field of the Invention

The present invention relates to an organic semiconductor, a photoelectric conversion element, a solid-state image device in which an organic photoelectric conversion part is preferably formed on an electric charge accumulation/transfer/readout substrate, and a compound useful for the organic semiconductor.

2. Description of the Related Art

Conventional visible light sensors in general are a device fabricated by forming a photoelectric conversion site through, for example, formation of PN junction in a semiconductor such as Si. As for the solid-state image device, there is widely used a flat light-receiving device where photoelectric conversion sites are two-dimensionally arrayed in a semiconductor to form pixels and signals generated by photoelectric conversion in each pixel are charge-transferred and read out according to a CCD or CMOS format. The method for realizing a color solid-state image device is generally fabrication of a structure where on the light incident surface side of the flat image-receiving device, a color filter transmitting only light at a specific wavelength is disposed for color separation. In particular, a single-plate sensor in which color filters transmitting blue light, green light and red light, respectively, are regularly disposed on each of two-dimensionally arrayed pixels is well known as a system widely used at present in a digital camera and the like.

In this system, since the color filter transmits only light at a limited wavelength, untransmitted light is not utilized and the light utilization efficiency is bad. Also, in recent years, with the continuing progress toward fabrication of a multipixel device, the pixel size and in turn, the area of a photodiode part become small and this brings about problems of reduction in the aperture ratio and reduction in the light collection efficiency.

In order to solve these problems, there may be considered a system where photoelectric conversion parts capable of detecting light at different wavelengths are vertically stacked. As regards such a system, for example, U.S. Pat. No. 5,965,875 discloses a sensor utilizing wavelength dependency of the absorption coefficient of Si, where a vertically stacked structure is formed and the colors are separated by the difference in the depth, and JP-A-2003-332551 (the term "JP-A" as used herein means an "unexamined published Japanese patent application") discloses a sensor having a stacked structure using an organic photoelectric conversion layer. However, the system utilizing the difference in the depth direction of Si is originally disadvantageous in that the color separation is poor, because the absorption range is overlapped among respective portions and the spectroscopic characteristics are bad. As for other methods to solve the problems, a structure where a photoelectric conversion film of amorphous silicon or an organic photoelectric conversion film is formed on a signal reading substrate is known as a technique for raising the aperture ratio.

Heretofore, several examples have been known for a photoelectric conversion element, an image device and a photosensor each using an organic photoelectric conversion film. It is a task in particular to achieve high photoelectric conversion efficiency and low dark current, and as to the improvement method in this respect, there are disclosed, for example, introduction of a pn-junction or introduction of a bulk-heterostructure for the former and introduction of a blocking layer for the latter.

These structural improvements have a large effect but the characteristics of the material used also greatly contribute to the device performance, which is referred to, for example, in JP-A-2006-086160 and JP-A-2006-100502. The material structure is not only one of main factors for the photoelectric conversion efficiency (exciton dissociation efficiency, charge transport property) and dark current (e.g., amount of dark time carrier) but also a governing factor for the signal responsivity, though this is scarcely mentioned in past reports. In use as a solid-state image device, all of high photoelectric conversion efficiency, low dark current and high response speed need to be satisfied, but it has not been heretofore specifically disclosed what an organic photoelectric conversion material or a device structure satisfies this requirement.

Also, JP-A-54-024025 describes use of a 2,4-chromandione derivative as an electrically photosensitive colorant for use in an electrophoretic migration imaging process, but use of the compound for an organic photoelectric conversion film is not described.

SUMMARY OF THE INVENTION

An object of the present invention is to provide an organic semiconductor composed of a novel thin film, a photoelectric conversion element containing the organic semiconductor and exhibiting high photoelectric conversion efficiency, low dark current and high-speed response, a solid-state image device containing the photoelectric conversion element, and a compound useful for the organic semiconductor.

The above-described object can be attained by the following means.

(1) An organic semiconductor, comprising:
a compound represented by formula (I):

Formula (I):

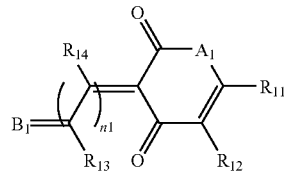

wherein $A_1$ represents O, S or N—$R_{15}$;

each of $R_{11}$, $R_{12}$, $R_{13}$, $R_{14}$ and $R_{15}$ independently represents a hydrogen atom or a substituent W selected from the group consisting of a halogen atom, an alkyl group, an alkenyl group, an alkynyl group, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$) and a sulfato group (—OSO$_3$H), $R_{11}$ and $R_{12}$ may be linked to form a ring;

$B_1$ represents a ring structure containing at least one nitrogen atom; and n1 represents an integer of 0 to 2.

(2) The organic semiconductor as described in (1) above, wherein in formula (I), n1 is 1.

(3) The organic semiconductor as described in (1) or (2) above, wherein in formula (I), each of $R_{13}$ and $R_{14}$ is a hydrogen atom.

(4) The organic semiconductor as described in any one of (1) to (3) above, wherein in formula (I), $A_1$ is an oxygen atom.

(5) The organic semiconductor as described in any one of (1) to (4) above, wherein the compound represented by formula (I) is a compound represented by formula (II):

Formula (II):

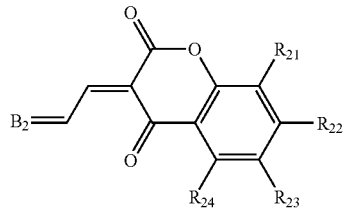

wherein each of $R_{21}$, $R_{22}$, $R_{23}$ and $R_{24}$ independently represents a hydrogen atom or a substituent W having the same meaning as the substituent W in formula (I), each of adjacent pairs $R_{21}$ and $R_{22}$, $R_{22}$ and $R_{23}$, and $R_{23}$ and $R_{24}$ may be linked to form a ring; and $B_2$ has the same meaning as $B_1$ in formula (I).

(6) A photoelectric conversion element, comprising:
a photoelectric conversion part that contains:
a first electrode and a second electrode; and
an organic photoelectric conversion film disposed between the first and second electrodes,
wherein the organic photoelectric conversion film contains the organic semiconductor as described in any one of (1) to (5) above.

(7) The photoelectric conversion element as described in (6) above,
wherein one of the first and second electrodes is an electrode on a light incident side, and the electrode on the light incident side is a transparent electrode.

(8) The photoelectric conversion element as described in (7) above,
wherein the transparent electrode (transparent electrically conductive thin film) contains a transparent electrically conductive oxide.

(9) The photoelectric conversion element as described in any one of (6) to (8) above, further comprising:
a hole-blocking layer between the organic photoelectric conversion film and at least one of the first and second electrodes.

(10) The photoelectric conversion element as described in any one of (6) to (9) above, further comprising:

an electron-blocking layer between the organic photoelectric conversion film and at least one of the first and second electrodes.

(11) The photoelectric conversion element as described in any one of (6) to (10) above, further comprising:
a semiconductor substrate in which at least one of the photoelectric conversion part is stacked on an upper side of the semiconductor substrate;
an electric charge accumulating part formed inside of the semiconductor substrate, the electric charge accumulating part accumulating electric charges generated in the organic photoelectric conversion film contained in the photoelectric conversion part; and
a connection part that electrically connects one of the first and second electrodes for collecting the electric charges to the electric charge accumulating part.

(12) A solid-state image device, comprising:
a plurality of the photoelectric conversion elements as described in (11) above disposed in an array manner; and
a plurality of signal readout parts, each of the plurality of signal readout parts reading out signals in proportion to the electric charges accumulated in a respective one of the electric charge accumulating parts of the plurality of the photoelectric conversion elements.

(13) An image device, comprising:
the photoelectric conversion element as described in any one of (6) to (11) above.

DETAILED DESCRIPTION OF THE INVENTION

Figure 1:
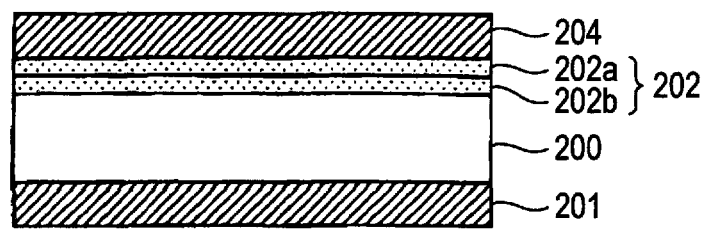
FIG. 1 is a schematic cross-sectional view showing one example of the photoelectric conversion element having a charge-blocking layer of this exemplary embodiment.

In the present invention, optical and semiconductor properties of not passing a current at dark time and passing a current at bright time are important, and an organic photoelectric conversion element can be obtained by applying these properties as a thin film.

In the organic photoelectric conversion element of the present invention, for realizing high photoelectric conversion efficiency, low dark current and high-speed response, the organic photoelectric conversion film used preferably satisfies the following requirements.

In terms of high photoelectric conversion efficiency and high-speed response, it is necessary that signal charges after exciton dissociation can be swiftly and losslessly transmitted to both electrodes. That is, high mobility and high charge transport ability with a small number of carrier trapping sites are necessary.

As regards the high photoelectric conversion efficiency, the exciton preferably has a small stabilization energy so that the exciton can be swiftly dissociated by an electric field applied from outside or an electric field generated inside due to pn junction or the like (high exciton dissociation efficiency).

Exciton generation at dark time gives rise to a dark current. In order to reduce as much a carrier generated in the inside at dark time as possible, a film structure or material having a small number of intermediate levels in the inside or containing a small amount of impurities working out to one of causes of the intermediate level is preferably selected.

In the case of stacking a plurality of layers, matching of energy level with the adjacent layer is necessary, and if an energetic barrier is formed, this inhibits charge transport. Therefore, the energy level is preferably matched with that of the adjacent layer.

In the case of forming the organic photoelectric conversion film by a vapor deposition method, the decomposition temperature is preferably as much higher than the vapor deposition temperature as possible, because thermal decomposition during vacuum deposition can be suppressed. The vapor deposition method facilitates formation of a uniform film and can minimize the possibility of impurity mixing, and therefore, the film formation is preferably performed by the vapor deposition method.

The molar absorption coefficient is preferably large, because sufficiently high light absorptance is obtained and in turn the light utilization efficiency is raised. When the light absorptance is the same, a material having a large molar absorption coefficient can be easily formed into a thin film and this is advantageous in that the applied electric field becomes large and the photoelectric conversion efficiency is increased under the same voltage application conditions and in that the driving voltage of the device becomes low under the same electric field application conditions.

As a result of intensive studies, the present inventors have found an organic semiconductor thin film using a compound represented by formula (I), which satisfies the above-described necessary requirements, can realize high photoelectric conversion efficiency, low dark current and high-speed response and exhibits good vapor deposition property. The thickness of the organic semiconductor thin film (organic dye layer) is preferably larger in view of light absorption, but considering the ratio of the portion not participating in the electric charge separation, the thickness of the organic dye layer is preferably from 30 to 300 nm, more preferably from 50 to 250 nm, still more preferably from 80 to 200 nm.

A color photoelectric conversion film where BGR photoelectric conversion films with good color reproduction, that is, three layers of blue photoelectric conversion film, green photoelectric conversion film and red photoelectric conversion film, are stacked can be preferably produced using the organic semiconductor of the present invention. In the case of applying the compound represented by formula (I) to an organic photoelectric conversion film, any of the BGR photoelectric conversion films may be produced by selecting the compound used, but the compound is preferably used as a blue photoelectric conversion film, a green photoelectric conversion film or a red photoelectric conversion film.

The compound represented by formula (I) for use in the present invention is described. In formula (I), $A_1$ represents O, S or N—$R_{15}$, each of $R_{11}$, $R_{12}$, $R_{13}$, $R_{14}$ and $R_{15}$ independently represents a hydrogen atom or a substituent, $R_{11}$ and $R_{12}$ may be linked to form a ring, and $B_1$ represents a ring structure containing at least one nitrogen atom. n1 represents an integer of 0 to 2. In the present invention, the compound of formula (I) is used also as a semiconductor and therefore, those not containing an ionic atom group that blocks transport of electric charges are preferred.

As for the substituent represented by $R_{11}$ to $R_{15}$, those described below as the substituent W may be applied.

Examples of the substituent W include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group (may also be called a hetero ring group), a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boronic acid group (—B(OH)$_2$), a phosphato group (—OPO(OH)$_2$), a sulfato group (—OSO$_3$H) and other known substituents.

More specifically, W represents, for example, the following (1) to (48):

(1) a halogen atom,
such as fluorine atom, chlorine atom, bromine atom and iodine atom;

(2) an alkyl group,
a linear, branched or cyclic, substituted or unsubstituted alkyl group, the alkyl group including, for example, (2-a) to (2-e):

(2-a) an alkyl group,
preferably an alkyl group having a carbon number of 1 to 30 (e.g., methyl, ethyl, n-propyl, isopropyl, tert-butyl, n-octyl, eicosyl, 2-chloroethyl, 2-cyanoethyl, 2-ethylhexyl), (2-b) a cycloalkyl group,
preferably a substituted or unsubstituted cycloalkyl group having a carbon number of 3 to 30 (e.g., cyclohexyl, cyclopentyl, 4-n-dodecylcyclohexyl), (2-c) a bicycloalkyl group,
preferably a substituted or unsubstituted bicycloalkyl group having a carbon number of 5 to 30 (e.g., bicyclo[1,2,2]heptan-2-yl, bicyclo[2,2,2]octan-3-yl), (2-d) a tricycloalkyl group,
preferably a substituted or unsubstituted tricycloalkyl group having a carbon number of 7 to 30 (e.g., 1-adamantyl), and (2-e) a polycyclic cycloalkyl group having many ring structures,
here, the alkyl group in the substituent described below (for example, the alkyl group in an alkylthio group) means an alkyl group having such a concept but also includes an alkenyl group and an alkynyl group;

(3) an alkenyl group,
a linear, branched or cyclic, substituted or unsubstituted alkenyl group, the alkenyl group including (3-a) to (3-c):

(3-a) an alkenyl group,
preferably a substituted or unsubstituted alkenyl group having a carbon number of 2 to 30 (e.g., vinyl, allyl, prenyl, geranyl, oleyl), (3-b) a cycloalkenyl group,
preferably a substituted or unsubstituted cycloalkenyl group having a carbon number of 3 to 30 (e.g., 2-cyclopenten-1-yl, 2-cyclohexen-1-yl), and (3-c) a bicycloalkenyl group,
a substituted or unsubstituted bicycloalkenyl group, preferably a substituted or unsubstituted bicycloalkenyl group having a carbon number of 5 to 30 (e.g., bicyclo[2,2,1]hept-2-en-1-yl, bicyclo[2,2,2]oct-2-en-4-yl)];

(4) an alkynyl group,
preferably a substituted or unsubstituted alkynyl group having a carbon number of 2 to 30 (e.g., ethynyl, propargyl, trimethylsilylethynyl);

(5) an aryl group,
preferably a substituted or unsubstituted aryl group having a carbon number of 6 to 30 (e.g., phenyl, p-tolyl, naphthyl, m-chlorophenyl, o-hexadecanoylaminophenyl, ferrocenyl);

(6) a heterocyclic group,
preferably a monovalent group obtained by removing one hydrogen atom from a 5- or 6-membered substituted or unsubstituted, aromatic or non-aromatic heterocyclic compound, more preferably a 5- or 6-membered aromatic heterocyclic group having a carbon number of 2 to 50 (e.g., 2-furyl, 2-thienyl, 2-pyrimidinyl, 2-benzothiazolyl; the heterocyclic group may also be a cationic heterocyclic group such as 1-methyl-2-pyridinio and 1-methyl-2-quinolinio);

(7) a cyano group;

(8) a hydroxy group;

(9) a nitro group;

(10) a carboxyl group;

(11) an alkoxy group,
preferably a substituted or unsubstituted alkoxy group having a carbon number of 1 to 30 (e.g., methoxy, ethoxy, isopropoxy, tert-butoxy, n-octyloxy, 2-methoxyethoxy);

(12) an aryloxy group,
preferably a substituted or unsubstituted aryloxy group having a carbon number of 6 to 30 (e.g., phenoxy, 2-methylphenoxy, 4-tert-butylphenoxy, 3-nitrophenoxy, 2-tetradecanoylaminophenoxy);

(13) a silyloxy group,
preferably a silyloxy group having a carbon number of 3 to 20 (e.g., trimethylsilyloxy, tert-butyldimethylsilyloxy);

(14) a heterocyclic oxy group,
preferably a substituted or unsubstituted heterocyclic oxy group having a carbon number of 2 to 30 (e.g., 1-phenyltetrazol-5-oxy, 2-tetrahydropyranyloxy);

(15) an acyloxy group,
preferably a formyloxy group, a substituted or unsubstituted alkylcarbonyloxy group having a carbon number of 2 to 30, or a substituted or unsubstituted arylcarbonyloxy group having a carbon number of 6 to 30 (e.g., formyloxy, acetyloxy, pivaloyloxy, stearoyloxy, benzoyloxy, p-methoxyphenylcarbonyloxy);

(16) a carbamoyloxy group,
preferably a substituted or unsubstituted carbamoyloxy group having a carbon number of 1 to 30 (e.g., N,N-dimethylcarbamoyloxy, N,N-diethylcarbamoyloxy, morpholinocarbonyloxy, N,N-di-n-octylaminocarbonyloxy, N-n-octylcarbamoyloxy);

(17) an alkoxycarbonyloxy group,
preferably a substituted or unsubstituted alkoxycarbonyloxy group having a carbon number of 2 to 30 (e.g., methoxycarbonyloxy, ethoxycarbonyloxy, tert-butoxycarbonyloxy, n-octylcarbonyloxy);

(18) an aryloxycarbonyloxy group,
preferably a substituted or unsubstituted aryloxycarbonyloxy group having a carbon number of 7 to 30 (e.g., phenoxycarbonyloxy, p-methoxyphenoxycarbonyloxy, p-n-hexadecyloxyphenoxycarbonyloxy);

(19) an amino group,
preferably an amino group, a substituted or unsubstituted alkylamino group having a carbon number of 1 to 30, or a substituted or unsubstituted anilino group having a carbon number of 6 to 30 (e.g., amino, methylamino, dimethylamino, anilino, N-methyl-anilino, diphenylamino);

(20) an ammonio group,
preferably an ammonio group or an ammonio group substituted by a substituted or unsubstituted alkyl, aryl or heterocyclic group having a carbon number of 1 to 30 (e.g., trimethylammonio, triethylammonio, diphenylmethylammonio);

(21) an acylamino group,
preferably a formylamino group, a substituted or unsubstituted alkylcarbonylamino group having a carbon number of 1 to 30, or a substituted or unsubstituted arylcarbonylamino group having a carbon number of 6 to 30 (e.g., formylamino, acetylamino, pivaloylamino, lauroylamino, benzoylamino, 3,4,5-tri-n-octyloxyphenylcarbonylamino);

(22) an aminocarbonylamino group,
preferably a substituted or unsubstituted aminocarbonylamino group having a carbon number of 1 to 30 (e.g., carbamoylamino, N,N-dimethylaminocarbonylamino, N,N-diethylaminocarbonylamino, morpholinocarbonylamino);

(23) an alkoxycarbonylamino group,
preferably a substituted or unsubstituted alkoxycarbonylamino group having a carbon number of 2 to 30 (e.g., methoxycarbonylamino, ethoxycarbonylamino, tert-butoxycarbonylamino, n-octadecyloxycarbonylamino, N-methylmethoxycarbonylamino);
(24) an aryloxycarbonylamino group,
preferably a substituted or unsubstituted aryloxycarbonylamino group having a carbon number of 7 to 30 (e.g., phenoxycarbonylamino, p-chlorophenoxycarbonylamino, m-n-octyloxyphenoxycarbonylamino);
(25) a sulfamoylamino group,
preferably a substituted or unsubstituted sulfamoylamino group having a carbon number of 0 to 30 (e.g., sulfamoylamino, N,N-dimethylaminosulfonylamino, N-n-octylaminosulfonylamino);
(26) an alkyl- or aryl-sulfonylamino group,
preferably a substituted or unsubstituted alkylsulfonylamino group having a carbon number of 1 to 30, or a substituted or unsubstituted arylsulfonylamino group having a carbon number of 6 to 30 (e.g., methylsulfonylamino, butylsulfonylamino, phenylsulfonylamino, 2,3,5-trichlorophenylsulfonylamino, p-methylphenylsulfonylamino);
(27) a mercapto group;
(28) an alkylthio group,
preferably a substituted or unsubstituted alkylthio group having a carbon number of 1 to 30 (e.g., methylthio, ethylthio, n-hexadecylthio);
(29) an arylthio group,
preferably a substituted or unsubstituted arylthio group having a carbon number of 6 to 30 (e.g., phenylthio, p-chlorophenylthio, m-methoxyphenylthio);
(30) a heterocyclic thio group,
preferably a substituted or unsubstituted heterocyclic thio group having a carbon number of 2 to 30 (e.g., 2-benzothiazolylthio, 1-phenyltetrazol-5-ylthio);
(31) a sulfamoyl group,
preferably a substituted or unsubstituted sulfamoyl group having a carbon number of 0 to 30 (e.g., N-ethylsulfamoyl, N-(3-dodecyloxypropyl)sulfamoyl, N, N-dimethylsulfamoyl, N-acetylsulfamoyl, N-benzoylsulfamoyl, N—(N'-phenylcarbamoyl)sulfamoyl);
(32) a sulfo group;
(33) an alkyl- or aryl-sulfinyl group,
preferably a substituted or unsubstituted alkylsulfinyl group having a carbon number of 1 to 30, or a substituted or unsubstituted arylsulfinyl group having a carbon number of 6 to 30 (e.g., methylsulfinyl, ethylsulfinyl, phenylsulfinyl, p-methylphenylsulfinyl);
(34) an alkyl- or aryl-sulfonyl group,
preferably a substituted or unsubstituted alkylsulfonyl group having a carbon number of 1 to 30, or a substituted or unsubstituted arylsulfonyl group having a carbon number of 6 to 30 (e.g., methylsulfonyl, ethylsulfonyl, phenylsulfonyl, p-methylphenylsulfonyl);
(35) an acyl group,
preferably a formyl group, a substituted or unsubstituted alkylcarbonyl group having a carbon number of 2 to 30, a substituted or unsubstituted arylcarbonyl group having a carbon number of 7 to 30, or a substituted or unsubstituted heterocyclic carbonyl group having a carbon number of 4 to 30 and being bonded to a carbonyl group through a carbon atom (e.g., acetyl, pivaloyl, 2-chloroacetyl, stearoyl, benzoyl, p-n-octyloxyphenylcarbonyl, 2-pyridylcarbonyl, 2-furylcarbonyl);
(36) an aryloxycarbonyl group,
preferably a substituted or unsubstituted aryloxycarbonyl group having a carbon number of 7 to 30 (e.g., phenoxycarbonyl, o-chlorophenoxycarbonyl, m-nitrophenoxycarbonyl, p-tert-butylphenoxycarbonyl);
(37) an alkoxycarbonyl group,
preferably a substituted or unsubstituted alkoxycarbonyl group having a carbon number of 2 to 30 (e.g., methoxycarbonyl, ethoxycarbonyl, tert-butoxycarbonyl, n-octadecyloxycarbonyl);
(38) a carbamoyl group,
preferably a substituted or unsubstituted carbamoyl group having a carbon number of 1 to 30 (e.g., carbamoyl, N-methylcarbamoyl, N,N-dimethylcarbamoyl, N, N-di-n-octylcarbamoyl, N-(methylsulfonyl)carbamoyl);
(39) an aryl or heterocyclic azo group,
preferably a substituted or unsubstituted arylazo group having a carbon number of 6 to 30, or a substituted or unsubstituted heterocyclic azo group having a carbon number of 2 to 30 (e.g., phenylazo, p-chlorophenylazo, 5-ethylthio-1,3,4-thiadiazol-2-ylazo);
(40) an imido group,
preferably N-succinimido or N-phthalimido;
(41) a phosphino group,
preferably a substituted or unsubstituted phosphino group having a carbon number of 2 to 30 (e.g., dimethylphosphino, diphenylphosphino, methylphenoxyphosphino);
(42) a phosphinyl group,
preferably a substituted or unsubstituted phosphinyl group having a carbon number of 2 to 30 (e.g., phosphinyl, dioctyloxyphosphinyl, diethoxyphosphinyl);
(43) a phosphinyloxy group,
preferably a substituted or unsubstituted phosphinyloxy group having a carbon number of 2 to 30 (e.g., diphenoxyphosphinyloxy, dioctyloxyphosphinyloxy);
(44) a phosphinylamino group,
preferably a substituted or unsubstituted phosphinylamino group having a carbon number of 2 to 30 (e.g., dimethoxyphosphinylamino, dimethylaminophosphinylamino);
(45) a phospho group;
(46) a silyl group,
preferably a substituted or unsubstituted silyl group having a carbon number of 3 to 30 (e.g., trimethylsilyl, triethylsilyl, triisopropylsilyl, tert-butyldimethylsilyl, phenyldimethylsilyl);
(47) a hydrazino group,
preferably a substituted or unsubstituted hydrazino group having a carbon number of 0 to 30 (e.g., trimethylhydrazino); or
(48) a ureido group,
preferably a substituted or unsubstituted ureido group having a carbon number of 0 to 30 (e.g., N,N-dimethylureido).

Also, two W's may form a ring in cooperation. The ring formed includes an aromatic or non-aromatic hydrocarbon, a heterocyclic ring, and a polycyclic condensed ring formed by the combination of these rings. Examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring and a phenazine ring.

Among these substituents W, those having a hydrogen atom may be deprived of the hydrogen atom and further substituted by the above-described group. Examples of such a substituent include a —CONHSO$_2$— group (sulfonylcarbamoyl group or carbonylsulfamoyl group), a —CONHCO— group (carbonylcarbamoyl group) and an —SO$_2$NHSO$_2$— group (sulfonylsulfamoyl group). Specific examples thereof include an alkylcarbonylaminosulfonyl group (e.g., acetylaminosulfonyl), an arylcarbonylaminosulfonyl group (e.g., benzoylaminosulfonyl), an alkylsulfonylaminocarbonyl group (e.g., methylsulfonylaminocarbonyl) and an arylsulfonylaminocarbonyl group (e.g., p-methylphenylsulfonylaminocarbonyl).

$A_1$ represents an oxygen atom, a sulfur atom or N—$R_{15}$, wherein $R_{15}$ represents a hydrogen atom or a substituent. $A_1$ is preferably an oxygen atom or N—$R_{15}$, more preferably an oxygen atom.

$B_1$ represents a ring structure containing at least one nitrogen atom and, because of the structure of formula (I), is a divalent substituent. Examples of the ring structure include nitrogen atom-containing heterocyclic rings (Hw) out of examples of the ring formed by cooperation of two W's in the above-described substituents W and include a pyrrole ring, an imidazole ring, an oxazole ring, a thiazole ring, a selenazole ring, a tellurazole ring, a pyridine ring, a pyrazine ring, a pyrimidine ring, a pyridazine ring, an indolizine ring, an indole ring, a quinolidine ring, a quinoline ring, a phthalazine ring, a naphthylidine ring, a quinoxaline ring, a quinoxazoline ring, an isoquinoline ring, a phenanthridine ring, an acridine ring, a phenanthroline ring and a phenazine ring. Among these, preferred ring structures are represented by the following formula $B_{11}$:

Formula $B_{11}$:

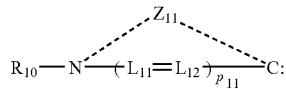

In formula $B_{11}$, $Z_{11}$ represents an atomic group necessary for forming a nitrogen-containing heterocyclic ring, $R_{10}$ represents a hydrogen atom or a substituent, each of $L_{11}$ and $L_{12}$ represents a methine group, and $p_{11}$ represents an integer of 0 or 1.

The nitrogen-containing heterocyclic ring formed by $Z_{11}$ includes the above-described Hw, and preferred examples of the nitrogen-containing heterocyclic ring include an oxazole having a carbon number (hereinafter referred to as a "C number") of 3 to 25 (e.g., 2-3-methyloxazolyl, 2-3-ethyloxazolyl, 2-3-sulfopropyloxazolyl, 2-6-dimethylamino-3-methylbenzoxazolyl, 2-3-ethylbenzoxazolyl, 2-3-sulfopropyl-γ-naphthoxazolyl, 2-3-ethyl-α-naphthoxazolyl, 2-3-methyl-β-naphthoxazolyl, 2-3-sulfopropyl-β-naphthoxazolyl, 2-5-chloro-3-ethyl-α-naphthoxazolyl, 2-5-chloro-3-ethylbenzoxazolyl, 2-5-chloro-3-sulfopropylbenzoxazolyl, 2-5,6-dichloro-3-sulfopropylbenzoxazolyl, 2-5-bromo-3-sulfopropylbenzoxazolyl, 2-3-ethyl-5-phenylbenzoxazolyl, 2-5-phenyl-3-sulfopropylbenzoxazolyl, 2-5-(4-bromophenyl)-3-sulfobutylbenzoxazolyl, 2-5-(1-pyrrolyl)-3-sulfopropylbenzoxazolyl, 2-5,6-dimethyl-3-sulfopropylbenzoxazolyl, 2-3-ethyl-5-methoxybenzoxazolyl, 2-3-ethyl-5-sulfobenzoxazolyl, 2-3-methyl-α-naphthoxazolyl, 2-3-ethyl-β-naphthoxazolyl, 2-3-methyl-γ-naphthoxazolyl), a thiazole ring having a C number of 3 to 25 (e.g., 2-3-methylthiazolyl, 2-3-ethylthiazolyl, 2-3-sulfopropylthiazolyl, 2-3-methylbenzothiazolyl, 2-3-sulfopropylbenzothiazolyl, 2-3-methyl-α-naphthothiazolyl, 2-3-methyl-β-naphthothiazolyl, 2-3-ethyl-γ-naphthothiazolyl, 2-3,5-dimethylbenzothiazolyl, 2-5-chloro-3-ethylbenzothiazolyl, 2-5-chloro-3-sulfopropylbenzothiazolyl, 2-3-ethyl-5-iodobenzothiazolyl, 2-5-bromo-3-methylbenzothiazolyl, 2-3-ethyl-5-methoxybenzothiazolyl, 2-5-phenyl-3-sulfopropylbenzothiazolyl), an imidazole ring having a C number of 3 to 25 (e.g., 2-1,3-dimethylimidazolyl, 2-1,3-diethylimidazolyl, 2-1,3-dimethylbenzimidazolyl, 2-5,6-dichloro-1,3-dimethylbenzimidazolyl, 2-5,6-dichloro-3-ethyl-1-sulfopropylbenzimidazolyl 2-5-chloro-6-cyano-1,3-diethylbenzimidazolyl, 2-5-chloro-1,3-diethyl-6-rifluoromethylbenzimidazolyl, 2-1,3-dimethyl-α-naphthimidazolyl, 2-1,3-dimethyl-γ-naphthimidazolyl), an indolenine ring having a C number of 10 to 30 (e.g., 3,3-dimethyl-1-methylindolenine, 3,3-dimethyl-1-phenylindolenine, 3,3-dimethyl-1-pentylindolenine, 3,3-dimethyl-1-sulfopropylindolenine, 5-chloro-1,3,3-trimethylindolenine, 5-methoxy-1,3,3-trimethylindolenine, 5-carboxy-1,3,3-trimethylindolenine, 5-carbamoyl-1,3,3-trimethylindolenine, 1,3,3-trimethyl-4,5-benzindolenine, 1,3,3-trimethyl-6,7-benzindolenine), a quinoline ring having a C number of 9 to 25 (e.g., 2-1-methylquinolyl, 2-1-sulfobutylquinolyl, 4-1-pentylquinolyl, 4-1-sulfoethylquinolyl, 4-1-methyl-7-chloroquinolyl), a selenazole ring having a C number of 3 to 25 (e.g., 2-3-methylbenzoselenazolyl), and a pyridine ring having a C number of 5 to 25 (e.g., 2-pyridyl, 4-pyridyl). Other examples include a thiazoline ring, an oxazoline ring, a selenazoline ring, a tellurazoline ring, a tellurazole ring, a benzotellurazole ring, an imidazoline ring, an imidazo[4,5-quinoxaline] ring, an oxadiazole ring, a thiadiazole ring, a tetrazole ring, a pyrimidine ring, a pyrazine ring, a pyridazine ring, an indolizine ring, an indole ring, a quinolizine ring, a phthalazine ring, a naphthylidine ring, a quinoxaline ring, an quinoxazoline ring, an isoquinoline ring, a phenanthridine ring, an acridine ring, a phenanthroline ring and a phenazine ring.

Such a nitrogen-containing heterocyclic ring may be substituent, and preferred examples of the substituent include an alkyl group, an alkenyl group, a cycloalkyl group, an aryl group, a heterocyclic group, an alkynyl group, a halogen atom, an amino group, a cyano group, a nitro group, a hydroxyl group, a mercapto group, a carboxyl group, a sulfo group, a phosphonic acid group, an acyl group, an alkoxy group, an aryloxy group, an alkylthio group, an arylthio group, an alkylsulfonyl group, an arylsulfonyl group, a sulfamoyl group, a carbamoyl group, an acylamino group, an imino group, an acyloxy group, an alkoxycarbonyl group and carbamoylamino group. Among these, more preferred are an alkyl group, an aryl group, a heterocyclic group, a halogen atom, a cyano group, a carboxyl group, a sulfo group, an alkoxy group, a sulfamoyl group, a carbamoyl group and an alkoxycarbonyl group.

The heterocyclic ring may be further condensed with another ring. Preferred examples of the ring with which the heterocyclic ring is condensed include a benzene ring, a benzofuran ring, a pyridine ring, a pyrrole ring, an indole ring and a thiophene ring.

The nitrogen-containing heterocyclic ring is preferably an imidazole ring, an oxazole ring, a thiazole ring, a pyridine ring, a quinoline ring or a 3,3-di-substituted indolenine ring.

$R_{10}$ is preferably a hydrogen atom, an alkyl group (preferably having a C number of 1 to 20, e.g., methyl, ethyl, n-propyl, isopropyl, n-butyl, n-pentyl, benzyl, 3-sulfopropyl, 4-sulfobutyl, 3-methyl-3-sulfopropyl, 2'-sulfobenzyl, carboxymethyl, 5-carboxypentyl), an alkenyl group (preferably having a C number of 2 to 20, e.g., vinyl, allyl), an aryl group (preferably having a C number of 6 to 20, e.g., phenyl, 2-chlorophenyl, 4-methoxyphenyl, 3-methylphenyl, 1-naphthyl), or a heterocyclic group (preferably having a C number of 1 to 20, e.g., pyridyl, thienyl, furyl, thiazolyl, imidazolyl, pyrazolyl, pyrrolidino, piperidino, morpholino), more preferably an alkyl group or an aryl group, still more preferably an alkyl group (preferably an alkyl group having a C number of 1 to 6).

Each of $L_{11}$ and $L_{12}$ independently represents a methine group which may have a substituent (examples of the preferred substituent are the same as examples of the substituent W), and preferred examples of the substituent include an alkyl group, a halogen atom, a nitro group, an alkoxy group, an aryl group, a nitro group, a heterocyclic group, an aryloxy group, an acylamino group, a carbamoyl group, a sulfo group, a hydroxy group, a carboxy group, an alkylthio group and a cyano group. The substituent is more preferably an alkyl group.

Each of $L_{11}$ and $L_{12}$ is preferably an unsubstituted methine group or an alkyl group (preferably having a C number of 1 to 6)-substituted methine group, more preferably an unsubstituted methine group.

$p_{11}$ represents an integer of 0 or 1 and is preferably 0.

Preferred atomic groups necessary for forming the nitrogen-containing heterocyclic ring include H-1 to H-13 set forth below. In the structural formulae, ":" indicates the substitution position.

H-1
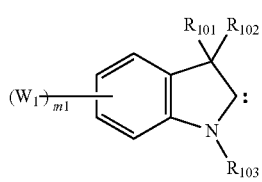

H-2
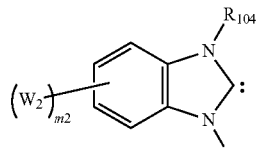

H-3
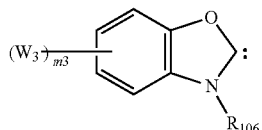

H-4
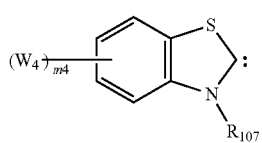

H-5
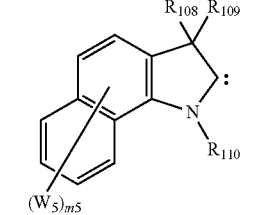

-continued

H-6
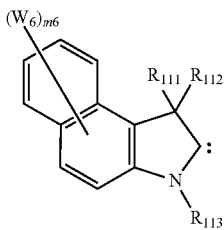

H-7
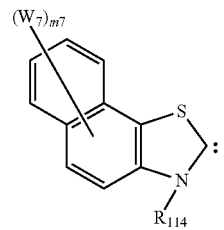

H-8
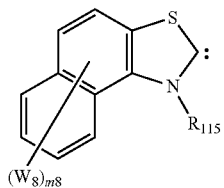

H-9
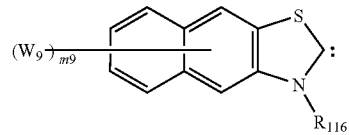

H-10
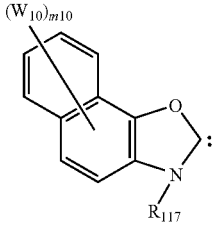

H-11
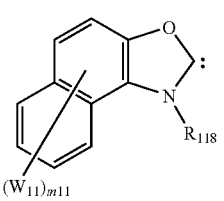

H-12
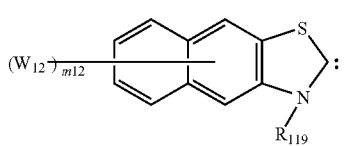

H-13
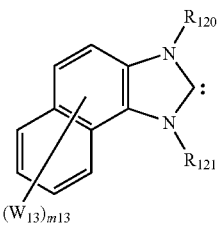

In the formulae above, $W_1$ to $W_{13}$ each represents a hydrogen atom or a substituent, $R_{101}$ to $R_{121}$ each represents a hydrogen atom or a substituent, m1 to m4 each represents an integer of 0 to 4, m5 to m13 each represents an integer of 0 to 6, and when m1 to m13 each is an integer of 2 or more, each of $W_1$ to $W_{13}$ may be the same as or different from every other $W_1$ to $W_{13}$.

The substituent represented by $W_1$ to $W_{13}$ may be selected from the above-described substituents W and is preferably an alkyl group, an alkenyl group, an aryl group, a halogen atom, an alkoxy group, an alkylamino group, a carbonyl group, a thiocarbonyl group, an oxycarbonyl group or an aromatic heterocyclic group, more preferably an alkyl group or an aryl group. The total carbon umber thereof is preferably from 1 to 18, more preferably from 1 to 6, and above all, a methyl group, an ethyl group, a propyl group and a butyl groups are preferred. In H-1 to H-13, the number of substituents represented by $W_1$ to $W_{13}$ is preferably 1 or 2, more preferably 1.

The substituent represented by $R_{101}$ to $R_{121}$ may be selected from the above-described substituents W and is preferably an alkyl group, an alkenyl group, an aryl group or an aromatic heterocyclic group, more preferably an alkyl group or an aryl group, still more preferably an alkyl group. The total carbon umber thereof is preferably from 1 to 18, more preferably from 1 to 6, still more preferably from 1 to 4, and above all, a methyl group, an ethyl group, a propyl group and a butyl groups are preferred.

Each of $R_{11}$, $R_{12}$, $R_{13}$, $R_{14}$ and $R_{15}$ independently represents a hydrogen atom or a substituent, and, for example, those described as the substituent W may be applied.

The substituent represented by $R_{11}$ and $R_{12}$ is preferably an alkyl group, an alkenyl group, an aryl group, an alkoxy group, an aryloxy group, a carbonyl group, a thiocarbonyl group, an oxycarbonyl group, an acylamino group, a carbamoyl group, a sulfonylamino group, a sulfamoyl group, a sulfonyl group, a sulfinyl group, a phosphoryl group, an imino group, a halogen atom, a silyl group or an aromatic heterocyclic group. The total carbon umber thereof is preferably from 1 to 18, more preferably from 4 to 6. A structure where $R_{11}$ and $R_{12}$ are linked to form a ring is preferred, and examples thereof include ring structures described above for the substituent W. In particular, formation of an aromatic hydrocarbon ring or an aromatic heterocyclic ring is preferred, and formation of a benzene ring or a naphthalene ring is more preferred.

Each of $R_{13}$ and $R_{14}$ independently represents a hydrogen atom or a substituent and, for example, those described as the substituent W may be applied. Each of $R_{13}$ and $R_{14}$ may be a heterocyclic ring (e.g., 2-benzothiazolyl, 2-naphthothiazolyl)-substituted methine group but is preferably a hydrogen atom or an alkyl group having a total carbon number of 1 to 6, more preferably a hydrogen atom. Specific examples include a hydrogen atom, a methyl group, an ethyl group, a propyl group and a phenyl group. Above all, a hydrogen atom is preferred.

$R_{15}$ represents a hydrogen atom or a substituent, and, for example, those described as the substituent W may be applied. $R_{15}$ is preferably an alkyl group having a total carbon number of 1 to 12 or an aryl group having a total carbon number of 6 to 12, more preferably an alkyl group having a total carbon number of 1 to 6, and specific examples thereof include a methyl group, an ethyl group, a propyl group, a butyl group and a phenyl group.

n1 is an integer of 0 or 2, preferably 0 or 1, more preferably 1.

The compound represented by formula (I) is preferably a compound represented by formula (II). In formula (II), $B_2$ has the same meaning as $B_1$ in formula (I), and preferred examples thereof are also the same.

In formula (II), each of $R_{21}$, $R_{22}$, $R_{23}$ and $R_{24}$ independently represents a hydrogen atom or a substituent, and examples of the substituent include the above-described substituents W. Also, each of adjacent pairs $R_{21}$ and $R_{22}$, $R_{22}$ and $R_{23}$, and $R_{23}$ and $R_{24}$ may be linked to form a ring (preferably a 5- or 6-membered ring, more preferably a benzene ring).

Each of $R_{21}$, $R_{22}$, $R_{23}$ and $R_{24}$ is preferably a hydrogen atom, an alkyl group or an aryl group or adjacent neighbors thereof are preferably linked to form a ring structure. In the case of an alkyl group, the carbon number is preferably 1 to 6, and in the case of an aryl group or a ring structure, the total carbon umber is preferably form 4 to 6. Examples thereof include a methyl group, an ethyl group, a propyl group, a butyl group, a phenyl group and formation of a benzene ring, and above all, a hydrogen atom and formation of a benzene ring are preferred.

Specific examples of the compound represented by formula (I) are set forth below, but the present invention is not limited thereto.

| Compound No. | $B_3$ | A |
|---|---|---|

$$B_3 \diagup\!\!\!\diagdown A$$

Compound 1

Compound 2

Compound 3

Compound 4

Compound 5

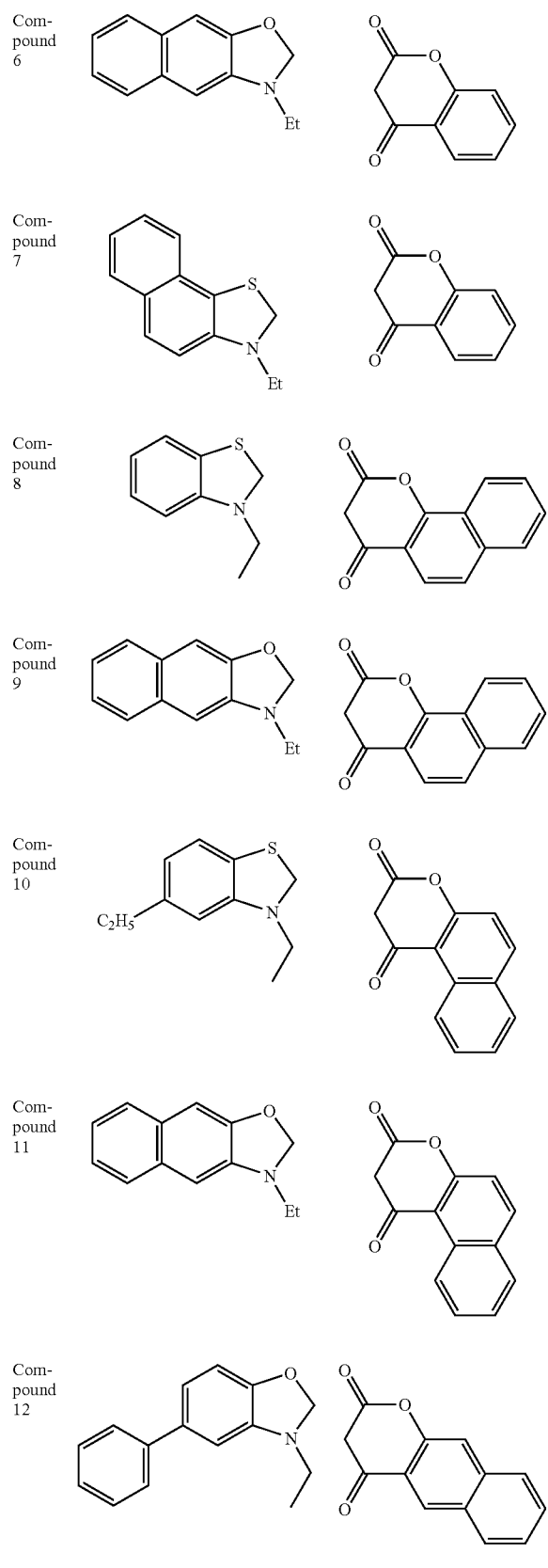
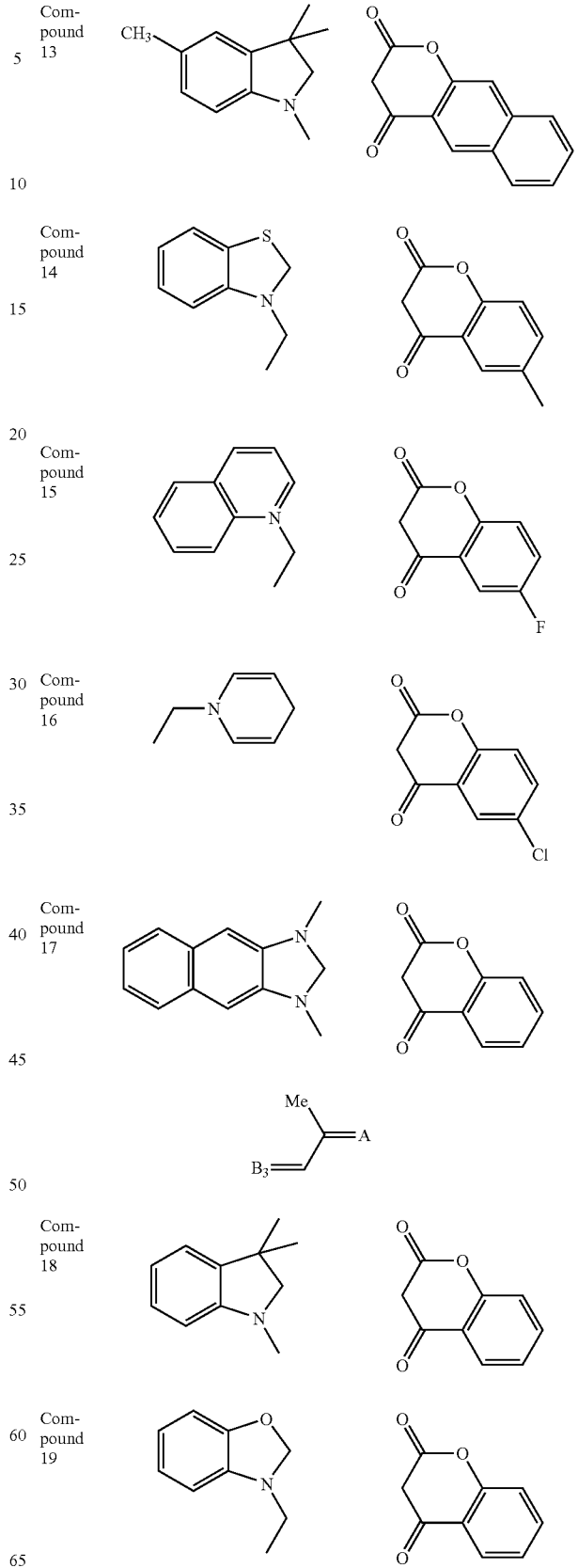

Compound 20
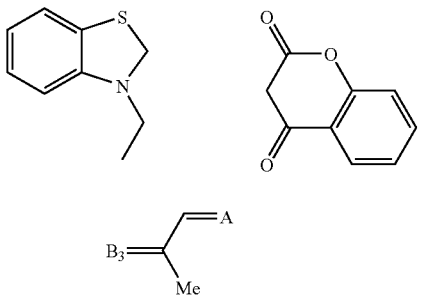

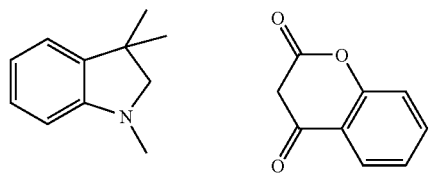

Compound 21

Compound 22
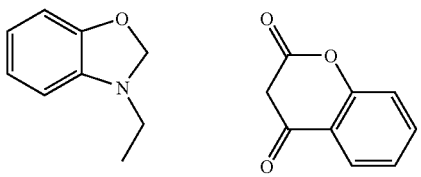

Compound 23
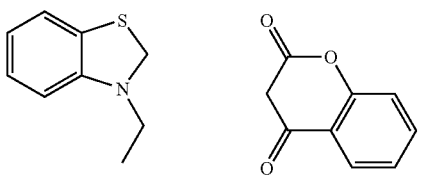

Compound 24:
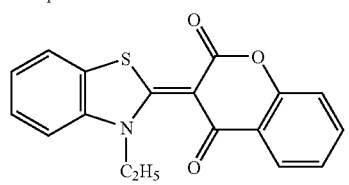

Compound 25:
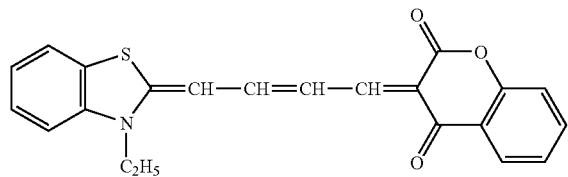

Compound 26:
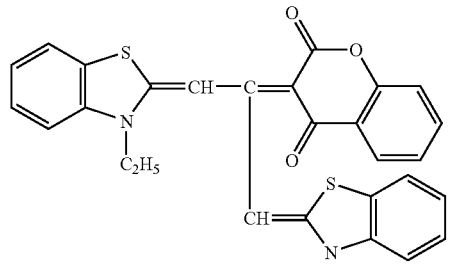

Compound 27:
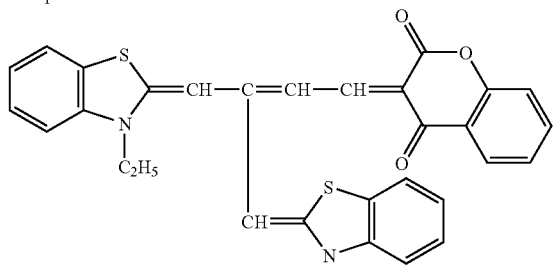

The compounds above may be produced by synthesis examples in working examples later, and compounds not described in the synthesis examples may also be produced in accordance with the synthesis examples.

[Preferred Embodiments of Photoelectric Conversion Element and Solid-State Image Device]

The embodiments of the present invention are described below by referring to the drawings.

While the compound represented by formula (I) of the present invention is preferably contained in the following photoelectric conversion film, preferred embodiments of the materials other than the compound represented by formula (I), which are used in the photoelectric conversion layer containing the photoelectric conversion film, the constituent elements such as other films used in the photoelectric conversion element containing the photoelectric conversion film, and the image device containing the photoelectric conversion element, are described below.

Embodiments capable of providing a photoelectric conversion element where injection of an electric charge (electron, hole) into the photoelectric conversion layer from the electrode can be suppressed and dark current can be thereby effectively reduced (first to sixth embodiments) are described below.

According to these embodiments, in a photoelectric conversion element having a pair of electrodes and a photoelectric conversion part containing a photoelectric conversion layer disposed between the pair of electrodes, a first charge-blocking layer for suppressing injection of an electric charge into the photoelectric conversion layer from one of the pair of electrodes is provided between one of the pair of electrodes and the photoelectric conversion layer and the first charge-blocking layer is formed to have a multiple-layer structure, whereby dark current can be suppressed more successfully than in the case of the first charge-blocking layer having a single-layer structure. Also in the construction where a second charge-blocking layer for suppressing injection of an electric charge into the photoelectric conversion layer from the other of the pair of electrodes is provided between the other of the pair of electrodes and the photoelectric conversion layer, the second charge-blocking layer is formed to have a multiple-layer structure, whereby dark current can be suppressed more successfully than in the case of the second charge-blocking layer having a single-layer structure. Furthermore, in the case where at least two layers out of a plurality of layers constituting each of the first charge-blocking layer and the second charge-blocking layer are composed of different materials, the effect of suppressing dark current can be more enhanced. In addition, in the case where at least two layers out of a plurality of layers are a layer composed of an inorganic material and a layer composed of an organic material, respectively, the effect of suppressing dark current can be more enhanced. Specific constructions of the charge-blocking layer are described in the following first to sixth embodiments.

(First Embodiment)

FIG. 1 is a schematic cross-sectional view showing one example of the construction of the photoelectric conversion part having a charge-blocking layer according to this embodiment.

In FIG. 1, reference numeral 200 is a photoelectric conversion layer, reference numeral 202 is a charge-blocking layer having a two-layer structure, reference numerals 202a and 202b are layers constituting the charge-blocking layer 202, and reference numerals 201 and 204 are electrodes.

For example, when the electrode 204 is provided as an electrode on the light incident side, since light needs to be incident into the photoelectric conversion layer 200, the electrode 204 is preferably composed of a material having high transparency. As for the electrode having high transparency, a transparent electrically conductive oxide (TCO) may be used. Similarly, the electrode 201 is preferably composed of a material having high transparency, because as seen in the construction of an image device described later, light needs to be transmitted to below the electrode. Also in the case where the electrode 201 is provided as an electrode on the light incident side, the electrode 204 and the electrode 201 are preferably composed of a material having high transparency.

The charge-blocking layer 202 is a layer for restraining the transport of an electric charge from the electrode 204 to the photoelectric conversion layer 200 when a voltage is applied to the electrode 201 and the electrode 204. In the case where the charge-blocking layer 202 has a single-layer structure, an intermediate level (e.g., impurity level) is present in the material itself constituting the charge-blocking layer 202, and an electric charge (electron, hole) is allowed to be transported through this intermediate level and cause an increase in the dark current. For preventing such transport, in this embodiment, the charge-blocking layer 202 is formed to have a two-layer structure but not a single-layer structure.

It is considered that when an interface is produced between the layers 202a and 202b constituting the charge-blocking layer 202, discontinuity is generated in the intermediate levels present in respective layers 202a and 202b and transport of the carrier through the intermediate levels or the like becomes difficult, as a result, dark current can be suppressed. However, if the layers 202a and 202b are formed of the same material, the intermediate levels present in respective layers 202a and 202b may become thoroughly the same. Accordingly, for more enhancing the effect of suppressing the dark current, the materials constituting respective layers 202a and 202b are preferably different.

Figure 2A:
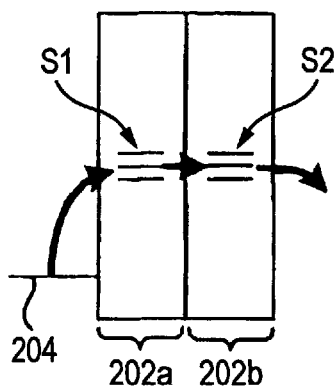
FIGS. 2A and 2B are energy diagrams showing the state of intermediate levels in the charge-blocking layer having a two-layer structure shown in FIG. 1.
Figure 2B:
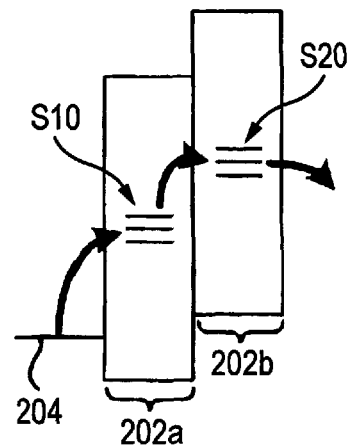

FIGS. 2A and 2B are energy diagrams showing the state of intermediate levels in the charge-blocking layer having a two-layer structure shown in FIG. 1; FIG. 2A shows a case where the layers 202a and 202b are formed of the same material, and FIG. 2B shows a case where respective layers 202a and 202b are formed of different materials.

In the case where the layers 202a and 202b are formed of the same material, as described above, an interface is produced and therefore, dark current can be suppressed as compared with a single-layer structure. However, if the intermediate levels (S1, S2) of respective layers 202a and 202b are present at energy positions of the same level as shown in FIG. 2A, transport of an electric charge via the intermediate levels (shown by arrows in the Figure) of respective layers 202a and 202b is allowed to occur.

Here, when the layers 202a and 202b are formed of different materials, as shown in FIG. 2B, the intermediate level (S20) of the layer 202b is located, for example, at a higher energy position than the intermediate level (S10) of the layer 202a and the difference in the energy level works as a barrier, so that the transport of an electric charge can be accordingly suppressed. In this way, positions of intermediate levels in respective layers can be unfailingly dispersed by forming two layers constituting the charge-blocking layer 202 from different materials, as a result, the effect of suppressing the carrier transport via intermediate levels can be enhanced.

In FIG. 1, an example of the photoelectric conversion element having one charge-blocking layer is shown, but even in the case where in FIG. 1, a charge-blocking layer for restraining transport of an electric charge from the electrode 201 to the photoelectric conversion layer 200 when applying a voltage to the electrodes 201 and 204 is provided between the electrode 201 and the photoelectric conversion layer 200, dark current can be suppressed by forming the charge-blocking layer to have a two-layer structure and furthermore, the dark current can be more successfully suppressed by forming these two layers from different materials.

Figure 3A:
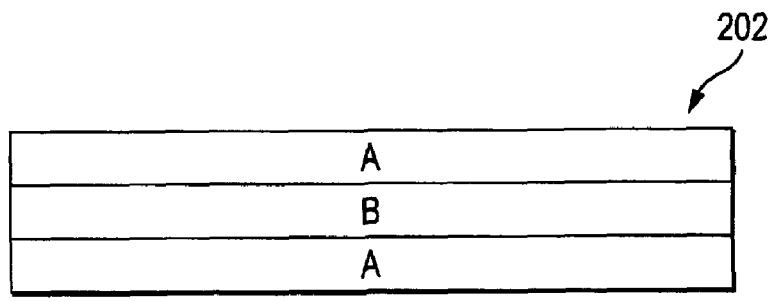
FIGS. 3A to 3D are views for explaining the combination of materials for respective layers when the charge-blocking layer shown in FIG. 1 has a three-layer structure.
Figure 3B:
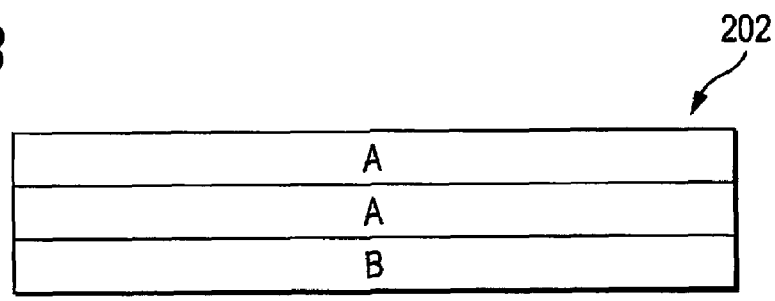
Figure 3C:
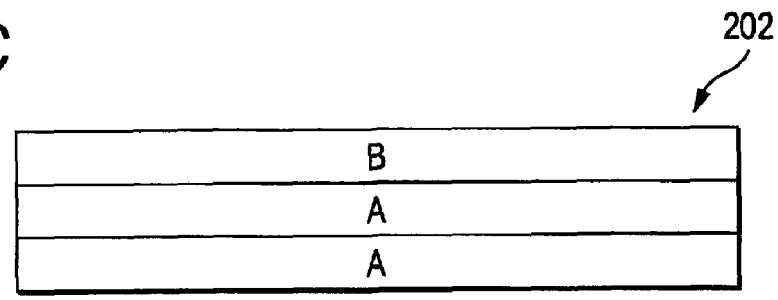
Figure 3D:
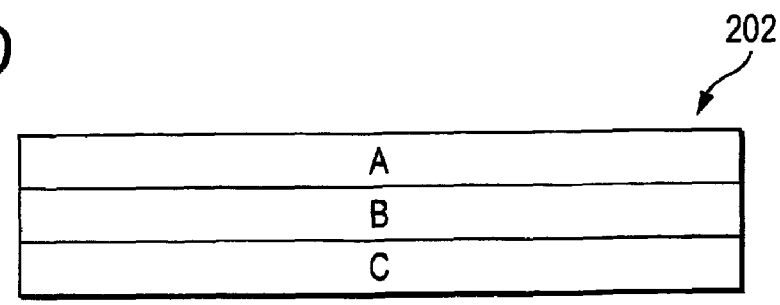

In the above, an example where the charge-blocking layer 202 has a two-layer structure is described, but the charge-blocking layer may have a structure consisting of three or more layers. In this case, as described above, when at least two layers out of the layers constituting the charge-blocking layer are formed of different materials, a step height between intermediate levels can be unfailingly formed inside of the charge-blocking layer. For example, in the case of a charge-blocking layer having a three-layer structure, a step height may be created, as shown in FIG. 3A, by forming the lowermost layer and the uppermost layer from a material A and forming the in-between intermediate layer from a material B that is different from the material A; as shown in FIG. 3B, by forming the lowermost layer from the material B and forming the intermediate and uppermost layers from the material A; as shown in FIG. 3C, by forming the lowermost and intermediate layers from the material A and forming the uppermost layer form the material B; or, as shown in FIG. 3D, by forming the lowermost layer from a material C that is different from the materials A and B, forming the intermediate layer from the material B, and forming the uppermost layer from the material A.

Figure 4:
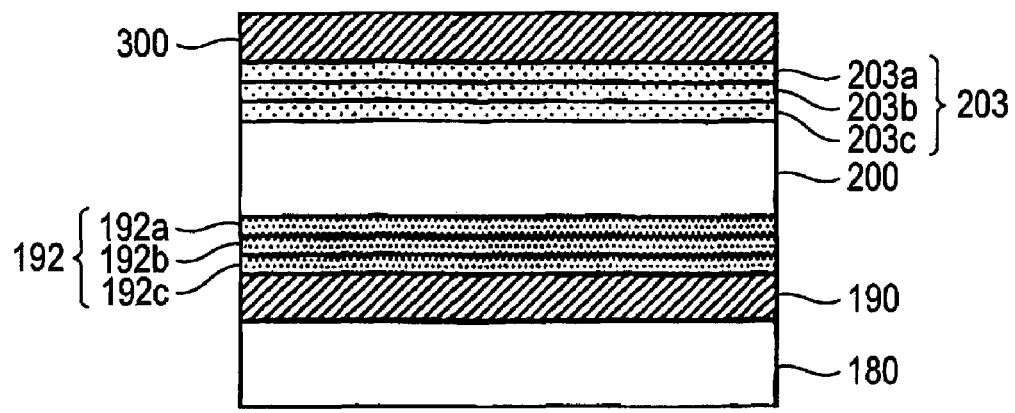
FIG. 4 is a schematic cross-sectional view of the photoelectric conversion layer having an electron-blocking layer in a three-layer structure and a hole-blocking layer in a three-layer structure.
Figure 5:
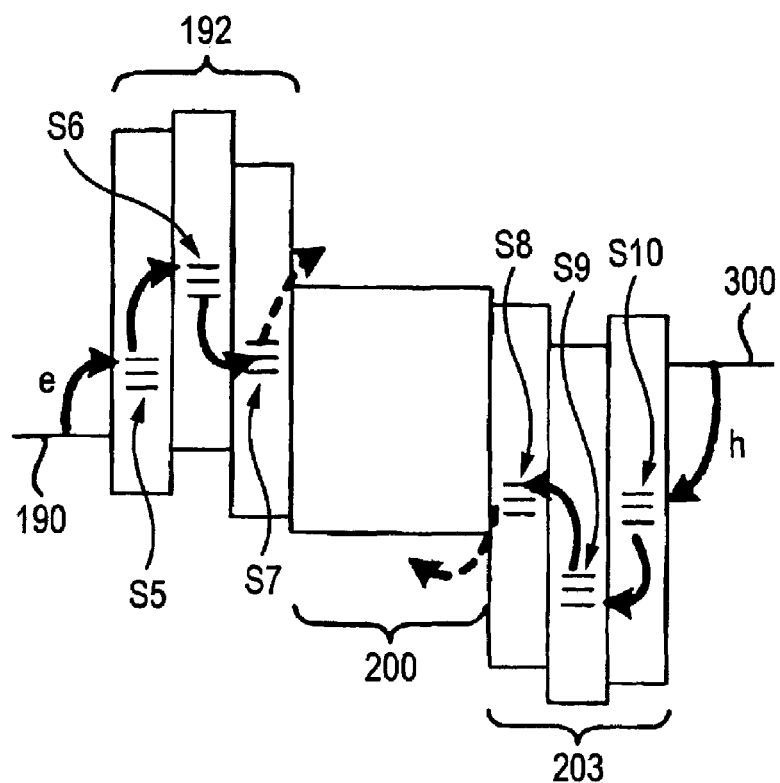
FIG. 5 is an energy diagram for explaining how the carrier is transported through intermediate levels in the charge-blocking layer when a voltage is applied to the photoelectric conversion element of FIG. 4.

FIG. 4 is a schematic cross-sectional view showing another example of the photoelectric conversion element according to this embodiment (a photoelectric conversion element having an electron-blocking layer with a three-layer structure and a hole-blocking layer with a three-layer structure). FIG. 5 is an energy diagram for explaining the state of charge transport via intermediate levels in the electron-blocking layer and the hole-blocking layer when a voltage is applied to the photoelectric conversion element shown in FIG. 4.

The photoelectric conversion element shown in FIG. 4 has a structure where a pixel electrode (transparent electrode) 190 is provided on a transparent substrate 180, an electron-blocking layer 192 with a three-layer structure (with a structure of layers 192a to 192c being stacked), a photoelectric conversion layer 200 and a hole-blocking layer 203 (with a structure of layers 203a to 203c being stacked) are stacked in this order on the transparent electrode 190, and a counter electrode 300 is further provided thereon. Out of the layers 192a to 192c, at least two layers are formed of different materials. Here, materials of the layers 192a to 192c are set to be different from each other. Similarly, out of the layers 203a to 203c, at least two layers are formed of different materials. Here, materials of the layers 203a to 203c are set to be different from each other.

By virtue of such a construction, as shown in FIG. 5, the intermediate levels (S5, S6 and S7) of respective layers in the electron-blocking layer 192 differ in the energy level at the application of a voltage, and a step height therebetween works as an energy barrier, as a result, an electron becomes difficult to be transported. Similarly, the intermediate levels (S8, S9 and S10) of respective layers in the hole-blocking layer 203 differ in the energy level, and a step height therebetween works as an energy barrier, as a result, a hole becomes difficult to be transported.

With respect to stacking of a plurality of layers for the blocking layer, the effects except for the contents regarding the intermediate level are described below.

The above-described technique of shifting intermediate levels present in respective layers by stacking the layers enables suppressing the dark current by "inhibiting transport of the injected charge", but formation of a plurality of layers for the blocking layer also has an effect of reducing the dark current by "suppressing injection of an electric charge from an electrode".

For suppressing the injection of an electric charge from an electrode, it is important "to make large the energy barrier between the electrode and a layer adjacent thereto" and "to homogenize the blocking layer and prevent the electrode from coming into proximity to a layer below the blocking layer (a photoelectric conversion layer)".

The former is an approach of creating an energetic injection barrier, and the latter is an approach of, in view of a physical structure, preventing an electrode material from intruding into a fine defect of the film to allow proximity between the photoelectric conversion layer and the electrode and form a leak site.

When a structure composed of a plurality of layers is formed for the blocking layer, a layer adjoining an electrode out of the plurality of layers can be set to have an energy barrier difference between the layer and the electrode, and a layer not adjoining the electrode can be set as a uniform layer having charge transport property to prevent creation of a leak site. In this way, the functions can be divided and allocated to respective layers.

Based on this viewpoint, the present inventors have found that when an inorganic material layer composed of an inorganic material is used as a blocking layer adjoining an electrode and an organic material layer composed of an organic material is used as an underlying blocking layer (between the inorganic material layer and the photoelectric conversion layer), the dark current can be more markedly suppressed and at the same time, reading out of a signal charge cannot be inhibited.

More specifically, it has been found that when in FIG. 1, the layer 202a is formed as an inorganic material layer and the layer 202b is formed as an organic material layer, when in FIGS. 3B and 3D, A is formed as an inorganic material layer and B is formed as an organic material layer, when in FIGS. 3C, B is formed as an inorganic material layer and A is formed as an organic material layer, or when in FIG. 4, layers 192c and 203a are formed as inorganic material layers and layers 192a, 192b, 203b and 203c are formed as organic material layers, the dark current is more markedly suppressed and at the same time, reading out of a signal charge is not inhibited.

As for the inorganic material constituting the inorganic material layer, it is preferred to use any of Si, Mo, Ce, Li, Hf, Ta, Al, Ti, Zn, W and Zr. Also, an oxide is preferably used as the inorganic material. As for the oxide, use of SiO is particularly preferred.

The inorganic material layer needs to have such an ionization energy Ip as to generate an energy barrier to the work function of an adjacent electrode so as to prevent injection of an electric charge from the electrode, and greater Ip is preferred. However, when the charge-blocking layer is composed of this inorganic material layer alone, if the layer thickness is small, a leak site is produced between the electrode and the photoelectric conversion layer and an effect of preventing injection is not sufficiently obtained, whereas if the layer thickness is large, charge transport property is decreased and a signal charge can be hardly read out.

Therefore, it is important to additionally provide an organic material layer as an underlying layer of the inorganic material layer. The organic material layer is a uniform layer having charge transport property high enough to transport a signal charge generated in the photoelectric conversion layer and is preferably formed of a material with less carriers giving rise to a dark current produced from the material.

By employing such a construction, a uniform and thick blocking layer can be obtained without increasing the dark current derived from the blocking layer and decreasing the photoelectric conversion efficiency, and the dark current can be suppressed by the combinational effect with the inorganic material layer.

The candidate for the organic material constituting the hole-blocking layer and electron-blocking layer is described below.

(Hole-Blocking Layer)

For the hole-blocking layer, an electron-accepting organic material can be used.

Examples of the electron-accepting material which can be used include an oxadiazole derivative such as 1,3-bis(4-tert-butylphenyl-1,3,4-oxadiazolyl)phenylene (OXD-7); an anthraquinodimethane derivative; a diphenylquinone derivative; a bathocuproine, a bathophenanthroline and a derivative thereof; a triazole compound; a tris(8-hydroxyquinolinato) aluminum complex; a bis(4-methyl-8-quinolinato)aluminum complex; a distyrylarylene derivative; and a silole compound. Also, a material having sufficient electron transport property may be used even if it is not an electron-accepting organic material. That is, a porphyrin-based compound, a styryl-based compound such as DCM (4-dicyanomethylene-2-methyl-6-(4-(dimethylaminostyryl))-4H pyran), and a 4H pyran-based compound can be used.

The thickness of the hole-blocking layer is preferably from 10 to 200 nm, more preferably from 30 to 150 nm, still more preferably from 50 to 100 nm, because if this thickness is too small, the effect of suppressing a dark current is decreased, whereas if it is excessively large, the photoelectric conversion efficiency is reduced.

Specific examples of the candidate for the hole-blocking material include the materials indicated by HB-1 to HB-5 and BCP below. In the following, Ea (eV) stands for the electron affinity of the material, and Ip (eV) stands for the ionization potential of the material.

HB-1:

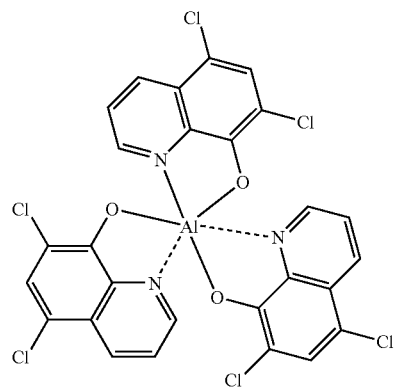

Ea = 3.5, Ip = 6.2

HB-2:

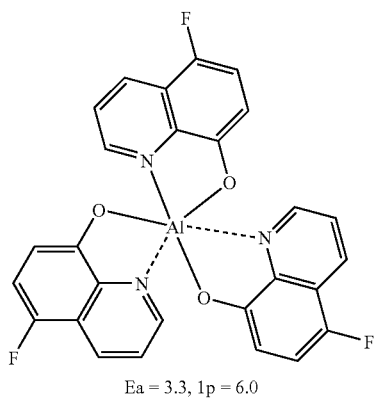

Ea = 3.3, 1p = 6.0

HB-3:

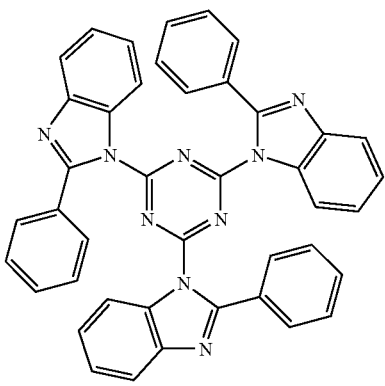

Ea = 3.7, 1p = 7.2

HB-4:

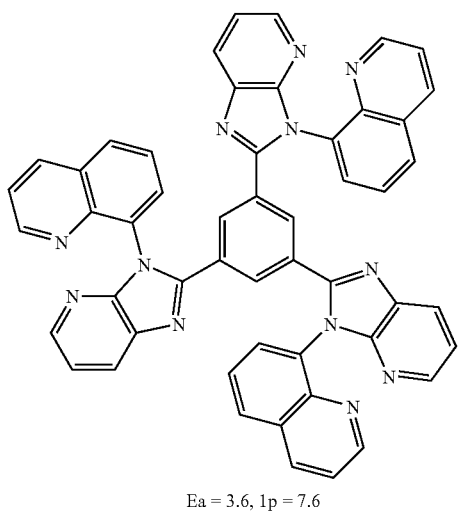

Ea = 3.6, 1p = 7.6

HB-5:

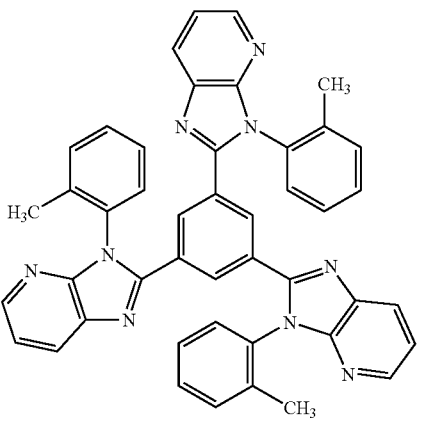

Ea = 3.6, 1p = 7.6

BCP:

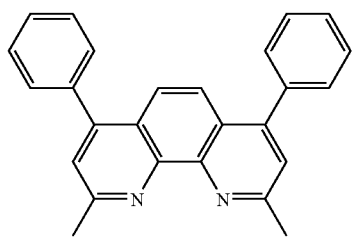

Ea = 3.2, 1p = 6.7

The latitude in selection of the material practically used for the hole-blocking layer is defined by the material of the adjacent electrode and the material of the adjacent photoelectric conversion layer. Those having an ionization potential (Ip) greater than the work function (Wf) of the material of the adjacent electrode by 1.3 eV or more and having an electron affinity (Ea) equal to or greater than Ea of the material of the adjacent photoelectric conversion layer are preferred.

(Electron-Blocking Layer)

For the electron-blocking layer, an electron-donating organic material can be used. Specifically, examples of the low molecular material which can be used include an aromatic diamine compound such as N,N'-bis(3-methylphenyl)-(1,1'-biphenyl)-4,4'-diamine (TPD) and 4,4'-bis[N-(naphthyl)-N-phenylamino]biphenyl (α-NPD), oxazole, oxadiazole, triazole, imidazole, imidazolone, a stilbene derivative, a pyrazoline derivative, tetrahydroimidazole, a polyarylalkane, butadiene, 4,4',4''-tris(N-(3-methylphenyl) N-phenylamino)triphenylamine (m-MTDATA), a porphyrin compound such as porphin, copper tetraphenylporphin, phthalocyanine, copper phthalocyanine and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an anilamine derivative, an amino-substituted chalcone derivative, an oxazole derivative, a styrylanthracene derivative, a fluorenone derivative, a hydrazone derivative, and a silazane derivative. As for the polymer material, a polymer such as phenylenevinylene, fluorene, carbazole, indole, pyrene, pyrrole, picoline, thiophene, acetylene and diacetylene, or a derivative thereof may be used. A compound having a sufficient hole transport property may be used even if it is not an electron-donating compound.

The thickness of the electron-blocking layer is preferably from 10 to 200 nm, more preferably from 30 to 150 nm, still more preferably from 50 to 100 nm, because if this thickness is too small, the effect of suppressing a dark current is decreased, whereas if it is excessively large, the photoelectric conversion efficiency is reduced.

Specific examples of the candidate for the electron-blocking material include the materials indicated by EB-1 to EB-5, TPD and m-MTDATA below.

EB-1:

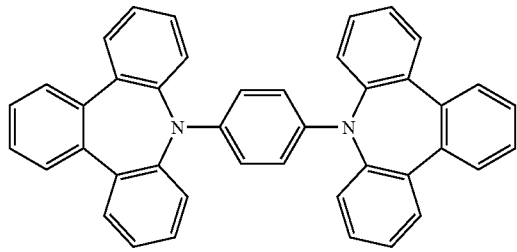

Ea = 1.9, Ip = 4.9

EB-2:

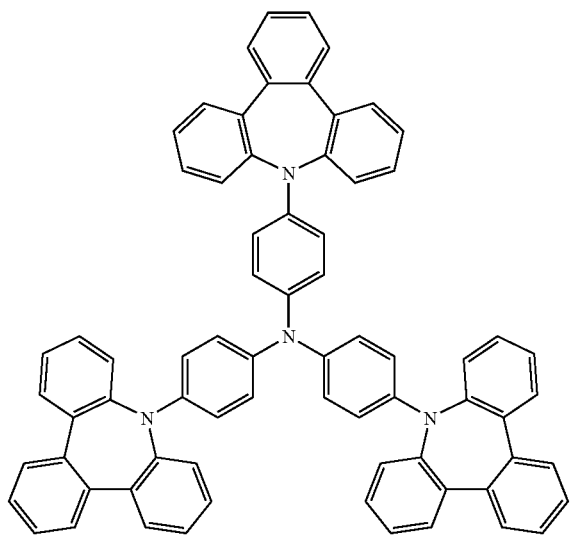

Ea = 1.7, Ip = 4.7

EB-3:

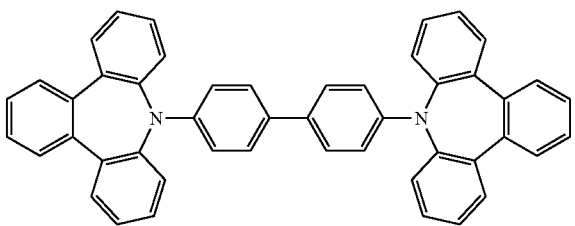

Ea = 1.9, Ip = 5.2

EB-4:

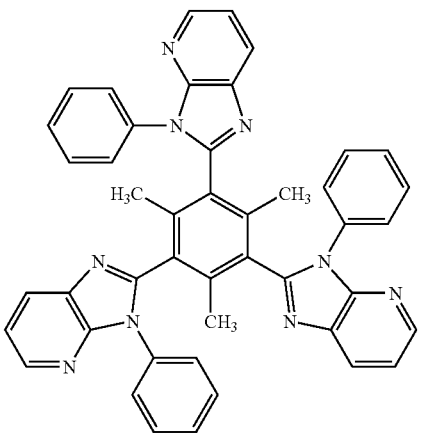

Ea = 2.1, Ip = 5.4

EB-5:

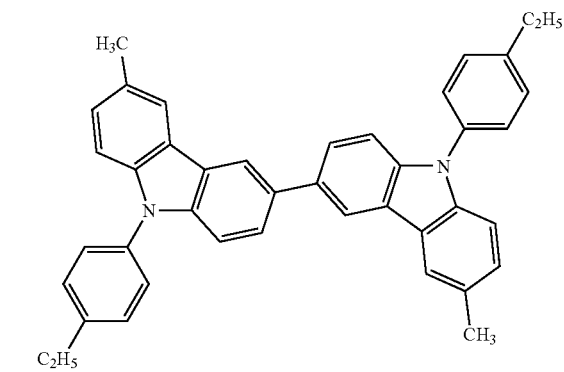

Ea = 2.1, Ip = 5.8

TPD:

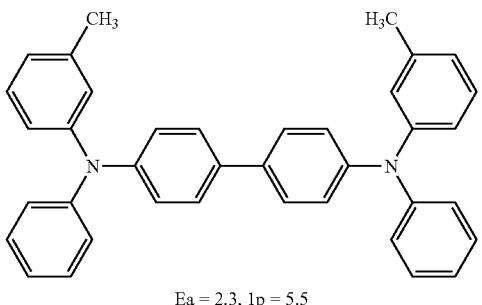

Ea = 2.3, Ip = 5.5 m-MTDATA:

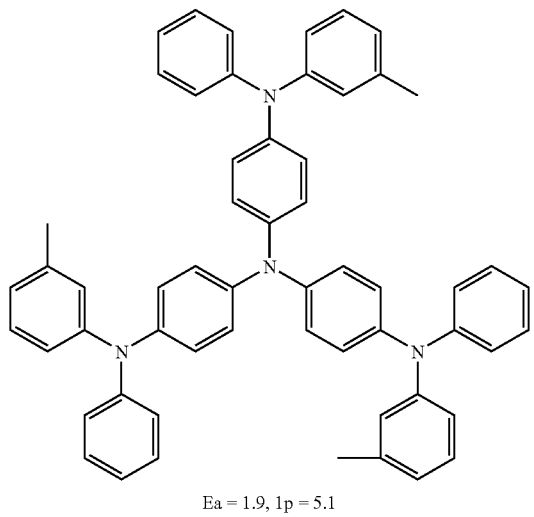

Ea = 1.9, Ip = 5.1

The latitude in selection of the material practically used in the electron-blocking layer is defined by the material of the adjacent electrode and the material of the adjacent photoelectric conversion layer. Those having an electron affinity (Ea) greater than the work function (Wf) of the material of the adjacent electrode by 1.3 eV or more and having an ionization potential (Ip) equal to or smaller than Ip of the material of the adjacent photoelectric conversion layer are preferred.

According to this embodiment, the charge-blocking layer is formed to have a multiple-layer structure without forming a conventionally employed single-layer charge-blocking layer, so that injection of a carrier into the photoelectric conversion layer from the electrode when applying an external electric field can be suppressed and the photocurrent/dark current ratio of the photoelectric conversion element can be greatly enhanced.

(Second Embodiment)

In this embodiment, a photoelectric conversion element having a charge-blocking layer with a multiple-layer structure is specifically described by referring to FIGS. 6 to 11.

The charge-blocking layer includes "a hole-blocking layer" working as a high barrier to the injection of a hole from the adjacent electrode and exhibiting a high transport ability for an electron that is a photocurrent carrier, and "an electron-blocking layer" working as a high barrier to the injection of an electron from the adjacent electrode and exhibiting a high transport ability for a hole that is a photocurrent carrier. In an organic luminescence device and the like, as described in JP-A-11-339966 and JP-A-2002-329582, a blocking layer using an organic material is already employed for preventing a carrier from penetrating through a light-emitting layer, but when such an organic blocking layer is inserted between an electrode and a photoelectric conversion layer in a photoelectric conversion part, the photoelectric conversion efficiency or response speed can be enhanced without incurring reduction in the S/N ratio when an external voltage is applied.

As for the material used in the hole-blocking layer, those having an ionization potential not less than the work function of the material of the adjacent electrode and having an electron affinity not less than the electron affinity of the material of the adjacent photoelectric conversion layer are used. As for the material used in the electron-blocking layer, those having an electron affinity not more than the work function of the material of the adjacent electrode and having an ionization potential not more than the ionization potential of the material of the adjacent photoelectric conversion layer are used. Specific examples thereof are the same as those described in the first embodiment.

The structure of the photoelectric conversion element having a photoelectric conversion part containing such a charge-blocking layer is specifically described below.

First, the construction having a hole-blocking layer is described.

Figure 6:
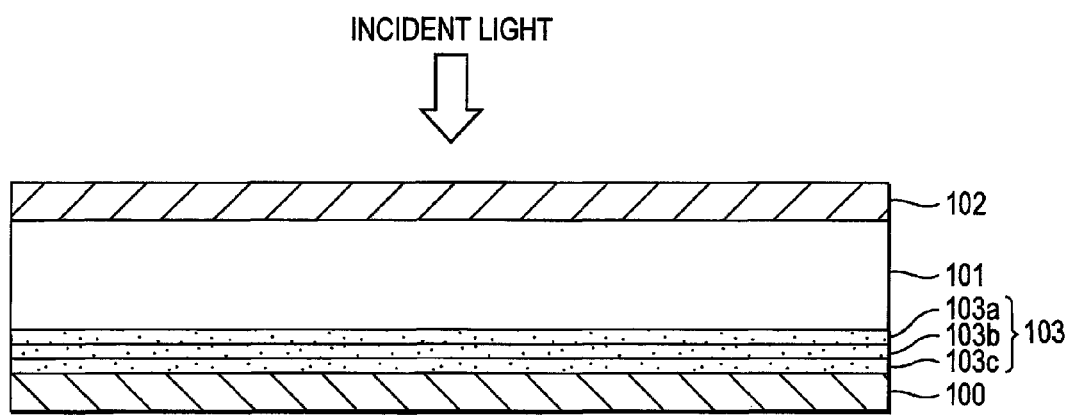
FIG. 6 is a schematic cross-sectional view showing a rough construction of the photoelectric conversion element of this exemplary embodiment.

FIG. 6 is a schematic cross-sectional view showing a rough construction of the photoelectric conversion element of this embodiment.

The photoelectric conversion element shown in FIG. 6 has a construction containing a photoelectric conversion part that comprises a pair of opposing electrodes 100 and 102, a photoelectric conversion layer 101 composed of an organic material and formed between the electrode 100 and the electrode 102, and a hole-blocking layer 103 formed between the photoelectric conversion layer 101 and the electrode 100.

As shown in the Figure, the hole-blocking layer 103 has a three-layer structure in which material layers 103a to 103c are stacked one on another. As described above, at least two layers out of the material layers 103a to 103c are preferably formed of different materials from each other. The hole-blocking layer 103 is sufficient if it has a multiple-layer structure.

In the photoelectric conversion element shown in FIG. 6, light becomes incident from above the electrode 102 and therefore, the electrode 102 serves as the electrode on the light incident side. Also, in the photoelectric conversion element shown in FIG. 6, a voltage is applied to the electrodes 100 and 102 so that out of electric charges (hole and electron) generated in the photoelectric conversion layer 101, a hole can be transported to the electrode 102 and an electron can be transported to the electrode 100 (that is, the electrode 100 can serve as the electrode for collecting electrons).

As for the material of the hole-blocking layer 103, those having an ionization potential not less than the work function of the material of the adjacent electrode 100 and having an electron affinity not less than the electron affinity of the material of the adjacent photoelectric conversion layer 101 are used. By providing this hole-blocking layer 103 between the electrode 100 and the photoelectric conversion layer 101, when a voltage is applied to the electrodes 100 and 102, an electron generated in the photoelectric conversion layer 101 can be transported to the electrode 100 and at the same time, injection of a hole into the photoelectric conversion layer 101 from the electrode 100 can be suppressed. In addition, by virtue of the three-layer structure of the hole-blocking layer 103, the effect of suppressing the injection of a hole from the electrode 100 into the photoelectric conversion layer 101 via intermediate levels is enhanced.

The entire thickness of the hole-blocking layer 103 is most preferably from 10 to 200 nm, because an electron generated in the photoelectric conversion layer 101 must be transported to the electrode 100 and if the thickness above is excessively large, the external quantum efficiency decreases, though the blocking property may be enhanced.

Also, the value obtained by dividing the voltage externally applied to the electrodes 100 and 102 by the sum total of the thickness of the hole-blocking layer 103 and the thickness of the photoelectric conversion layer 101 (corresponding to the distance between the electrode 100 and the electrode 102) is preferably from $10 \times 10^5$ to $10 \times 10^7$ V/cm.

Furthermore, in the photoelectric conversion element shown in FIG. 6, light needs to be incident into the photoelectric conversion layer 101 and therefore, the electrode 102 is preferably a transparent electrode. The term "transparent" as used herein means to transmit 80% or more of visible light at a wavelength of about 420 to about 660 nm.

In the photoelectric conversion element shown in FIG. 6, as described later, light needs to be transmitted to under the electrode 100 in some cases. Therefore, the electrode 100 is also preferably a transparent electrode and the hole-blocking layer 103 is also preferably transparent.

Figure 7:
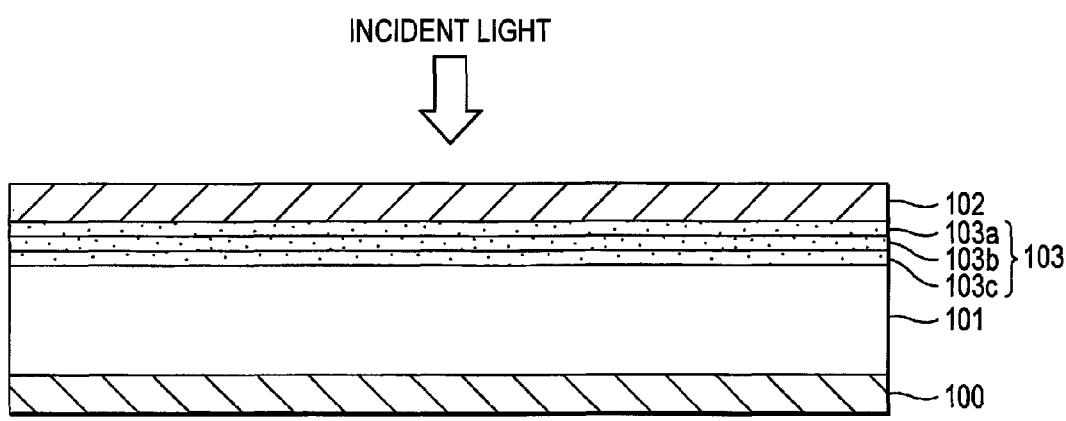
FIG. 7 is a schematic cross-sectional view showing a modified example of the photoelectric conversion element having a structure shown in FIG. 6.

FIG. 7 is a schematic cross-sectional view showing a modified example of the photoelectric conversion element shown in FIG. 6. In the photoelectric conversion element shown in FIG. 6, in the case of applying a voltage to the electrodes 100 and 102 so that out of electric charges (hole and electron) generated in the photoelectric conversion layer 101, an electron can be transported to the electrode 102 and a hole can be transported to the electrode 100 (that is, when the electrode 102 is used as the electrode for collecting electrons), this may be attained by taking a construction where as shown in FIG. 7, a hole-blocking layer 103 (having a three-layer structure in which material layers 103a to 103c are stacked) is provided between the electrode 102 and the photoelectric conversion layer 101. In this case, the hole-blocking layer 103 needs to be transparent. Such a construction enables suppressing dark current.

Incidentally, by taking a construction where an inorganic material layer is disposed at the interface with an electrode and an organic material layer is disposed between the inorganic material layer and the photoelectric conversion layer, for example, a construction where in FIG. 6, the material layer 103c is a layer composed of an inorganic material and the material layers 103a and 103b are a layer composed of an organic material or where in FIG. 7, the material layer 103a is a layer composed of an inorganic material and the material layers 103b and 103c are a layer composed of an organic material, as described above, the dark current can be more markedly suppressed and at the same time, reading out of a signal charge can be prevented from being inhibited.

Next, the construction having an electron-blocking layer is described.

Figure 8:
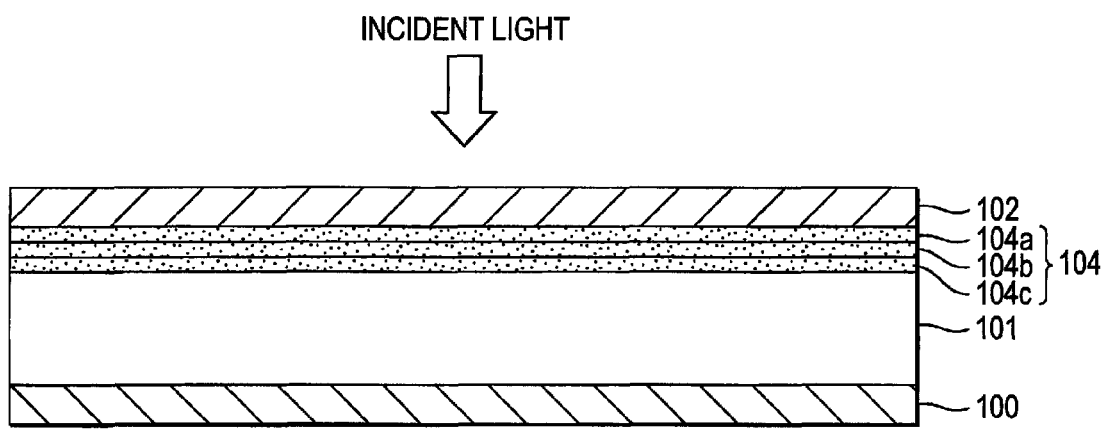
FIG. 8 is a schematic cross-sectional view showing a rough construction of another example of the photoelectric conversion element of this exemplary embodiment.

FIG. 8 is a schematic cross-sectional view showing a rough construction of another example (an example having an electron-blocking layer) of the photoelectric conversion element of this embodiment. In FIG. 8, the same constituents as in FIG. 6 are indicated by like numerical references.

The photoelectric conversion element shown in FIG. 8 has a construction containing a photoelectric conversion part that comprises a pair of opposing electrodes 100 and 102, a photoelectric conversion layer 101 formed between the electrode 100 and the electrode 102, and an electron-blocking layer 104 (having a three-layer structure in which material layers 104a to 104c are stacked) formed between the photoelectric conversion layer 101 and the electrode 102. As described above, at least two layers out of the material layers 104a to 104c are preferably composed of different materials. The electron-blocking layer 104 is sufficient if it has a multiple-layer structure.

In the photoelectric conversion element shown in FIG. 8, light becomes incident from above the electrode 102 and therefore, the electrode 102 serves as the electrode on the light incident side. Also, in the photoelectric conversion element shown in FIG. 8, a voltage is applied to the electrodes 100 and 102 so that out of electric charges (hole and electron) generated in the photoelectric conversion layer 101, a hole can be transported to the electrode 102 and an electron can be transported to the electrode 100 (that is, the electrode 100 is used as the electrode for collecting electrons).

As for the material of the electron-blocking layer 104, those having an electron affinity not more than the work function of the material of the adjacent electrode 102 and having an ionization potential not more than the ionization potential of the material of the adjacent photoelectric conversion layer 101 are used. By providing this electron-blocking layer 104 between the electrode 102 and the photoelectric conversion layer 101, when a voltage is applied to the electrodes 100 and 102, a hole generated in the photoelectric conversion layer 101 can be transported to the electrode 102 and at the same time, injection of an electron into the photoelectric conversion layer 101 from the electrode 102 can be prevented.

The thickness of the electron-blocking layer 104 is most preferably from 10 to 200 nm, because a hole generated in the photoelectric conversion layer 101 must be transported to the electrode 102 and if the thickness above is excessively large, the external quantum efficiency decreases, though the blocking property may be enhanced.

Also, the value obtained by dividing the voltage externally applied to the electrodes 100 and 102 by the sum total of the thickness of the electron-blocking layer 104 and the thickness of the photoelectric conversion layer 101 (corresponding to the distance between the electrode 100 and the electrode 102) is preferably from $10 \times 10^5$ to $10 \times 10^7$ V/cm.

Furthermore, in the photoelectric conversion element shown in FIG. 8, light needs to be incident into the photoelectric conversion layer 101 and therefore, the electrode 102 and the electron-blocking layer 104 are preferably transparent.

In the photoelectric conversion element shown in FIG. 8, as described later, light needs to be transmitted to under the electrode 100 in some cases. Therefore, the electrode 100 is also preferably a transparent electrode.

Figure 9:
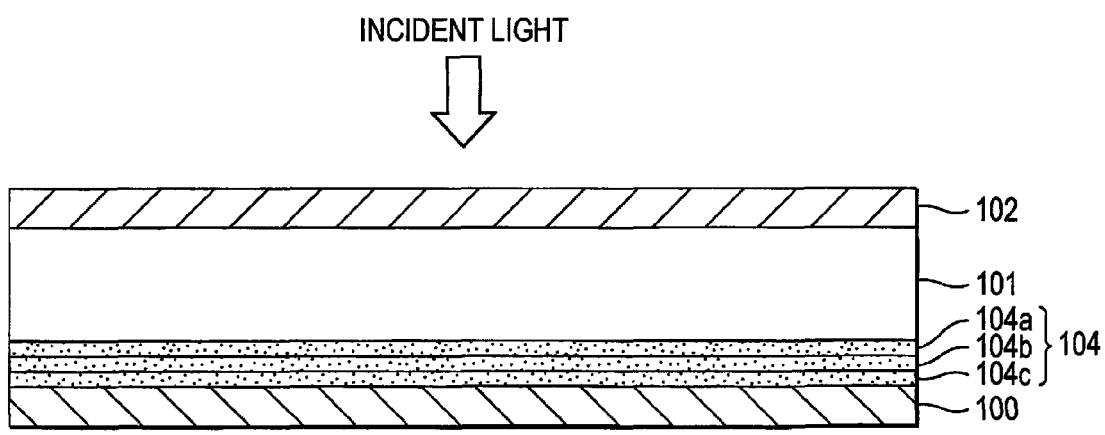
FIG. 9 is a schematic cross-sectional view showing a modified example of the photoelectric conversion element shown in FIG. 8.

FIG. 9 is a schematic cross-sectional view showing a modified example of the photoelectric conversion element having a structure shown in FIG. 8. In the photoelectric conversion element shown in FIG. 8, in the case of applying a voltage to the electrodes 100 and 102 so that out of electric charges (hole and electron) generated in the photoelectric conversion layer 101, an electron can be transported to the electrode 102 and a hole can be transported to the electrode 100 (that is, when the electrode 102 is used as the electrode for collecting electrons), this may be attained by taking a construction where as shown in FIG. 9, an electron-blocking layer 104 is provided between the electrode 100 and the photoelectric conversion layer 101. Such a construction enables suppressing dark current.

Incidentally, by taking a construction where an inorganic material layer is disposed at the interface with an electrode and an organic material layer is disposed between the inorganic material layer and the photoelectric conversion layer, for example, a construction where in FIG. 8, the material layer 104a is a layer composed of an inorganic material and the material layers 104b and 104c are a layer composed of an organic material or where in FIG. 9, the material layer 104c is a layer composed of an inorganic material and the material layers 104a and 104b are a layer composed of an organic material, as described above, the dark current can be more markedly suppressed and at the same time, reading out of a signal charge can be prevented from being inhibited.

The construction having an electron-blocking layer and a hole-blocking layer is described below.

Figure 10:
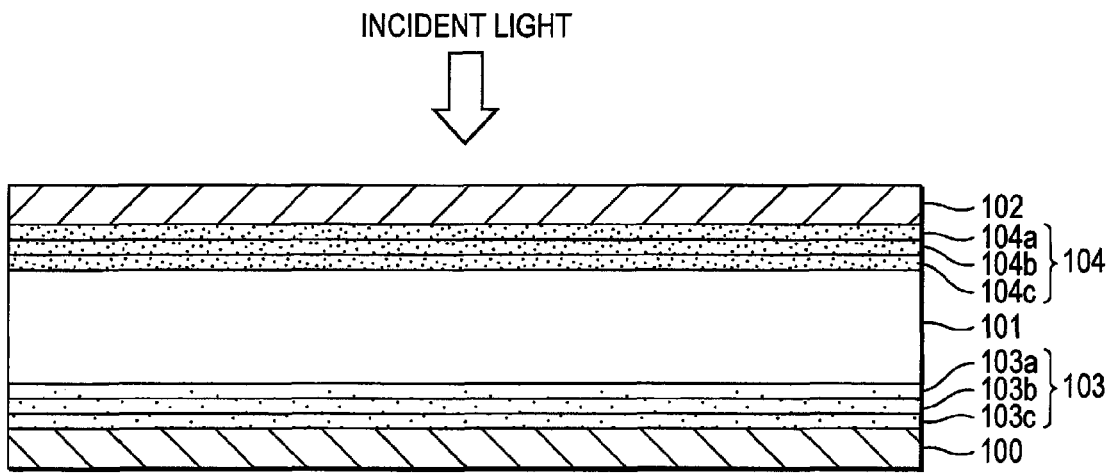
FIG. 10 is a schematic cross-sectional view showing a rough construction of another example of the photoelectric conversion element of this exemplary embodiment.

FIG. 10 is a schematic cross-sectional view showing a rough construction of another example of the photoelectric conversion element (an example having a photoelectric conversion part containing both an electron-blocking layer and a hole-blocking layer) of this embodiment. In FIG. 10, the same constituents as in FIGS. 6 and 8 are indicated by like numerical references.

The photoelectric conversion element shown in FIG. 10 has a construction containing a photoelectric conversion part which comprises a pair of opposing electrodes 100 and 102, a photoelectric conversion layer 101 formed between the electrode 100 and the electrode 102, a hole-blocking layer 103 (103a to 103c) formed between the photoelectric conversion layer 101 and the electrode 100, and an electron-blocking layer 104 (104a to 104c) formed between the photoelectric conversion layer 101 and the electrode 102.

In the photoelectric conversion element shown in FIG. 10, light becomes incident from above the electrode 102 and therefore, the electrode 102 serves as the electrode on the light incident side. Also, in the photoelectric conversion element shown in FIG. 10, a voltage is applied to the electrodes 100 and 102 so that out of electric charges (hole and electron) generated in the photoelectric conversion layer 101, a hole can be transported to the electrode 102 and an electron can be transported to the electrode 100 (that is, the electrode 100 is used as the electrode for collecting electrons).

Furthermore, the value obtained by dividing the voltage externally applied to the electrodes 100 and 102 by the sum total of the thickness of the hole-blocking layer 103, the thickness of the electron-blocking layer 104 and the thickness of the photoelectric conversion layer 101 (corresponding to the distance between the electrode 100 and the electrode 102) is preferably from $1.0\times10^5$ to $1.0\times10^7$ V/cm.

Such a construction enables suppressing injection of an electric charge from both the electrodes 100 and 102 and effectively suppressing the dark current.

Figure 11:
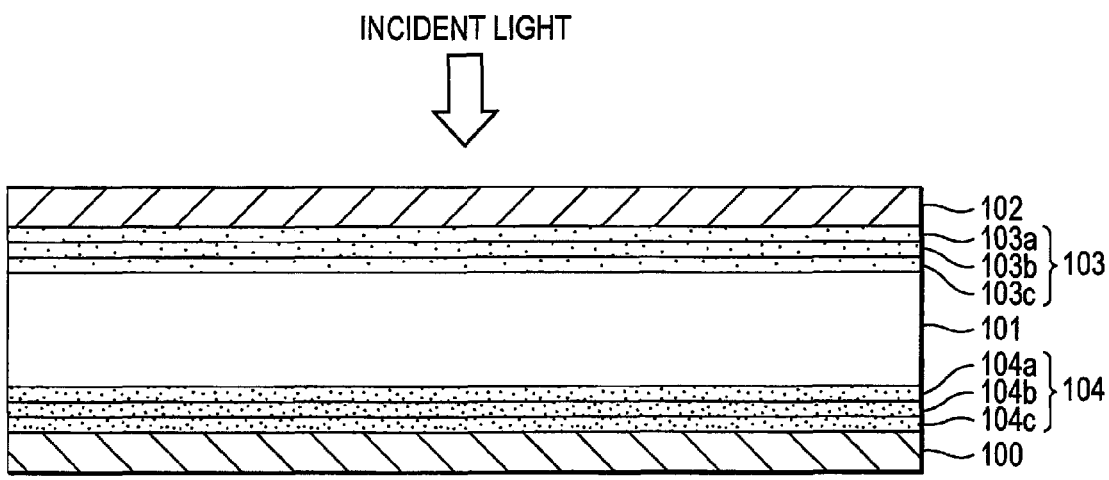
FIG. 11 is a schematic cross-sectional view showing a modified example of the photoelectric conversion element shown in FIG. 10.

FIG. 11 is a schematic cross-sectional view showing a modified example of the photoelectric conversion element shown in FIG. 10.

In the photoelectric conversion element shown in FIG. 10, in the case of applying a voltage to the electrodes 100 and 102 so that out of electric charges (hole and electron) generated in the photoelectric conversion layer 101, an electron can be transported to the electrode 102 and a hole can be transported to the electrode 100 (that is, when the electrode 102 is used as the electrode for collecting electrons), this may be attained by taking a construction where as shown in FIG. 11, an electron-blocking layer 104 is provided between the electrode 100 and the photoelectric conversion layer 101 and a hole-blocking layer 103 is provided between the electrode 102 and the photoelectric conversion layer 101.

Such a construction enables suppressing injection of an electric charge from both the electrodes 100 and 102 and effectively suppressing the dark current.

(Third Embodiment)

A construction example of a solid-state image device using the photoelectric conversion element having a structure shown in FIG. 11 is described below. In the following description, FIGS. 12 to 16 are referred to. In each drawing, similarly to the above-described embodiments, both the hole-blocking layer and the electron-blocking layer have a multiple-layer structure. However, in FIGS. 12 to 16, for drawing convenience, each blocking layer is not illustrated in particular as a plurality of separate layers.

Figure 12:
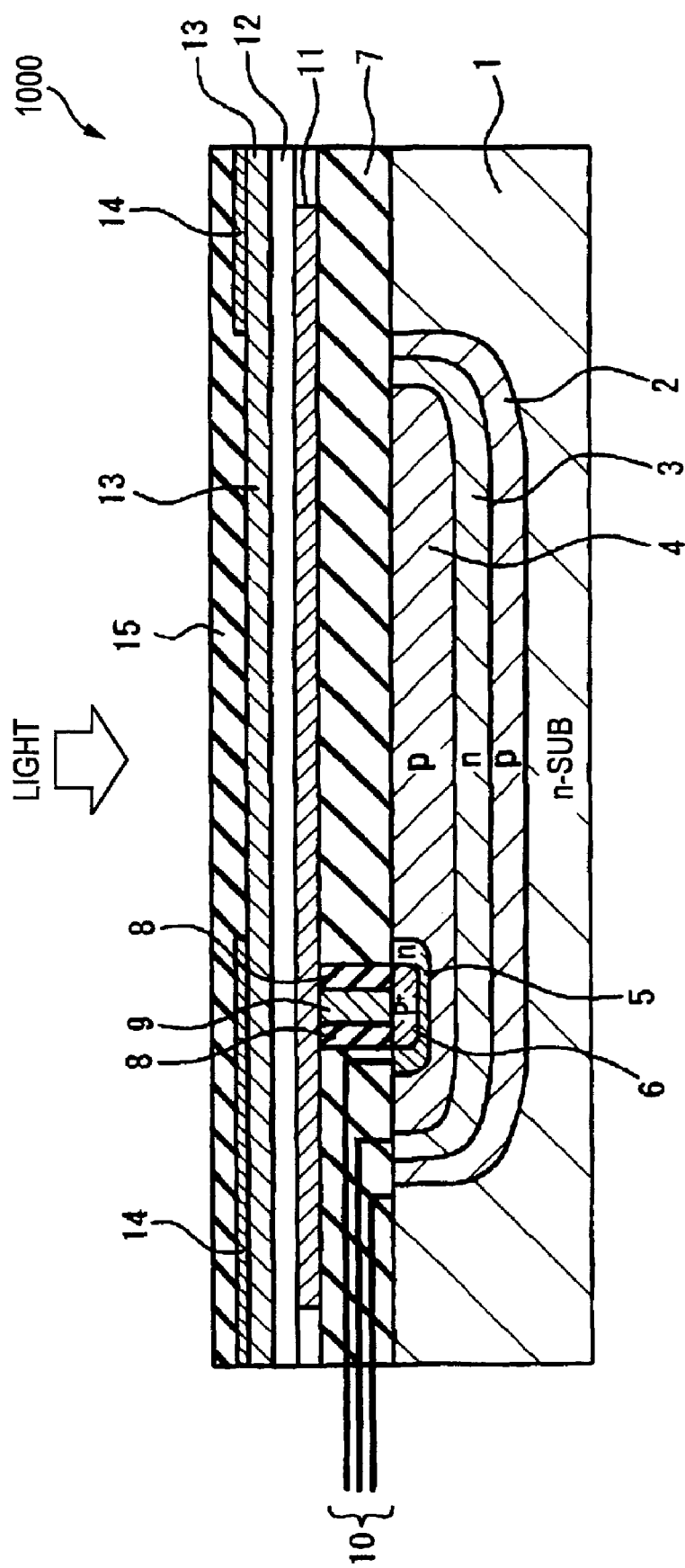
FIG. 12 is a schematic cross-sectional view of one pixel portion of a solid-state image device for explaining the third exemplary embodiment of the present invention.
Figure 13:
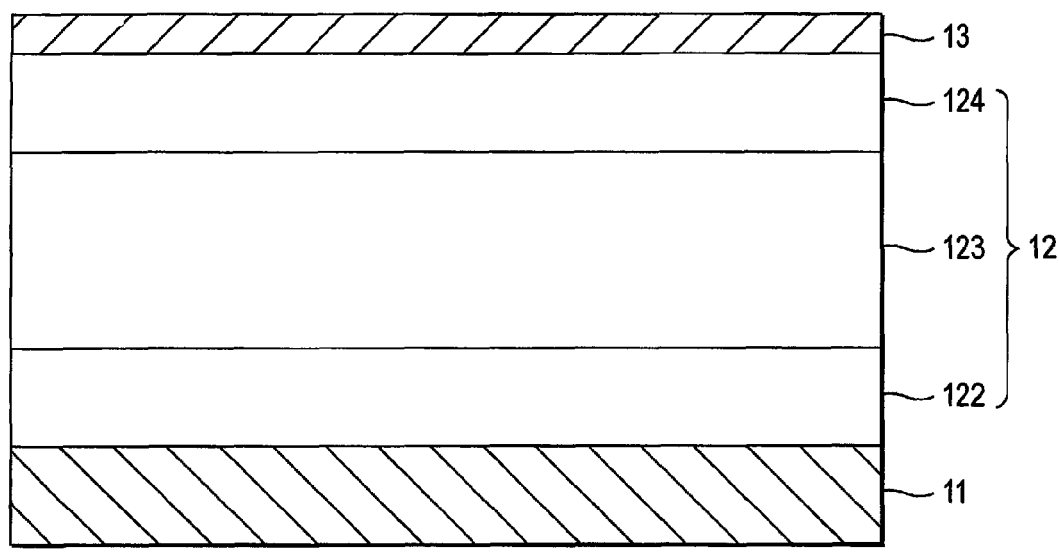
FIG. 13 is a schematic cross-sectional view of the intermediate layer shown in FIG. 12.

FIG. 12 is a schematic cross-sectional view of one pixel portion of a solid-state image device for explaining the third embodiment of the present invention. FIG. 13 is a schematic cross-sectional view of the intermediate layer shown in FIG. 12. In this solid-state image device, a large number of pixels, one of which is shown in FIG. 12, are disposed in an array manner in the same plane, and one-pixel data of the image data can be produced by a signal obtained from this one pixel.

One pixel of the solid-state image device shown in FIG. 12 has a construction containing an n-type silicon substrate 1, a transparent insulating film 7 formed on the n-type silicon substrate 1, and a photoelectric conversion part that comprises a first electrode film 11 formed on the insulating film 7, an intermediate layer 12 formed on the first electrode film 11 and a second electrode film 13 formed on the intermediate layer 12, where a light-shielding film 14 having provided therein an opening is formed on the photoelectric conversion part and the light-receiving region of the intermediate layer 12 is limited by the light-shielding film 14. Also, a transparent insulating film 15 is formed on the light-shielding film 14 and the second electrode film 13. Incidentally, for the photoelectric conversion part formed on the insulating film 7, the construction of the photoelectric conversion element described in the first or second embodiment can be employed.

As shown in FIG. 13, the intermediate layer 12 is constructed by stacking a subbing and electron-blocking layer 122, a photoelectric conversion layer 123 and a hole-blocking and buffering layer 124 in this order on the first electrode film 11. As described in the first or second embodiment, the electron-blocking layer 122 and the hole-blocking and buffering layer 124 each is constructed by a plurality of layers.

The photoelectric conversion layer 123 has a construction containing a material having such properties as to generate electric charges including an electron and a hole in response to light incident from above the second electrode film 13, allow the mobility of electron to be smaller than the mobility of hole, and generate a larger number of electrons and holes in the vicinity of the second electrode film 13 than in the vicinity of the first electrode film 11. An organic material is representative of such a material for the photoelectric conversion film. In the construction of FIG. 12, a material that absorbs green light and generates an electron and a hole in proportion is used for the photoelectric conversion layer 123. The photoelectric conversion layer 123 can be shared in common by all pixels and therefore, this layer may be a film of one-sheet construction and need not be divided for each pixel.

The organic material constituting the photoelectric conversion layer 123 preferably contains at least either an organic p-type semiconductor or an organic n-type semiconductor. For each of the organic p-type semiconductor and the n-type semiconductor, any of a quinacridone derivative, a naphthalene derivative, an anthracene derivative, a phenanthrene derivative, a tetracene derivative, a pyrene derivative, a perylene derivative and a fluoranthene derivative may be preferably used in particular.

The organic p-type semiconductor (compound) is a donor organic semiconductor (compound) and indicates an organic compound having a property of readily donating an electron, mainly typified by a hole-transporting organic compound. More specifically, this is an organic compound having a smaller ionization potential when two organic materials are used in contact. Accordingly, the donor organic compound may be any organic compound as long as it is an electron-donating organic compound. Examples of the compound which can be used include a triarylamine compound, a benzidine compound, a pyrazoline compound, a styrylamine compound, a hydrazone compound, a triphenylmethane compound, a carbazole compound, a polysilane compound, a thiophene compound, a phthalocyanine compound, a cyanine compound, a merocyanine compound, an oxonol compound, a polyamine compound, an indole compound, a pyrrole compound, a pyrazole compound, a polyarylene compound, a condensed aromatic carbocyclic compound (e.g., naphthalene derivative, anthracene derivative, phenanthrene derivative, tetracene derivative, pyrene derivative, perylene derivative, fluoranthene derivative), and a metal complex having a nitrogen-containing heterocyclic compound as a ligand. The donor organic semiconductor is not limited to these compounds and, as described above, any organic compound may be used as long as its ionization potential is smaller than that of the organic compound used as an n-type (acceptor) compound.

The organic n-type semiconductor (compound) is an acceptor organic semiconductor (compound) and indicates an organic compound having a property of readily accepting an electron, mainly typified by an electron-transporting organic compound. More specifically, this is an organic compound having a larger electron affinity when two organic compounds are used in contact. Accordingly, as for the acceptor organic compound, any organic compound can be used as long as it is an electron-accepting organic compound. Examples thereof include a condensed aromatic carbocyclic compound (e.g., naphthalene derivative, anthracene derivative, phenanthrene derivative, tetracene derivative, pyrene derivative, perylene derivative, fluoranthene derivative), a 5- to 7-membered heterocyclic compound containing a nitrogen atom, an oxygen atom or a sulfur atom (e.g., pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine), a polyarylene compound, a fluorene compound, a cyclopentadiene compound, a silyl compound, and a metal complex having a nitrogen-containing heterocyclic compound as a ligand. The acceptor organic semiconductor is not limited to these compounds and, as described above, any organic compound may be used as long as its electron affinity is larger than the organic compound used as the donor organic compound.

As for the p-type organic dye or n-type organic dye, any dye may be used, but preferred examples thereof include a cyanine dye, a styryl dye, a hemicyanine dye, a merocyanine dyes (including zero-methine merocyanine (simple merocyanine)), a trinuclear merocyanine dye, a tetranuclear merocyanine dye, a rhodacyanine dye, a complex cyanine dye, a complex merocyanine dye, an allopolar dye, an oxonol dye, a hemioxonol dye, a squarylium dye, a croconium dye, an azamethine dye, a coumarin dye, an arylidene dye, an anthraquinone dye, a triphenylmethane dye, an azo dye, an azomethine dye, a spiro compound, a metallocene dye, a fluorenone dye, a flugide dye, a perylene dye, a phenazine dye, a phenothiazine dye, a quinone dye, an indigo dye, a diphenylmethane dye, a polyene dye, an acridine dye, an acridinone dye, a diphenylamine dye, a quinacridone dye, a quinophthalone dye, a phenoxazine dye, a phthaloperylene dye, a porphyrin dye, a chlorophyll dye, a phthalocyanine dye, a metal complex dye, and a condensed aromatic carbocyclic dye (e.g., naphthalene derivative, anthracene derivative, phenanthrene derivative, tetracene derivative, pyrene derivative, perylene derivative, fluoranthene derivative).

The metal complex compound is described below. The metal complex compound is a metal complex that has a ligand coordinating to a metal and containing at least one nitrogen, oxygen or sulfur atom. The metal ion in the metal complex is not particularly limited but is preferably beryllium ion, magnesium ion, aluminum ion, gallium ion, zinc ion, indium ion or tin ion, more preferably beryllium ion, aluminum ion, gallium ion or zinc ion, still more preferably aluminum ion or zinc ion. As for the ligand contained in the metal complex, various ligands are known, but examples thereof include ligands disclosed in H. Yersin, Photochemistry and Photophysics of Coordination Compounds, Springer-Verlag (1987), and Akio Yamamoto, Yuki Kinzoku Kagaku—Kiso to Oyo—(Organic Metal Chemistry—Foundation and Application—), Shokabo (1982).

The ligand is preferably a nitrogen-containing heterocyclic ligand (preferably having a carbon number of 1 to 30, more preferably from 2 to 20, still more preferably from 3 to 15; which may be a monodentate ligand or a bidentate or higher-dentate ligand and is preferably a bidentate ligand, such as pyridine ligand, bipyridyl ligand, quinolinol ligand, hydroxyphenylazole ligand (e.g., hydroxyphenylbenzimidazole, hydroxyphenylbenzoxazole, hydroxyphenylimidazole)), an alkoxy ligand (preferably having a carbon number of 1 to 30, more preferably from 1 to 20, still more preferably from 1 to 10, such as methoxy, ethoxy, butoxy and 2-ethylhexyloxy), an aryloxy ligand (preferably having a carbon number of 6 to 30, more preferably from 6 to 20, still more preferably from 6 to 12, such as phenyloxy, 1-naphthyloxy, 2-naphthyloxy, 2,4,6-trimethylphenyloxy and 4-biphenyloxy), a heteroaryloxy ligand (preferably having a carbon number of 1 to 30, more preferably from 1 to 20, still more preferably from 1 to 12, such as pyridyloxy, pyrazyloxy, pyrimidyloxy and quinolyloxy), an alkylthio ligand (preferably having a carbon number of 1 to 30, more preferably from 1 to 20, still more preferably from 1 to 12, such as methylthio and ethylthio), an arylthio ligand (preferably having a carbon number of 6 to 30, more preferably from 6 to 20, still more preferably from 6 to 12, such as phenylthio), a heterocyclic ring-substituted thio ligand (preferably having a carbon number of 1 to 30, more preferably from 1 to 20, still more preferably from 1 to 12, such as pyridylthio, 2-benzimizolylthio, 2-benzoxazolylthio and 2-benzothiazolylthio), or a siloxy ligand (preferably having a carbon number of 1 to 30, more preferably from 3 to 25, still more preferably from 6 to 20, such as triphenylsiloxy group, triethoxysiloxy group and triisopropylsiloxy group), more preferably a nitrogen-containing heterocyclic ligand, an aryloxy ligand, a heteroaryloxy group or a siloxy ligand, still more preferably a nitrogen-containing heterocyclic ligand, an aryloxy ligand or a siloxy ligand.

The intermediate layer 12 preferably has a photoelectric conversion layer which has a p-type semiconductor layer and an n-type semiconductor layer, with at least either the p-type semiconductor or the n-type semiconductor being an organic semiconductor, and in which a bulk heterojunction structural layer containing the p-type semiconductor and the n-type conductor is provided between these semiconductor layers. In this case, the bulk heterojunction structure contained in the intermediate layer 12 compensates for a drawback that the carrier diffusion length in the photoelectric conversion layer 123 is short, whereby the photoelectric conversion efficiency of the photoelectric conversion layer 123 can be enhanced. Incidentally, the bulk heterojunction structure is described in detail in JP-A-2005-303266 (Japanese Patent Application No. 2004-080639).

Also, the intermediate layer 12 preferably has a photoelectric conversion layer where the number of repeating structures (tandem structures) by a pn junction layer formed of the p-type semiconductor layer and the n-type semiconductor is 2 or more, more preferably where an electrically conductive material thin layer is inserted between those repeating structures. The number of the repeating structure (tandem structure) by a pn junction layer may be any number but for raising the photoelectric conversion efficiency, is preferably from 2 to 50, more preferably from 2 to 30, still more preferably from 2 to 10. The electrically conductive material is preferably silver or gold, and most preferably silver. The tandem structure is described in detail in JP-A-2005-303266 (Japanese Patent Application No. 2004-079930).

The photoelectric conversion layer contained in the intermediate layer 12 preferably has a p-type semiconductor layer and an n-type semiconductor layer (preferably a mixed and dispersed (bulk heterojunction structure) layer), where at least either the p-type semiconductor or the n-type semiconductor contains an orientation-controlled organic compound, more preferably where both the p-type semiconductor and the n-type semiconductor contain an orientation-controlled (controllable) organic compound. As for this organic compound, those having a conjugated π electron are preferably used, and a π-electron plane aligned at an angle not perpendicular but closer to parallel with respect to the substrate (electrode substrate) is more preferred. The angle with respect to the substrate is preferably from 0 to 80°, more preferably from 0 to 60°, still more preferably from 0 to 40°, yet still more preferably from 0 to 20°, even yet still more preferably from 0 to 10°, and most preferably 0° (that is, parallel to the substrate). Such an orientation-controlled organic compound layer is sufficient if it is contained even as a part of the entire intermediate layer 12, but the ratio of the orientation-controlled portion to the entire intermediate layer 12 is preferably 10% or more, more preferably 30% or more, still more preferably 50% or more, yet still more preferably 70% or more, even yet still more preferably 90% or more, and most preferably 100%. The controlled orientation of the organic compound contained in the intermediate layer 12 compensates for a drawback that the carrier diffusion length in the photoelectric conversion layer is short, whereby the photoelectric conversion efficiency of the photoelectric conversion film is enhanced.

In the case where the orientation of the organic compound is controlled, it is more preferred that the heterojunction plane (for example, the pn-junction plane) is not in parallel to the substrate. A heterojunction plane aligned at an angle closer to perpendicular but not in parallel to the substrate (electrode substrate) is more preferred. The angle with respect to the substrate is preferably from 10 to 90°, more preferably from 30 to 90°, still more preferably from 50 to 90°, yet still more preferably from 70 to 90°, even yet still more preferably 80 to 90°, and most preferably 90° (that is, perpendicular to the substrate). Such an organic compound layer with the heterojunction plane being controlled is sufficient if it is contained even as a part of the entire intermediate layer 12. The ratio of the orientation-controlled portion to the entire intermediate layer 12 is preferably 10% or more, more preferably 30% or more, still more preferably 50% or more, yet still more preferably 70% or more, even yet still more preferably 90% or more, and most preferably 100%. In such a case, the area of the heterojunction plane in the intermediate layer 12 and in turn the amount of the carrier produced at the interface, such as electron, hole and electron-hole pair, can be increased and the photoelectric conversion efficiency can be enhanced. The photoelectric conversion efficiency can be enhanced particularly in a photoelectric conversion layer where the alignments of both the heterojunction plane and the π-electron plane of the organic compound are controlled. These conditions are described in detail in JP-A-2006-086493 (Japanese Patent Application No. 2004-079931).

The intermediate layer 12 containing such an organic compound is film-formed by a dry film-forming method or a wet film-forming method. Specific examples of the dry film-forming method include a physical vapor-growth method such as vacuum vapor deposition, sputtering, ion plating and MBE, and a CVD method such as plasma polymerization. As for the wet film-forming method, a cast method, a spin coating method, a dipping method, an LB method and the like may be used.

In the case of using a polymer compound as at least one of the p-type semiconductor (compound) and the n-type semiconductor (compound), the film is preferably formed by a wet film-forming method where a film is easy to produce. In the case of using a dry film-forming method such as vapor deposition, use of a polymer is difficult because of probable occurrence of decomposition, but an oligomer thereof may be preferably used instead. On the other hand, in the case of using a low molecular compound, a dry film-forming method is preferably employed, and a vacuum vapor deposition method is particularly preferred. In the vacuum vapor deposition method, basic parameters are, for example, the method of heating the compound, such as resistance heating vapor deposition or electron beam heating vapor deposition, the shape of the vapor deposition source, such as crucible or boat, the vacuum degree, the vapor deposition temperature, the substrate temperature, and the vapor deposition rate. In order to enable uniform vapor deposition, the vapor deposition is preferably performed while rotating the substrate. The vacuum degree is preferably higher, and the vacuum vapor deposition is performed at $10^{-4}$ Torr or less, preferably $10^{-6}$ Torr or less, more preferably $10^{-8}$ Torr or less. All steps at the vapor deposition are preferably performed in vacuum, and the compound is fundamentally prevented from coming into direct contact with oxygen in the outside air or with water. The above-described conditions in the vacuum vapor deposition affect the crystallinity, amorphous property, density, compactness and the like of the organic film and therefore, must be strictly controlled. The PI or PID control of the vapor deposition rate by using a thickness monitor such as quartz oscillator or interferometer is preferably employed. In the case of simultaneously vapor-depositing two or more kinds of compounds, a co-vapor deposition method, a flash vapor deposition method or the like may be preferably used.

In the photoelectric conversion layer 123 composed of an organic material, when light is incident from above the second electrode 13 in the above-described construction, an electron and a hole, which are generated by light absorption, are generally generated in large number in the vicinity of the second electrode 13 and in not so large number in the vicinity of the first electrode 11. This is ascribable to a phenomenon that light at a wavelength near the absorption peak of the photoelectric conversion layer 123 is mostly absorbed in the vicinity of the second electrode 13 and the light absorptance decreases with distance from the vicinity of the second electrode 13. Accordingly, unless an electron or hole generated in the vicinity of the second electrode 13 is efficiently transported to the silicon substrate, the photoelectric conversion efficiency decreases, as a result, reduction in the sensitivity of the device is incurred. Also, the signal based on the wavelength of light strongly absorbed in the vicinity of the second electrode 13 decreases and this incurs broadening of the width of spectral sensitivity.

In the photoelectric conversion layer 123 composed of an organic material, the electron mobility is generally very smaller than the hole mobility. Furthermore, it is known that the electron mobility in the photoelectric conversion layer 123 composed of an organic material is susceptible to oxygen and when the photoelectric conversion layer 123 is exposed to air, the electron mobility further decreases. Accordingly, in the case of transporting an electron to the silicon substrate 1, if an electron generated in the vicinity of the second electrode 13 travels a long distance in the photoelectric conversion layer 123, a part of electrons are not collected at the electrode due to deactivation or the like during the travel, as a result, the sensitivity decreases and the spectral sensitivity is broadened.

In order to prevent reduction in the sensitivity and broadening of the spectral sensitivity, it is effective to efficiently transport an electron or hole generated in the vicinity of the second electrode 13 to the silicon substrate 1. For realizing this efficient transport, the manner of managing an electron or hole generated in the photoelectric conversion layer 123 becomes important.

The solid-state image device 1000 contains a photoelectric conversion layer 123 having the above-described properties and therefore, as described above, a hole is utilized by collecting it in the first electrode film 11 that is an electrode opposite the electrode on the light incident side, whereby the external quantum efficiency can be raised and enhancement of the sensitivity and sharpening of the spectral sensitivity can be achieved. Accordingly, in the solid-state image device 1000, a voltage is applied to the first electrode film 11 and the second electrode film 13 so that an electron generated in the photoelectric conversion layer 123 can be transported to the second electrode film 13 and a hole generated in the photoelectric conversion layer 123 can be transported to the first electrode film 11.

One function of the subbing and electron-blocking layer 122 is to alleviate irregularities on the first electrode film 11. In the case where irregularities are present on the first electrode film 11 or a dust is attached to the first electrode film 11, when a low molecular organic compound is vapor-deposited thereon to form a photoelectric conversion layer 123, the irregularity portion is liable to allow production of fine cracks in the photoelectric conversion layer 123, that is, areas where the photoelectric conversion layer 123 is formed only as a thin film. At this time, when the second electrode film 13 is further formed thereon, the second electrode film 13 coverages the crack areas and comes into proximity with the first electrode film 11 and DC short or increase of leak current is likely to occur. This tendency is prominent particularly when using TCO as the second electrode film 13. Occurrence of such a trouble can be suppressed by previously providing a subbing and electron-blocking layer 122 on the first electrode film 11 to alleviate the irregularities.

As for the subbing and electron-blocking layer 122, the matter of importance is to be a uniform and smooth film. Particularly, in the case of obtaining a smooth film, the preferred material is an organic polymer material such as polyaniline, polythiophene, polypyrrole, polycarbazole, PTPDES and PTPDEK, and the film may also be formed by a spin coating method.

The electron-blocking layer 122 is provided for reducing a dark current ascribable to injection of an electron from the first electrode film 11 and blocks the injection of an electron into the photoelectric conversion layer 123 from the first electrode film 11.

The hole-blocking and buffering layer 124 is provided for, as a hole-blocking layer, reducing a dark current ascribable to injection of a hole from the second electrode film 13 and fulfills not only a function of blocking the injection of a hole into the photoelectric conversion layer 123 from the second electrode 13 but depending on the case, also a function of lessening a damage imposed on the photoelectric conversion layer 123 during formation of the second electrode film 13.

In the case of forming the second electrode film 13 above the photoelectric conversion layer 123, a high energy particle present in the apparatus used for film formation of the second electrode film 13, such as, in the case of a sputtering method, sputter particle, secondary electron, Ar particle or oxygen anion, may collide against the photoelectric conversion layer 123, and this may cause deterioration of the photoelectric conversion layer 123 and in turn, degradation of the performance, such as increase in leak current or decrease in sensitivity. One preferred method for preventing this deterioration is to provide a buffering film (not shown) above the photoelectric conversion layer 123.

Backing to FIG. 12, inside of the n-type silicon substrate 1, a p-type semiconductor region (hereinafter simply referred to as "p region") 4, an n-type semiconductor region (hereinafter simply referred to as "n region") 3 and a p region 2 are formed in order of increasing the depth. In the p region 4, a high-concentration p region (referred to as a p+ region) 6 is formed in the surface part of the portion light-shielded by the light-shielding film 14, and the p+ region 6 is surrounded by an n region 5.

The depth of the pn junction plane by the p region 4 and the n region 3 from the surface of the n-type silicon substrate 1 is set to a depth at which blue light is absorbed (about 0.2 μm). Therefore, the p region 4 and the n region 3 form a photodiode (B photodiode) where blue light is absorbed and a hole is generated in proportion and accumulated. The hole generated in the B photodiode is accumulated in the p region 4.

The depth of the pn junction face by the p region 2 and the n-type silicon substrate 1 from the surface of the n-type silicon substrate 1 is set to a depth at which red light is absorbed (about 2 μm). Therefore, the p region 2 and the n-type silicon substrate 1 form a photodiode (R photodiode) where red light is absorbed and a hole is generated in proportion and accumulated. The hole generated in the R photodiode is accumulated in the p region 2.

The p+ region 6 is electrically connected to the first electrode film 11 via a connection part 9 formed in the opening bored through the insulating film 7 and in this region, holes collected at the first electrode film 11 are accumulated via the connection part 9. The connection part 9 is electrically insulated by an insulating film 8 from portions except for the first electrode film 11 and the p+ region 6.

The holes accumulated in the p region 2 are converted into signals in proportion to the electric charge amount by an MOS circuit (not shown) comprising a p-channel MOS transistor formed inside of the n-type silicon substrate 1, the holes accumulated in the p region 4 are converted into signals in proportion to the electric charge amount by an MOS circuit (not shown) comprising a p-channel MOS transistor formed inside of the n region 3, the electrons accumulated in the p+ region 6 are converted into signals in proportion to the electric charge amount by an MOS circuit (not shown) comprising a p-channel MOS transistor formed inside of the n region 5, and these signals are output to the outside of the solid-state image device 1000. The MOS circuits above constitute the signal readout part specified in the scope of claim for patent. Each MOS circuit is connected to a signal readout pad (not shown) by a wiring 10. Incidentally, when a collection electrode is provided in the p region 2 and p region 4 and a predetermined reset potential is applied, each region is depleted and the capacity of each pn junction part becomes an infinitely small value, whereby the capacity produced on the junction plane can be made extremely small.

Such a construction enables, for example, photoelectrically converting G light by the photoelectric conversion layer 123 and photoelectrically converting B light and R light by the B photodiode and R photodiode, respectively, in the n-type silicon substrate 1. Also, since G light is first absorbed in the upper part, excellent color separation is obtained between B-G and between G-R. This is greatly advantageous as compared with a solid-state image device of the type where three PDs are stacked inside of the silicon substrate and all of BGR light are separated inside of the silicon substrate. In the following, the portion composed of an inorganic material, which is formed inside of the n-type silicon substrate 1 of the solid-state image device 1000 and in which photoelectric conversion is performed (B photodiode, R photodiode), is sometimes referred to as an inorganic layer.

Incidentally, an inorganic photoelectric conversion part composed of an inorganic material, in which light transmitted through the photoelectric conversion layer 123 is absorbed and an electric charge is generated in proportion to the light and accumulated, may also be formed between the n-type silicon substrate 1 and the first electrode film 11 (for example, between the insulating film 7 and the n-type silicon substrate 1). In this case, an MOS circuit for reading out signals in proportion to electric charges accumulated in a charge accumulation region of the inorganic photoelectric conversion part may be provided inside of the n-type silicon substrate 1 and the wiring 10 may be connected also to this MOS circuit.

The first electrode film 11 fulfills a role of collecting holes transported thereto after generation in the photoelectric conversion layer 123. The first electrode film 11 is divided for each pixel, whereby image data can be produced. In the construction shown in FIG. 12, photoelectric conversion is performed also in the n-type silicon substrate 1 and therefore, the first electrode film 11 preferably has a visible light transmittance of 60% or more, more preferably 90% or more. In the case of a construction where a photoelectric conversion region is not present under the first electrode film 11, the first electrode film 11 may have low transparency. As for the material, any of ITO, IZO, $ZnO_2$, $SnO_2$, $TiO_2$, FTO, Al, Ag and Au may be most preferably used. Details of the first electrode film 11 are described later.

The second electrode film 13 has a function of ejecting an electron transported thereto after generation in the photoelectric conversion layer 123. The second electrode film 13 can be used in common by all pixels. For this reason, in the solid-state image device 1000, the second electrode film 13 is formed as a film of one-sheet construction, which is shared in common among all pixels. For the second electrode film 13, a material having high transparency to visible light needs to be used, because light must be incident into the photoelectric conversion layer 123. The second electrode film 13 preferably has a visible light transmittance of 60% or more, more preferably 90% or more. As for the material, any of ITO, IZO, $ZnO_2$, $SnO_2$, $TiO_2$, FTO, Al, Ag and Au may be most preferably used. Details of the second electrode film 13 are described later.

For the inorganic layer, a pn junction or pin junction of a compound semiconductor such as crystalline silicon, amorphous silicon and GaAs is generally used. In this case, color separation is performed according to the depth to which light intrudes into silicon, and therefore, the spectrum range detected by each of light-receiving parts stacked becomes broad. However, color separation is markedly improved by, as shown in FIG. 13, using the photoelectric conversion layer 123 as an upper layer, that is, allowing the light transmitted through the photoelectric conversion layer 123 to be detected in the depth direction of silicon. In particular, as shown in FIG. 13, when G light is detected in the photoelectric conversion layer 123, light transmitted through the photoelectric conversion layer 123 becomes B light and R light and separation of light in the depth direction of silicon needs to be made only between B light and R light, as a result, color separation is improved. Even in the case of detecting B light or R light in the photoelectric conversion layer 123, color separation can be markedly improved by appropriately selecting the depth of the pn junction plane in silicon.

The construction of the inorganic layer is preferably npn or pnpn from the light incident side. In particular, pnpn junction is more preferred, because by providing a p layer on the surface and making high the surface potential, a hole and a dark current, which are generated in the vicinity of the surface, can be trapped and the dark current can be reduced.

Incidentally, FIG. 12 shows a construction where one layer of the photoelectric conversion part is stacked above the n-type silicon substrate 1, but there may also take a construction where a plurality of layers of the photoelectric conversion part are stacked above the n-type silicon substrate 1. The construction where a plurality of layers are stacked as the photoelectric conversion part is described in later embodiments. In the case of such a construction, light detected in the inorganic layer may be light of only one color, and preferred color separation can be achieved. Also, in the case of detecting lights of four colors by one pixel of the solid-state image device 1000, there may be considered, for example, a construction where one color is detected in one photoelectric conversion part and three colors are detected in the inorganic layer; a construction where two layers of the photoelectric conversion part are stacked to detect two colors and other two colors are detected in the inorganic layer; and a construction where three layers of the photoelectric conversion part are stacked to detect three colors and other one color is detected in the inorganic layer. Furthermore, the solid-state image device 1000 may also take a construction where only one color is detected by one pixel. This is a construction where in FIG. 12, the p region 2, the n region 3 and the p region 4 are eliminated.

The inorganic layer is described in more detail. The preferred construction of the inorganic layer includes a light-receiving device of photoconductive type, p-n junction type, Schottky junction type, PIN junction type or MSM (metal-semiconductor-metal) type, and a phototransistor-type light-receiving device. In particular, it is preferred to use an inorganic layer where as shown in FIG. 12, a plurality of regions of first conductivity type and a plurality of regions of second conductivity type which is a conductivity type opposite the first conductivity type are alternately stacked inside of a single semiconductor substrate and the junction planes by the regions of first conductivity type and second conductivity type are formed at respective depths suitable for photoelectrically converting mainly lights in a plurality of different wavelength bands. The single semiconductor substrate is preferably single-crystal silicon, and color separation can be effected by utilizing the absorption wavelength property dependent on the depth direction of the silicon substrate.

The inorganic semiconductor may also be an InGaN-based, InAlN-based, INAlP-based or InGaAlP-based inorganic semiconductor. The InGaN-based inorganic semiconductor is an inorganic semiconductor adjusted to have a maximum absorption value in the blue wavelength range by appropriately changing the composition of In content. That is, the composition becomes $In_xGa_{1-x}N$ ($0 \leq x \leq 1$). Such a compound semiconductor is produced by using a metal organic chemical vapor deposition method (MOCVD method). The InAlN-based nitride semiconductor using Al which is the same Group 13 raw material as Ga may also be used as a short wavelength light-receiving part, similarly to the InGaN-based semiconductor. Furthermore, InAlP or InGaAlP that lattice-matches with a GaAs substrate may also be used.

The inorganic semiconductor may be of a buried structure. The "buried structure" indicates a construction where both ends of a short wavelength light-receiving part are covered by a semiconductor different from the short wavelength light-receiving part. The semiconductor for covering both ends is preferably a semiconductor having a band gap wavelength shorter than or equal to the band gap wavelength of the short wavelength light-receiving part.

As for the material of the first electrode film 11 and the second electrode film 13, a metal, an alloy, a metal oxide, an electric conducting compound or a mixture thereof may be used. The metal material includes an arbitrary combination of elements selected from Li, Na, Mg, K, Ca, Rb, Sr, Cs, Ba, Fr, Ra, Sc, Ti, Y, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd, Al, Ga, In, Tl, Si, Ge, Sn, Pb, P, As, Sb, Bi, Se, Te, Po, Br, I, At, B, C, N, F, O, S and N. Above all, Al, Pt, W, Au, Ag, Ta, Cu, Cr, Mo, Ti, Ni, Pd and Zn are preferred.

The first electrode film 11 extracts and collects holes from a hole-transporting photoelectric conversion layer or hole transport layer contained in the intermediate layer 12 and therefore, the material is selected by taking into consideration the adherence to adjacent layers such as hole-transporting photoelectric conversion layer and hole transport layer, the electron affinity, the ionization potential, the stability and the like. The second electrode film 13 extracts and ejects electrons from an electron-transporting photoelectric conversion layer or electron transport layer contained in the intermediate layer 12 and therefore, the material is selected by taking into consideration the adherence to adjacent layers such as electron-transporting photoelectric conversion layer and electron transport layer, the electron affinity, the ionization potential, the stability and the like. Specific examples thereof include an electrically conductive metal oxide such as tin oxide, zinc oxide, indium oxide and indium tin oxide (ITO), a metal such as gold, silver, chromium and nickel, a mixture or laminate of such a metal and such an electrically conductive metal oxide, an inorganic electrically conductive substance such as copper iodide and copper sulfide, an organic electrically conductive material such as polyaniline, polythiophene and polypyrrole, a silicon compound, and a laminate thereof with ITO. An electrically conductive metal oxide is preferred, and ITO and IZO are more preferred in view of productivity, high electrical conductivity, transparency and the like.

For the production of the electrode, various methods are used according to the material, but, for example, in the case of ITO, the film is formed by a method such as electron beam method, sputtering method, resistance heating vapor deposition method, chemical reaction method (e.g., sol-gel method) or coating of a dispersion of indium tin oxide. In the case of ITO, an UV-ozone treatment, a plasma treatment or the like can be applied.

The conditions when forming an electrode film that is transparent (transparent electrode film) are described below. The silicon substrate temperature when forming the transparent electrode film is preferably 500° C. or less, more preferably 300° C. or less, still more preferably 200° C. or less, yet still more preferably 150° C. or less. A gas may be introduced during the formation of the transparent electrode film, and the gas species is basically not limited, but Ar, He, oxygen, nitrogen or the like may be used. Also, a mixed gas of these gases may be used. In particular, in the case of an oxide material, oxygen is preferably used, because an oxygen defect enters the film in many cases.

The preferred range of the surface resistance of the transparent electrode film varies depending on whether the film is the first electrode film 11 or the second electrode film 13. In the case where the signal readout part has a CMOS structure, the surface resistance of the transparent conductive film is preferably 10,000 Ω/sq. or less, more preferably 1,000 Ω/sq. or less. In the case where the signal readout part is hypothetically in a CCD structure, the surface resistance is preferably 1,000 Ω/sq. or less, more preferably 100 Ω/sq. or less. In use as the second electrode film 13, the surface resistance is preferably 1,000,000Ω/sq. or less, more preferably 100,000 Ω/sq. or less.

Above all, the material of the transparent electrode film is preferably any of ITO, IZO, $SnO_2$, ATO (antimony-doped tin oxide), ZnO, AZO (Al-doped zinc oxide), GZO (gallium-doped zinc oxide), $TiO_2$ and FTO (fluorine-doped tin oxide). The light transmittance of the transparent electrode film is preferably 60% or more, more preferably 80% or more, still more preferably 90% or more, yet still more preferably 95% or more, at the absorption peak wavelength of the photoelectric conversion film contained in the photoelectric conversion part containing the transparent electrode film.

In the case of stacking a plurality of layers as the intermediate layer 12, the first electrode film 11 and the second electrode film 13 each needs to transmit light at wavelengths other than light detected by respective photoelectric conversion layers from the photoelectric conversion film positioned nearest to the light incident side to the photoelectric conversion film positioned farthest from the light incident and therefore, it is preferred to use a material that transmits preferably 90% or more, more preferably 95% or more, of visible light.

The second electrode film 13 is preferably produced in a plasma-free state. By producing the second electrode film 13 in a plasma-free state, the effect of a plasma on the substrate can be reduced and good photoelectric conversion properties can be obtained. Here, the term "plasma-free state" means a state where a plasma is not generated during formation of the second electrode film 13 or where the distance from the plasma generation source to the substrate is 2 cm or more, preferably 10 cm or more, more preferably 20 cm or more, and the plasma that reaches the substrate is reduced.

Examples of the apparatus where a plasma is not generated during formation of the second electrode film 13 include an electron beam vapor deposition apparatus (EB vapor deposition apparatus) and a pulse laser vapor deposition apparatus. As for the EB vapor deposition apparatus and pulse laser vapor deposition apparatus, there may be used an apparatus described, for example, in Yutaka Sawada (supervisor), Toumei Doden Maku no Shin Tenkai (New Development of Transparent Electrically Conductive Film), CMC (1999), Yutaka Sawada (supervisor), Toumei Doden Maku no Shin Tenkai II (New Development II of Transparent Electrically Conductive Film), CMC (2002), Toumei Doden Maku no Gijutsu (Technology of Transparent Electrically Conductive Film), JSPS, Ohm-sha (1999), and references and the like recited therein. In the following, the method of performing the formation of transparent electrode film by using an EB vapor deposition apparatus is referred to as an "EB vapor deposition method", and the method of performing the formation of transparent electrode film by using a pulse laser vapor deposition apparatus is referred to as a "pulse laser vapor deposition method".

As for the apparatus capable of realizing a state where the distance from the plasma generation source to the substrate is 2 cm or more and the plasma that reaches the substrate is reduced (hereinafter referred to as a "plasma-free film-forming apparatus"), for example, a counter target-type sputtering apparatus and an arc plasma vapor deposition method may be used. In this respect, there may be used an apparatus described, for example, in Yutaka Sawada (supervisor), Toumei Doden Maku no Shin Tenkai (New Development of Transparent Electrically Conductive Film), CMC (1999), Yutaka Sawada (supervisor), Toumei Doden Maku no Shin Tenkai II (New Development II of Transparent Electrically Conductive Film), CMC (2002), Toumei Doden Maku no Gijutsu (Technology of Transparent Electrically Conductive Film), JSPS, Ohm-sha (1999), and references and the like recited therein.

In the case where the second electrode film 13 is a transparent electrically conductive film such as TCO, DC short or increase of leak current sometimes occurs. One of causes thereof is considered because fine cracks introduced into the photoelectric conversion layer 123 are coveraged by a dense film such as TCO and conduction with the first electrode film 11 on the opposite side increases. Therefore, in the case of an electrode having relatively poor film quality such as Al, increase of leak current less occurs. The increase of leak current can be greatly suppressed by controlling the thickness of the second electrode film 13 with respect to the thickness (that is, the crack depth) of the photoelectric conversion layer 123. The thickness of the second electrode film 13 is preferably ⅕ or less, more preferably ¹⁄₁₀ or less, of the thickness of the photoelectric conversion layer 123.

Usually, when the thickness of the electrically conductive film is made smaller than a certain range, an abrupt increase of the resistance value is brought about, but in the solid-state image device 1000 of this embodiment, the sheet resistance may be preferably from 100 to 10,000 $\Omega$/sq. and the latitude as to in which range the film thickness can be reduced is large. Also, as the thickness of the transparent electrically conductive thin film is smaller, the quantity of light absorbed becomes smaller and the light transmittance generally increases. The increase of light transmittance brings about an increase of light absorption in the photoelectric conversion layer 123 and an increase of photoelectric conversion performance, and this is very preferred. Considering the suppression of leak current as well as the increase of resistance value of thin film and increase of transmittance, which are associated with reduction in the film thickness, the thickness of the transparent electrically conductive thin film is preferably from 5 to 100 nm, more preferably from 5 to 20 nm.

The material of the transparent electrode film is preferably a material that can be film-formed by a plasma-free film-forming apparatus, an EB vapor deposition apparatus or a pulsed laser vapor deposition apparatus, and suitable examples thereof include a metal, an alloy, a metal oxide, a metal nitride, a metal boride, an organic electrically conductive compound and a mixture thereof. Specific examples thereof include an electrically conductive metal oxide such as tin oxide, zinc oxide, indium oxide, indium zinc oxide (IZO), indium tin oxide (ITO) and indium tungsten oxide (IWO), a metal nitride such as titanium nitride, a metal such as gold, platinum, silver, chromium, nickel and aluminum, a mixture or laminate of such a metal and such an electrically conductive metal oxide, an inorganic electrically conductive substance such as copper iodide and copper sulfide, an organic electrically conductive material such as polyaniline, polythiophene and polypyrrole, and a laminate thereof with ITO. Furthermore, those described in detail, for example. in Yutaka Sawada (supervisor), Toumei Doden Maku no Shin Tenkai (New Development of Transparent Conductive Film), CMC (1999), Yutaka Sawada (supervisor), Toumei Doden Maku no Shin Tenkai II (New Development II of Transparent Conductive Film), CMC (2002), and Toumei Doden Maku no Gijutsu (Technology of Transparent Conductive Film), JSPS, Ohm-sha (1999) may be also used.

(Fourth Embodiment)

In this embodiment, the inorganic layer having a construction shown in FIG. 12 described in the third embodiment is constructed such that two photodiodes are not stacked inside of the n-type silicon substrate but two diodes are arrayed in the direction perpendicular to the incidence direction of incident light to detect light of two colors inside the n-type silicon substrate.

Figure 14:
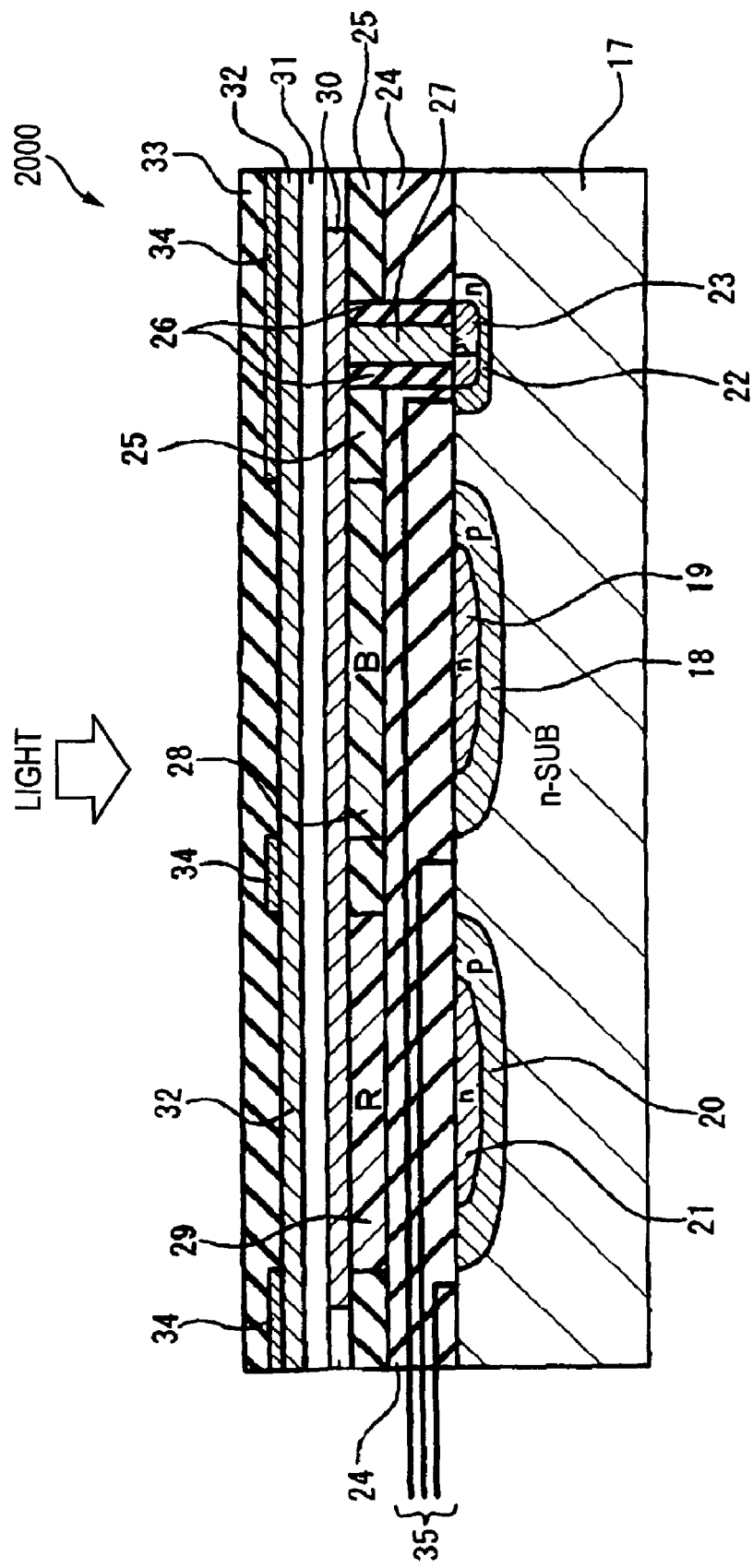
FIG. 14 is a schematic cross-sectional view of one pixel portion of a solid-state image device for explaining the fourth exemplary embodiment of the present invention.

FIG. 14 is a schematic cross-sectional view of one pixel portion of a solid-state image device for explaining the fourth embodiment of the present invention.

One pixel of the solid-state image device 2000 shown in FIG. 14 has a construction containing an n-type silicon substrate 17 and a photoelectric conversion part that comprises a first electrode film 30 formed above the n-type silicon substrate 17, an intermediate layer 31 formed on the first electrode film 30 and a second electrode film 32 formed on the intermediate layer 31, where a light-shielding film 34 having provided therein an opening is formed on the photoelectric conversion part and the light-receiving region of the intermediate layer 31 is limited by the light-shielding film 34. Also, a transparent insulating film 33 is formed on the light-shielding film 34.

The first electrode film 30, the intermediate layer 31 and the second electrode film 32 have the same constructions as the first electrode film 11, the intermediate layer 12 and the second electrode film 13, respectively.

On the surface of the n-type silicon substrate 17 under the opening of the light-shielding film 34, a photodiode consisting of an n region 19 and a p region 18 and a photodiode consisting of an n region 21 and a p region 20 are formed to be juxtaposed on the surface of the n-type silicon substrate 17. An arbitrary direction on the n-type silicon substrate 17 surface becomes the direction perpendicular to the incidence direction of incident light.

Above the photodiode consisting of an n region 19 and a p region 18, a color filter 28 that transmits B light via a transparent insulating film 24 is formed, and the first electrode film 30 is formed thereon. Above the photodiode consisting of an n region 21 and a p region 20, a color filter 29 that transmits R light via the transparent insulating film 24 is formed, and the first electrode film 30 is formed thereon. The peripheries of color filters 28 and 29 are covered with a transparent insulating film 25.

The photodiode consisting of an n region 19 and a p region 18 absorbs B light transmitted through the color filter 28, generates holes in proportion to the light absorbed and accumulates the generated holes in the p region 18. The photodiode consisting of an n region 21 and a p region 20 absorbs R light transmitted through the color filter 29, generates holes in proportion to the light absorbed and accumulates the generated holes in the p region 20.

In the portion light-shielded by the light-shielding film 34 of the p-type silicon substrate 17 surface, a p+ region 23 is formed, and the periphery of the p+ region 23 is surrounded by an n region 22.

The p+ region 23 is electrically connected to the first electrode film 30 via a connection part 27 formed in the opening bored through the insulating films 24 and 25 and in this region, holes collected at the first electrode film 30 are accumulated via the connection part 27. The connection part 27 is electrically insulated by an insulating film 26 from portions except for the first electrode film 30 and the p+ region 23.

The holes accumulated in the p region 18 are converted into signals in proportion to the electric charge amount by an MOS circuit (not shown) comprising a p-channel MOS transistor formed inside of the n-type silicon substrate 17, the holes accumulated in the p region 20 are converted into signals in proportion to the electric charge amount by an MOS circuit (not shown) comprising a p-channel MOS transistor formed inside of the n-type silicon substrate 17, the holes accumulated in the p+ region 23 are converted into signals in proportion to the electric charge amount by an MOS circuit (not shown) comprising a p-channel MOS transistor formed inside of the n region 22, and these signals are output to the outside of the solid-state image device 2000. The MOS circuits above constitute the signal readout part specified in the scope of claim for patent. Each MOS circuit is connected to a signal readout pad (not shown) by a wiring 35.

Incidentally, the signal readout part may be constructed by CCD and an amplifier, instead of MOS circuits. More specifically, the signal readout part may be a signal readout part where holes accumulated in the p region 18, p region 20 and p+ region 23 are read into CCD formed inside of the n-type silicon substrate 17 and further transferred to an amplifier by the CCD and signals in proportion to the holes transferred are output from the amplifier.

In this way, the signal readout part includes CCD and CMOS structures, but in view of power consumption, high-speed readout, pixel addition, partial readout and the like, CMOS is preferred.

Incidentally, in FIG. 14, color separation between B light and R light is effected by color filters 28 and 29, but instead of providing color filters 28 and 29, the depth of the pn junction plane by the p region 20 and n region 21 and the depth of the pn junction plane by the p region 18 and n region 19 each may be adjusted to absorb R light and B light by respective photodiodes. In this case, an inorganic photoelectric conversion part composed of an inorganic material that absorbs light transmitted through the intermediate layer 31, generates electric charges in proportion to the light absorbed and accumulates the electric charges may also be formed between the n-type silicon substrate 17 and the first electrode film 30 (for example, between the insulating film 24 and the n-type silicon substrate 17). If this is the case, an MOS circuit for reading out signals in proportion to the electric charges accumulated in a charge accumulation region of the inorganic photoelectric conversion part may be provided inside of the n-type silicon substrate 17 and the wiring 35 may be connected also to this MOS circuit.

Also, there may take a construction where one photodiode is provided inside of the n-type silicone substrate 17 and a plurality of layers as the photoelectric conversion part are stacked above the n-type silicon substrate 17; a construction where a plurality of photodiodes are provided inside of the n-type silicon substrate 17 and a plurality of layers as the photoelectric conversion part are stacked above the n-type silicon substrate 17; or when a color image need not be formed, a construction where one photodiode is provided inside of the n-type silicon substrate 17 and only one layer as the photoelectric conversion part is stacked.

(Fifth Embodiment)

The solid-state image device of this embodiment has a construction where an inorganic layer having the construction shown in FIG. 12 described in the third embodiment is not provided but a plurality of (here, three) photoelectric conversion layers are stacked above the silicon substrate.

Figure 15:
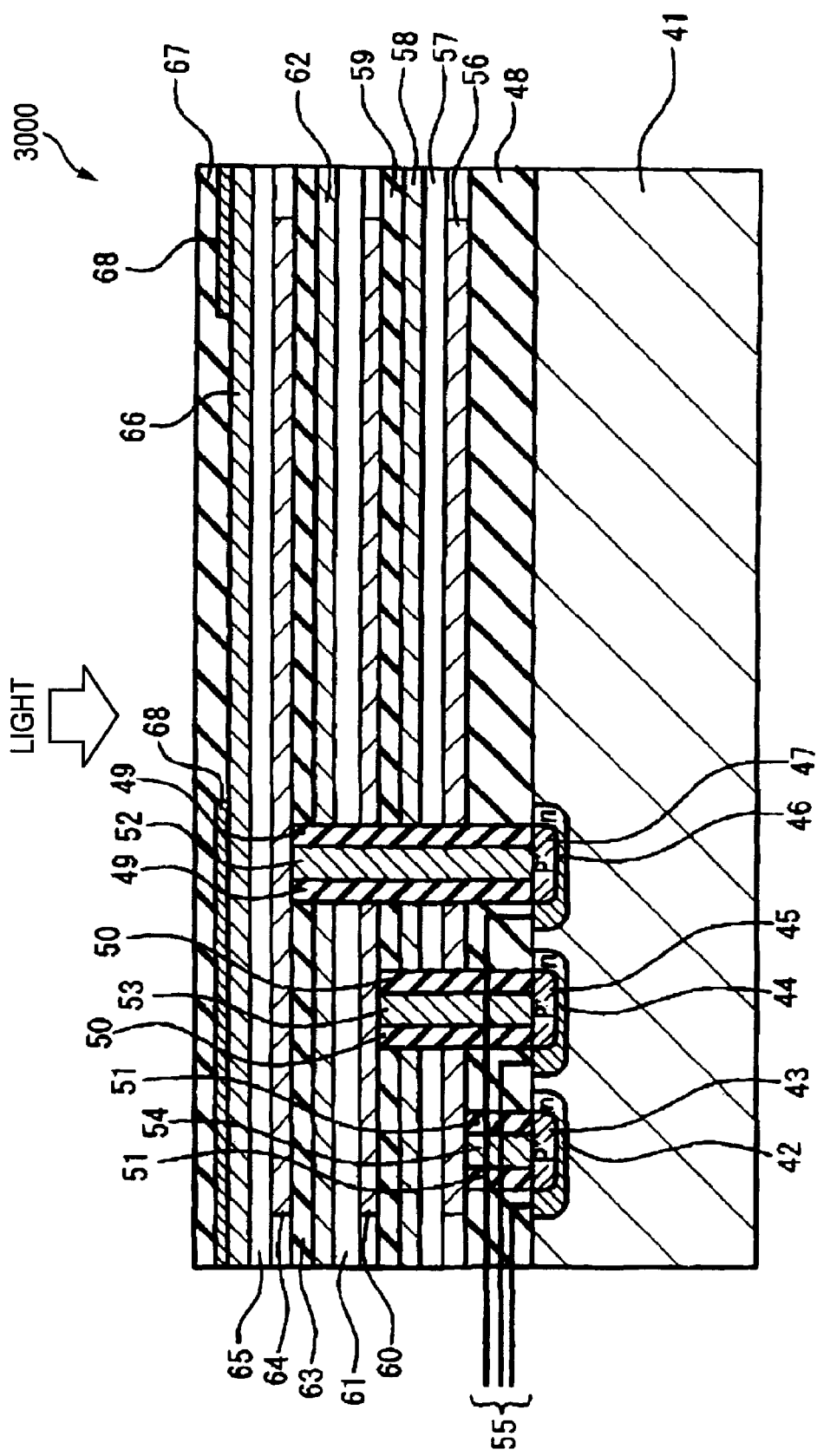
FIG. 15 is a schematic cross-sectional view of one pixel portion of a solid-state image device for explaining the fifth exemplary embodiment of the present invention.

FIG. 15 is a schematic cross-sectional view of one pixel portion of a solid-state image device for explaining the fifth embodiment of the present invention.

The solid-state image device 3000 shown in FIG. 15 has a construction where an R photoelectric conversion part containing a first electrode film 56, an intermediate layer 57 formed on the first electrode film 56 and a second electrode film 58 formed on the intermediate layer 57, a B photoelectric conversion part containing a first electrode film 60, an intermediate layer 61 formed on the first electrode film 60 and a second electrode film 62 formed on the intermediate layer 61, and a G photoelectric conversion part containing a first electrode film 64, an intermediate layer 65 formed on the first electrode film 64 and a second electrode film 66 formed on the intermediate layer 65 are stacked in this order above the silicon substrate 41 in a state of the first electrode film contained in each photoelectric conversion part being arranged to face the silicon substrate 41 side.

A transparent insulating film 48 is formed on the silicon substrate 41, the R photoelectric conversion part is formed thereon, a transparent insulating film 59 is formed thereon, the B photoelectric conversion part is formed thereon, a transparent insulating film 63 is formed thereon, the G photoelectric conversion part is formed thereon, a light-shielding film 68 having provided therein an opening is formed thereon, and a transparent insulating film 67 is formed thereon.

The first electrode film 64, intermediate layer 65 and second electrode film 66 contained in the G photoelectric conversion part have the same constructions as the first electrode film 11, intermediate layer 12 and second electrode film 13 shown in FIG. 12, respectively.

The first electrode film 60, intermediate layer 61 and second electrode film 62 contained in the B photoelectric conversion part have the same constructions as the first electrode film 11, intermediate layer 12 and second electrode film 13 shown in FIG. 12, respectively. However, for the photoelectric conversion layer contained in the intermediate layer 61, a material that absorbs blue light and generates an electron and a hole in proportion to the light absorbed is used.

The first electrode film 56, intermediate layer 57 and second electrode film 58 contained in the R photoelectric conversion part have the same constructions as the first electrode film 11, intermediate layer 12 and second electrode film 13 shown in FIG. 12, respectively. However, for the photoelectric conversion layer contained in the intermediate layer 57, a material that absorbs red light and generates an electron and a hole in proportion to the light absorbed is used.

For the electron-blocking layer and hole-blocking layer contained in each of the intermediate layers 61 and 57, an appropriate material and an appropriate construction are preferably selected so as not to create an energy barrier to the transport of a signal charge in terms of the relationship between HOMO and LUMO energy levels of each photoelectric conversion layer and HOMO and LUMO energy levels of each blocking layer adjacent thereto.

In the portion light-shielded by the light-shielding film 68 of the silicon substrate 41 surface, p+ regions 43, 45 and 47 are formed and the peripheries of these regions are surrounded by n regions 42, 44 and 46, respectively.

The p+ region 43 is electrically connected to the first electrode film 56 via a connection part 54 formed in an opening bored through the insulating film 48 and in this region, holes collected at the first electrode 56 are accumulated via the connection part 54. The connection part 54 is electrically insulated by an insulating film 51 from portions except for the first electrode film 56 and the p+ region 43.

The p+ region 45 is electrically connected to the first electrode film 60 via a connection part 53 formed in an opening bored through the insulating film 48, R photoelectric conversion part and insulating film 59 and in this region, holes collected at the first electrode film 60 are accumulated via the connection part 53. The connection part 53 is electrically insulated by an insulating film 50 from portions except for the first electrode film 60 and the p+ region 45.

The p+ region 47 is electrically connected to the first electrode film 64 via a connection part 52 formed in an opening bored through the insulating film 48, R photoelectric conversion part, insulating film 59, B photoelectric conversion part and insulating film 63 and in this region, holes collected at the first electrode film 64 are accumulated via the connection part 52. The connection part 52 is electrically insulated by an insulating film 49 from portions except for the first electrode film 64 and the p+ region 47.

The holes accumulated in the p+ region 43 are converted into signals in proportion to the electric charge amount by an MOS circuit (not shown) comprising a p-channel MOS transistor formed inside of the n region 42, the holes accumulated in the p+ region 45 are converted into signals in proportion to the electric charge amount by an MOS circuit (not shown) comprising a p-channel MOS transistor formed inside of the n region 44, the holes accumulated in the p+ region 47 are converted into signals in proportion to the electric charge amount by an MOS circuit (not shown) comprising a p-channel MOS transistor formed inside of the n region 46, and these signals are output to the outside of the solid-state image device 3000. The MOS circuits above constitute the signal readout part specified in the scope of claim for patent. Each MOS circuit is connected to a signal readout pad (not shown) by a wiring 55. Here, the signal readout part may be constructed by CCD and an amplifier, instead of MOS circuits. More specifically, the signal readout part may be a signal readout part where holes accumulated in the p+ regions 43, 45 and 47 are read into CCD formed inside of the silicon substrate 41 and further transferred to an amplifier by the CCD, and signals in proportion to the holes transferred are output from the amplifier.

Incidentally, an inorganic photoelectric conversion part composed of an inorganic material which receives light transmitted through the intermediate layers 57, 61 and 65, generates electric charges in proportion to the light received and accumulates the electric charges may also be formed between the silicon substrate 41 and the first electrode film 56 (for example, between the insulating film 48 and the silicon substrate 41). In this case, an MOS circuit for reading out signals in proportion to the electric charges accumulated in a charge accumulation region of the inorganic photoelectric conversion part may be provided inside of the silicon substrate 41 and the wiring 55 may be connected also to this MOS circuit.

Such a configuration described in the third and forth embodiments, where a plurality of photoelectric conversion layers are stacked on a silicon substrate, can be realized by the construction shown in FIG. 15.

In these descriptions, the photoelectric conversion layer that absorbs B light means a photoelectric conversion layer which can absorb at least light at a wavelength of 400 to 500 nm and in which the absorption factor at a peak wavelength in the wavelength region above is preferably 50% or more. The photoelectric conversion layer that absorbs G light means a photoelectric conversion layer which can absorb at least light at a wavelength of 500 to 600 nm and in which the absorption factor at a peak wavelength in the wavelength region above is preferably 50% or more. The photoelectric conversion layer that absorbs R light means a photoelectric conversion layer which can absorb at least light at a wavelength of 600 to 700 nm and in which the absorption factor at a peak wavelength in the wavelength region above is preferably 50% or more.

In the case of the construction of the third or fifth embodiment, there may be considered a pattern where colors are detected in the order such as BGR, BRG, GBR, GRB, RBG and RGB from the upper layer. Preferably, the uppermost layer is G. In the case of the construction of the fourth embodiment, there may be employed a combination such as BG layers in the same plane for the lower layer when the upper layer is R layer; GR layers in the same plane for the lower layer when the upper layer is a B layer; or BR layers in the same plane for the lower layer when the upper layer is a G layer. A construction where the upper layer is a G layer and the lower layer is BR layers in the same plane is preferred.

(Sixth Embodiment)

Figure 16:
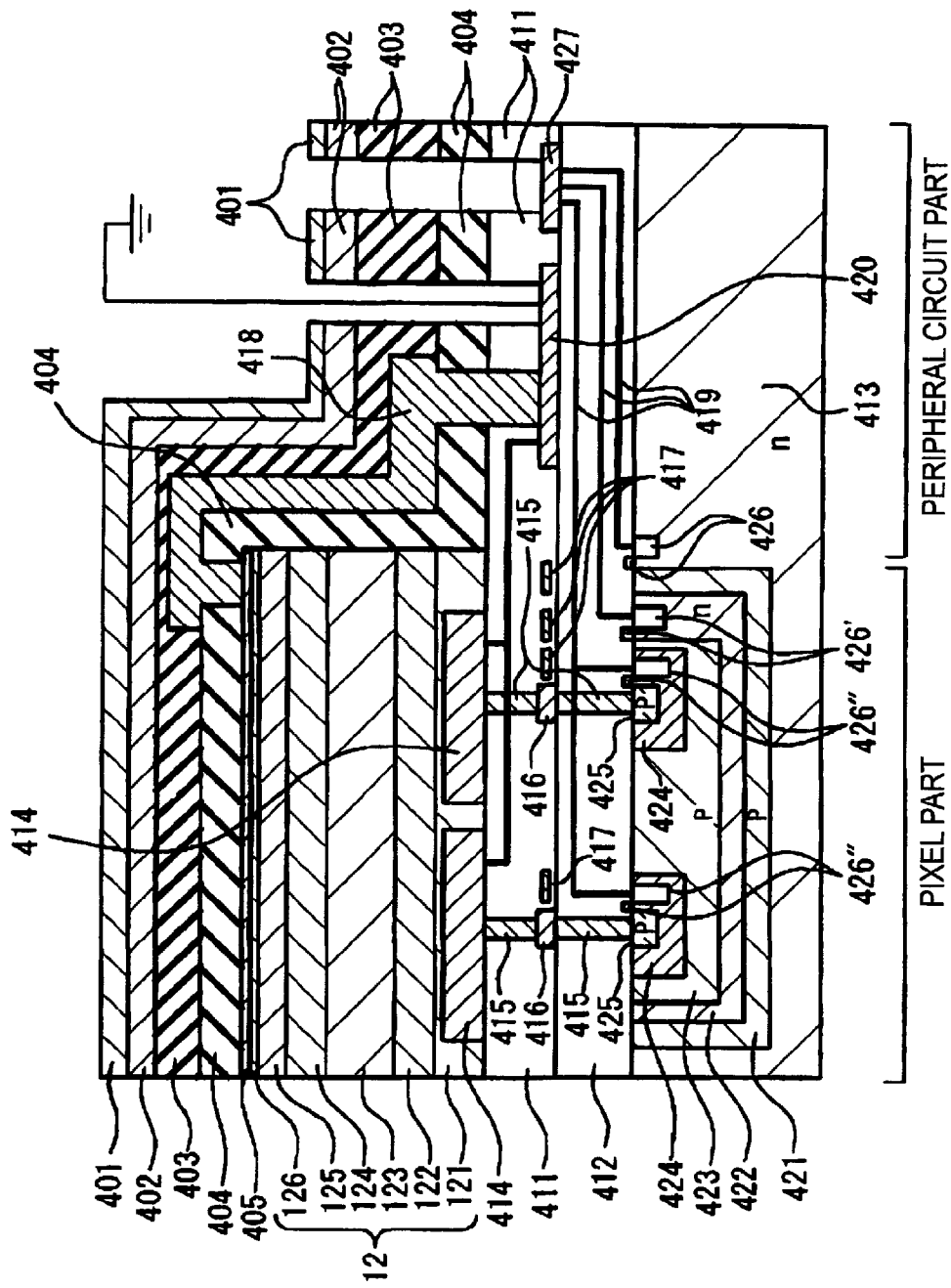
FIG. 16 is a schematic cross-sectional view of a solid-state image device for explaining the sixth exemplary embodiment of the present invention.

FIG. 16 is a schematic cross-sectional view of a solid-state image device for explaining the sixth embodiment of the present invention. In FIG. 16, a cross-section of two pixel portions in a pixel part that is a portion of detecting light and accumulating an electric charge, and a cross-section of a peripheral circuit part that is a portion where, for example, wiring connected to an electrode in the pixel part or bonding PAD connected to the wiring is formed, are shown together.

In an n-type silicon substrate 413 of the pixel part, a p region 421 is formed in the surface portion, an n region 422 is formed in the surface portion of the p region 421, a p region 423 is formed in the surface portion of the n region 422, and an n region 424 is formed in the surface portion of the p region 423.

The p region 421 accumulates holes of a red (R) component photoelectrically converted by pn junction with the n-type silicon substrate 413. A potential change in the p region 421 due to accumulation of holes of the R component is read out from an MOS transistor 426 formed in the n-type silicon substrate 413 into a signal readout PAD 427 via a metal wiring 419 connected to the MOS transistor.

The p region 423 accumulates holes of a blue (B) component photoelectrically converted by pn junction with the n region 422. A potential change in the p region 423 due to accumulation of holes of the B component is read out from an MOS transistor 426' formed in the n region 422 into a signal readout PAD 427 via a metal wiring 419 connected to the MOS transistor.

In the n region 424, a hole accumulation region 425 comprising a p region that accumulates holes of a green (G) component generated in the photoelectric conversion layer 123 stacked above the n-type silicon substrate 413 is formed. A potential change in the hole accumulation region 425 due to accumulation of holes of the G component is read out from an MOS transistor 426" formed in the n region 424 into a signal readout PAD 427 via a metal wiring 419 connected to the MOS transistor. Usually, the signal readout PAD 427 is provided for each of the transistors from which respective color components are read out.

Here, the members such as p region, n region, transistor and metal wiring are schematically shown, but the construction and the like of each member are not limited thereto, and an optimal selection is appropriately made therefor. Separation between B light and R light is effected by the depth in the silicon substrate and therefore, for example, selection of the depth of pn junction or the like from the silicon substrate surface or the dope concentration of each impurity is important. A technique used in a normal CMOS image sensor may be applied to the CMOS circuit working out to a signal readout part. Specifically, a circuit construction capable of reducing the number of transistors in the pixel part, including a low-noise readout column amplifier and a CDS circuit, may be applied.

A transparent insulating film 412 comprising silicon oxide, silicon nitride or the like as the main component is formed on the n-type silicon substrate 413, and a transparent insulating film 411 comprising silicon oxide, silicon nitride or the like as the main component is formed on the insulating film 412. The thickness of the insulating film 412 is preferably smaller and is 5 μm or less, preferably 3 μm or less, more preferably 2 μm or less, still more preferably 1 μm or less.

Inside of the insulating films 411 and 412, a plug 415 comprising, for example, tungsten as the main component and electrically connecting the first electrode film 414 to the p region 425 as a hole accumulation region is formed, and the plugs 415 are relayed and connected by a pad 416 between the insulating film 411 and the insulating film 412. As for the pad 416, a pad comprising aluminum as the main component is preferably used. Inside of the insulating film 412, the above-described metal wiring 419, gate electrodes for the transistors 426, 426' and 426", and the like are also formed. It is preferred that a barrier layer including the metal wiring is provided. The plug 415 is provided for every one pixel.

Inside of the insulating film 411, a light-shielding film 417 is provided for preventing a noise attributable to generation of an electric charge by the pn junction between the n region 424 and the p region 425. As for the light-shielding film 417, a film comprising tungsten, aluminum or the like as the main component is usually used. Inside of the insulating film 411, a bonding PAD 420 (PAD for externally supplying a power source) and a signal readout PAD 427 are formed, and a metal wiring (not shown) for electrically connecting the bonding PAD 420 to the first electrode film 414 described later is also formed.

A transparent first electrode film 414 is formed on the plug 415 for each pixel inside of the insulating film 411. The first electrode film 414 is divided for each pixel, and the size thereof determines the light-receiving area. To the first electrode film 414, a bias is applied through the wiring from the bonding PAD 420. A construction where holes can be accumulated in the hole accumulation region 425 by applying a negative bias to the first electrode 414 with respect to a second electrode film 405 which is described later, is preferred.

An intermediate layer 12 having the same structure as in FIG. 12 is formed on the first electrode film 414, and a second electrode film 405 is formed thereon.

A protective film 404 comprising silicon nitride or the like as the main component and having a function of protecting the intermediate layer 12 is formed on the second electrode film 405. In the protective film 404, an opening is formed at a position not overlapping with the first electrode film 414 of the pixel part. Also, an opening is formed in a part of the insulating film 411 and the protective film 404 on the bonding PAD 420. A wiring 418 comprising aluminum or the like for electrically connecting between the second electrode film 405 and the bonding PAD 420, which are exposed by those two openings, and giving a potential to the second electrode film 405 is formed inside of the openings as well as on the protective film 404. As for the material of the wiring 418, an aluminum-containing alloy such as Al—Si or Al—Cu alloy may also be used.

A protective film 403 comprising silicon nitride or the like as the main component and protecting the wiring 418 is formed on the wiring 418, an infrared-cutting dielectric multilayer film 402 is formed on the protective film 403, and an antireflection film 401 is formed on the infrared-cutting dielectric multilayer film 402.

The first electrode film 414 fulfills the same function as the first electrode film 11 shown in FIG. 12. The second electrode film 405 fulfills the same function as the second electrode film 13 shown in FIG. 12.

Such a construction enables detecting three BGR color lights by one pixel to effect color imaging. In the construction of FIG. 16, R and B each is used as a common value in two pixels, and only the G value is separately used, but since the sensitivity of G is important in producing an image, a good color image can be produced even by such a construction.

The solid-state image device described above can be applied to an image device including a digital camera, a video camera, a facsimile, a scanner and a copier and can also be utilized as an optical sensor such as biosensor and chemical sensor.

Examples of the material for the insulating films described in these embodiments include $SiO_x$, $SiN_x$, BSG, PSG, BPSG, a metal oxide such as $Al_2O_3$, MgO, GeO, NiO, CaO, BaO, $Fe_2O_3$, $Y_2O_3$ and $TiO_2$, and a metal fluoride such as $MgF_2$, LiF, $AlF_3$ and $CaF_2$. Among these materials, $SiO_x$, $SiN_x$, BSG, PSG and BPSG are most preferred.

Incidentally, in the third to sixth embodiments, either a hole or an electron may be used for reading out signals from portions other than the photoelectric conversion layer. More specifically, as described above, there may take a construction where holes are accumulated in an inorganic photoelectric conversion part provided between a semiconductor substrate and a photoelectric conversion part stacked thereon or in a photodiode formed inside of the semiconductor substrate and signals in proportion to the holes are read out by a signal readout part, or a construction where electrons are accumulated in an inorganic photoelectric conversion part or a photodiode formed inside of a semiconductor substrate and signals in proportion to the electrons are read out by a signal readout part.

In the third to sixth embodiments, a construction shown in FIG. 13 is used as the photoelectric conversion part provided above the silicon substrate, but a construction shown in FIG. 1 and FIGS. 6 to 9 may also be used. According to the construction shown in FIG. 13, an electron and a hole can be blocked and therefore, the effect of suppressing a dark current is high. In the case where the electrode opposite the light incident side is used as the electrode for collecting electrons, there may take a construction where in FIG. 12, the connection part 9 is connected to the second electrode 13; where in FIG. 14, the connection part 27 is connected to the second electrode 13; or where in FIG. 15, the connection part 54 is connected to the second electrode 58, the connection part 53 is connected to the second electrode 62 and the connection part 52 is connected to the second electrode 66.

The solid-state image device described in this embodiment has a construction where a large number of pixels, one of which is shown in FIGS. 12 to 16, are disposed in an array manner in the same plane, and since RGB color signals can be obtained by one pixel, this one pixel can be regarded as a photoelectric conversion element that converts RGB lights into electric signals. Therefore, the solid-state image device described in this embodiment can be said to have a construction where a large number of photoelectric conversion elements shown in FIGS. 12 to 16 are disposed in an array manner in the same plane.

(Seventh Embodiment)

Figure 17:
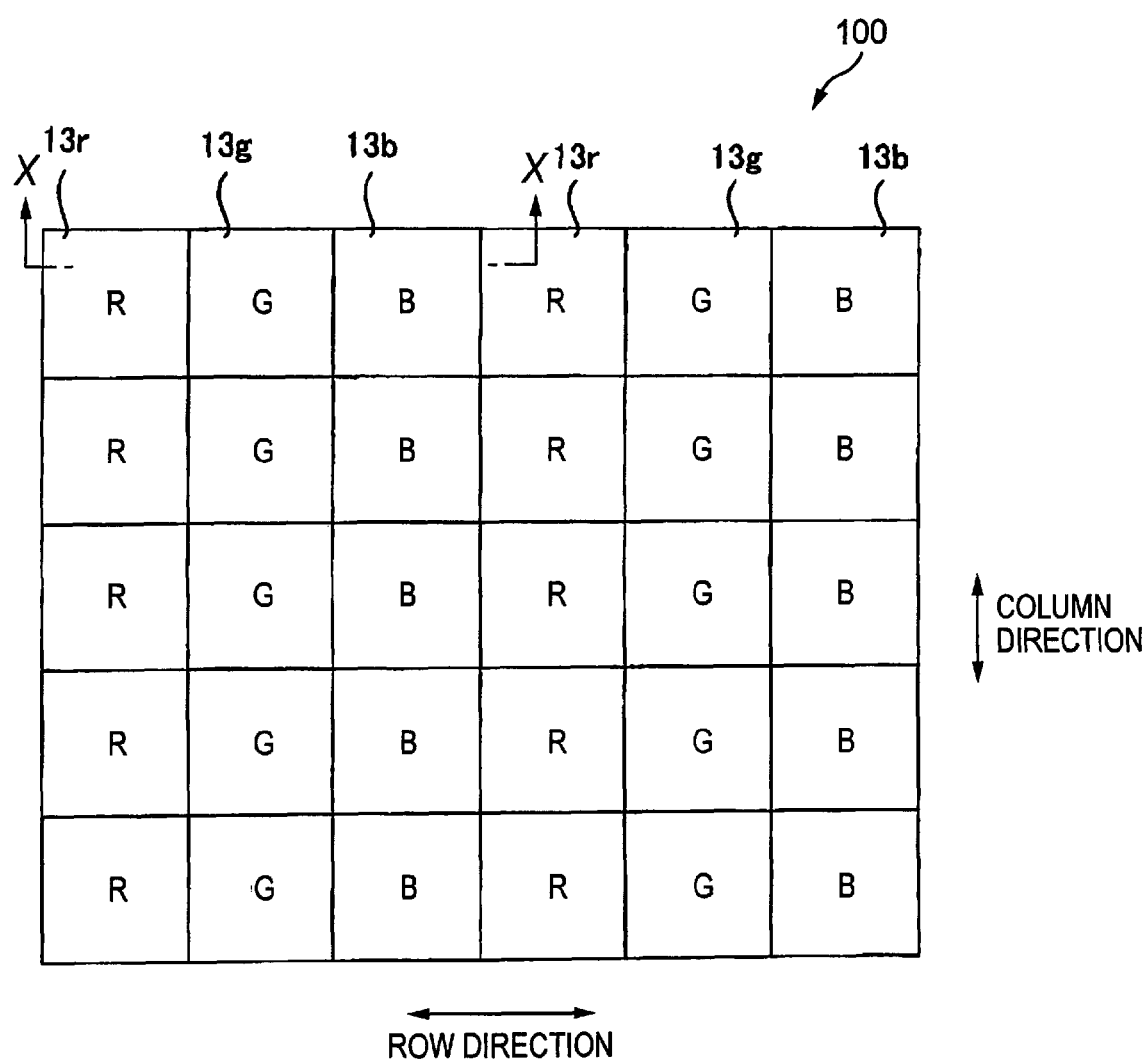
FIG. 17 is a partial schematic surface view of a solid-state image device for explaining the exemplary embodiment of the present invention.
Figure 18:
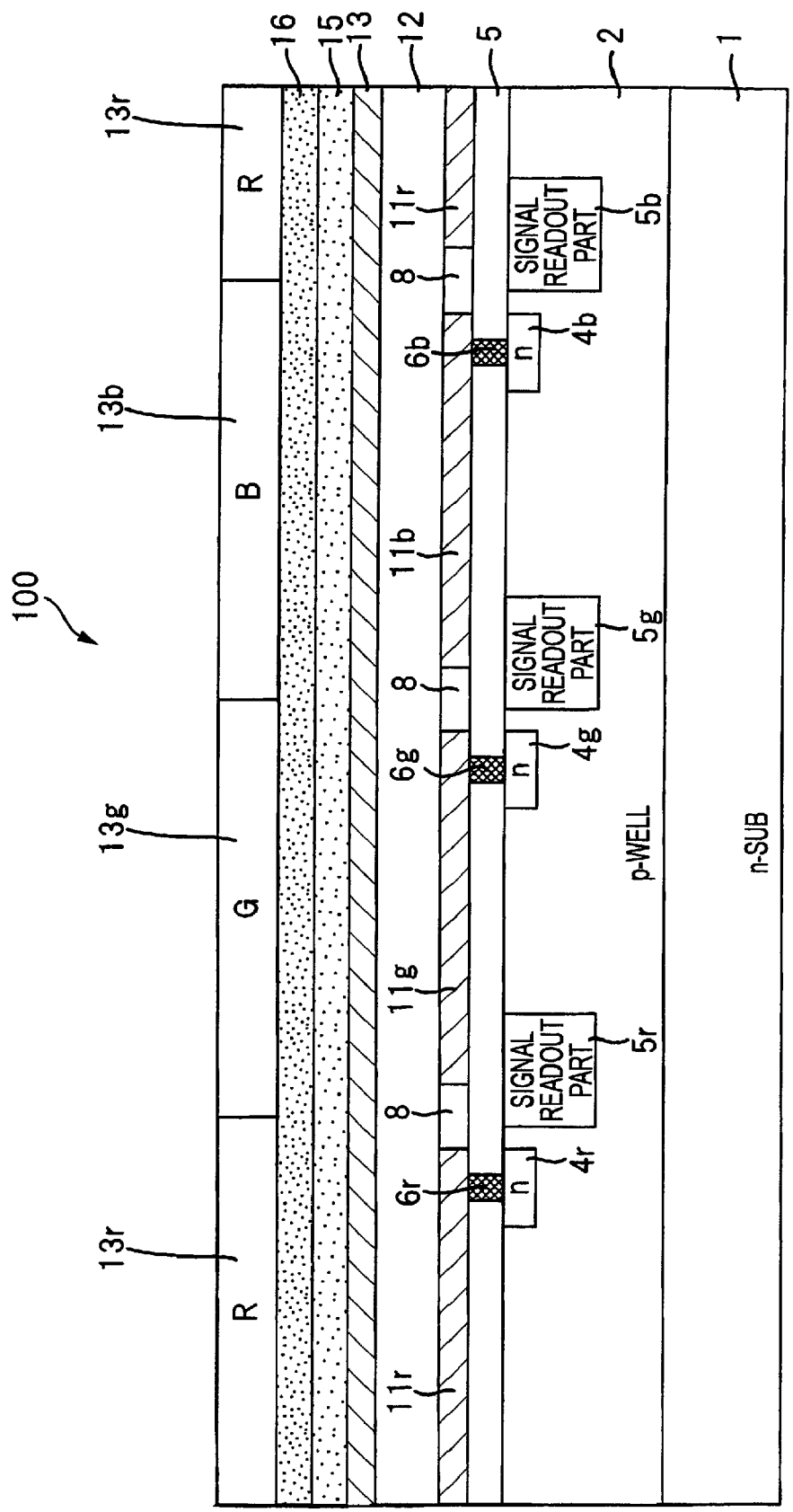
FIG. 18 is a schematic cross-sectional view cut along the X-X line of the image device shown in FIG. 17.

A seventh embodiment where a solid-state image device is realized using a photoelectric conversion element having a construction shown in FIGS. 17 and 18 is described.

FIG. 17 is a partial surface schematic view of an image device for explaining the embodiment of the present invention, and FIG. 18 is a schematic cross-sectional view cut along the X-X line of the image device shown in FIG. 17. In FIG. 17, illustration of a microlens 14 is omitted.

A p-well layer 2 is formed on an n-type silicon substrate 1. In the following, the n-type silicon substrate 1 and the p-well layer 2 are collectively referred to as a semiconductor substrate. In the row direction and the column direction crossing with the row direction at right angles in the same plane above the semiconductor substrate, three kinds of color filters, that is, a color filter 13*r* mainly transmitting R light, a color filter 13*g* mainly transmitting G light, and a color filter 13*b* mainly transmitting B light, each is numerously arrayed.

A known material may be used for the color filter 13r, but such a material transmits R light. A known material may be used for the color filter 13g, but such a material transmits G light. A known material may be used for the color filter 13b, but such a material transmits B light.

As for the array of color filters 13r, 13g and 13b, a color filter array used in known single-plate solid-state image devices (e.g., Bayer array, longitudinal stripe, lateral stripe) may be employed.

A transparent electrode 11r is formed above an n region 4r, a transparent electrode 11g is formed above an n region 4g, and a transparent electrode 11b is formed above an n region 4b. The transparent electrodes 11r, 11g and 11b are divided to correspond to the color filters 13r, 13g and 13b, respectively. The transparent electrodes 11r, 11g and 11b each has the same function as the lower electrode 11 of FIG. 1.

A photoelectric conversion film 12 in one-sheet construction shared in common among the color filters 13r, 13g and 13b is formed on the transparent electrodes 11r, 11g and 11b.

An upper electrode 13 in one-sheet construction shared in common among the color filters 13r, 13g and 13b is formed on the photoelectric conversion film 12.

A photoelectric conversion element corresponding to the color filter 13r is formed by the transparent electrode 11r, the opposing upper electrode 13, and a part of the photoelectric conversion film 12 sandwiched therebetween. This photoelectric conversion element is hereinafter referred to as an R photoelectric conversion element, because this element is formed on a semiconductor substrate.

A photoelectric conversion element corresponding to the color filter 13g is formed by the transparent electrode 11g, the opposing upper electrode 13, and a part of the photoelectric conversion film 12 sandwiched therebetween. This photoelectric conversion element is hereinafter referred to as a G photoelectric conversion element.

A photoelectric conversion element corresponding to the color filter 13b is formed by the transparent electrode 11b, the opposing upper electrode 13, and a part of the photoelectric conversion film 12 sandwiched therebetween. This photoelectric conversion element is hereinafter referred to as a B photoelectric conversion element.

In the n region inside of the p-well layer 2, a high-concentration n-type impurity region (hereinafter referred to as an "n+ region") 4r for accumulating electric charges generated in the photoelectric conversion film 12 of the on-substrate R photoelectric conversion element is formed. Incidentally, a light-shielding film is preferably provided on the n+ region 4r for preventing light from entering the n+ region 4r.

In the n region inside of the p-well layer 2, an n+ region 4g for accumulating electric charges generated in the photoelectric conversion film 12 of the on-substrate G photoelectric conversion element is formed. Incidentally, a light-shielding film is preferably provided on the n+ region 4g for preventing light from entering the n+ region 4g.

In the n region inside of the p-well layer 2, an n+ region 4b for accumulating electric charges generated in the photoelectric conversion film 12 of the on-substrate B photoelectric conversion element is formed. Incidentally, a light-shielding film is preferably provided on the n+ region 4b for preventing light from entering the n+ region 4b.

A contact part 6r comprising a metal such as aluminum is formed on the n+ region 4r, the transparent electrode 11r is formed on the contact part 6r, and the n+ region 4r and the transparent electrode 11r are electrically connected by the contact part 6r. The contact part 6r is embedded in an insulating layer 5 transparent to visible light and infrared light.

A contact part 6g comprising a metal such as aluminum is formed on the n+ region 4g, the transparent electrode 11g is formed on the contact part 6g, and the n+ region 4g and the transparent electrode 11g are electrically connected by the contact part 6g. The contact part 6g is embedded in the insulating layer 5.

A contact part 6b comprising a metal such as aluminum is formed on the n+ region 4b, the transparent electrode 11b is formed on the contact part 6b, and the n+ region 4b and the transparent electrode 11b are electrically connected by the contact part 6b. The contact part 6b is embedded in the insulating layer 5.

Inside of the p-well layer 2, in the region other than those where the n+ regions 4r, 4g and 4b are formed, a signal readout part 5r for reading out signals in proportion to electric charges generated in the R photoelectric conversion element and accumulated in the n+ region 4r, a signal readout part 5g for reading out signals in proportion to electric charges generated in the G photoelectric conversion element and accumulated in the n+ region 4g, and a signal readout part 5b for reading out signals in proportion to electric charges generated in the B photoelectric conversion element and accumulated in the n+ region 4b are formed. For each of the signal readout parts 5r, 5g and 5b, a known construction using a CCD or MOS circuit may be employed. Incidentally, a light-shielding film is preferably provided on the signal readout parts 5r, 5g and 5b for preventing light from entering the signal readout parts 5r, 5g and 5b.

Figure 19:
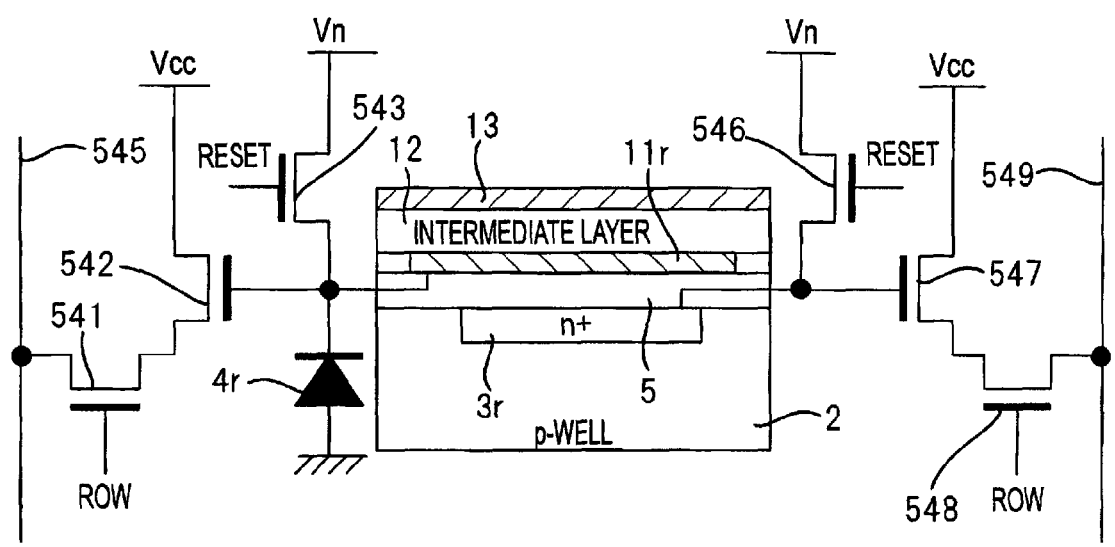
FIG. 19 is a view showing a specific construction example of the signal readout part shown in FIG. 18.

FIG. 19 is a view showing a specific construction example of the signal readout part 5r shown in FIG. 18. In FIG. 19, the same constituents as those in FIGS. 17 and 18 are indicated by like numerical references. Incidentally, the signal readout parts 5r, 5g and 5b have the same construction and the description of the signal readout parts 5g and 5b is omitted.

The signal readout part 5r comprises a reset transistor 543 with a drain being connected to the n+ region 4r and a source being connected to a power source Vn, an output transistor 542 with a gate being connected to the drain of the reset transistor 543 and a source being connected to a power source Vcc, a row selection transistor 541 with a source being connected to the drain of the output transistor 542 and a drain being connected to a signal output line 545, a reset transistor 546 with a drain being connected to the n region 3r and a source being connected to a power source Vn, an output transistor 547 with a gate being connected to the drain of the reset transistor 546 and a source being connected to a power source Vcc, and a row selection transistor 548 with a source being connected to the drain of the output transistor 547 and a drain being connected to a signal output line 549.

When a bias voltage is applied between the transparent electrode 11r and the upper electrode 13, an electric charge is generated in proportion to light incident into the photoelectric conversion film 12 and this electric charge is transported to the n+ region 4r through the transparent electrode 11r. Electric charges accumulated in the n+ region 4r are converted by the output transistor 542 into signals in proportion to the electric charge amount. Then, the row selection transistor 541 is turned ON, whereby the signals are output to the signal output line 545. After the output of signals, the electric charge inside of the n+ region 4r is reset by the reset transistor 543.

In this way, the signal readout part 5r can be constructed by a known MOS circuit comprising three transistors.

Backing to FIG. 18, protective layers 15 and 16 constituting a two-layer structure for protecting the photoelectric conversion elements on the substrate are formed on the photoelectric conversion film 12, and color filters 13r, 13g and 13b are formed on the protective layer 16.

This image device 100 is produced by forming the photoelectric conversion film 12 and then forming the color filters 13r, 13g and 13b and the like, but the formation of color filters 13r, 13g and 13b involves a photolithography step and in the case of using an organic material as the photoelectric conversion film 12, when the photolithography step or baking step is performed in the state of the photoelectric conversion film 12 being exposed, this causes deterioration in the properties of the photoelectric conversion film 12. In the image device 100, the protective films 15 and 16 are provided for preventing the properties of the photoelectric conversion film 12 from deterioration ascribable to such a production process.

The protective layer 15 is preferably an inorganic layer comprising an inorganic material and being formed by an ALCVD method. The ALCVD method is an atomic layer CVD method and enables the formation of a dense inorganic layer, and the layer formed can work out to an effective protective layer of the photoelectric conversion layer 9. The ALCVD method is also known as an ALE method or an ALD method. The inorganic layer formed by the ALCVD method preferably comprises $Al_2O_3$, $SiO_2$, $TiO_2$, $ZrO_2$, MgO, $HfO_2$ or $Ta_2O_5$, more preferably $Al_2O_3$ or $SiO_2$, and most preferably $Al_2O_3$.

The protective layer 16 is formed on the protective layer 15 for more enhancing the performance of protecting the photoelectric conversion film 12 and is preferably an organic layer comprising an organic polymer. The organic polymer is preferably parylene, more preferably parylene C. Incidentally, the protective layer 16 may be omitted, or the arrangement of the protective layer 15 and the protective layer 16 may be reversed. A high effect of protecting the photoelectric conversion film 12 is obtained particularly by the construction shown in FIG. 18.

When a predetermined bias voltage is applied to the transparent electrode 11r and the upper electrode 13, electric charges generated in the photoelectric conversion film 12 constituting the on-substrate R photoelectric conversion element are transported to the n+ region 4r through the transparent electrode 11r and the contact part 6r and accumulated in the region. Signals in proportion to electric charges accumulated in the n+ region 4r are read out by the signal readout part 5r and output outside of the image device 100.

Similarly, when a predetermined bias voltage is applied to the transparent electrode 11g and the upper electrode 13, electric charges generated in the photoelectric conversion film 12 constituting the on-substrate G photoelectric conversion element are transported to the n+ region 4g through the transparent electrode 11g and the contact part 6g and accumulated therein. Signals in proportion to electric charges accumulated in the n+ region 4g are read out by the signal readout part 5g and output outside of the image device 100.

Also, similarly, when a predetermined bias voltage is applied to the transparent electrode 11b and the upper electrode 13, electric charges generated in the photoelectric conversion film 12 constituting the on-substrate B photoelectric conversion element are transported to the n+ region 4b through the transparent electrode 11b and the contact part 6b and accumulated therein. Signals in proportion to electric charges accumulated in the n+ region 4b are read out by the signal readout part 5b and output outside of the image device 100.

In this way, the image device 100 can output, to the outside, signals of R component in proportion to electric charges generated in the R photoelectric conversion element, signals of G component in proportion to electric charges generated in the G photoelectric conversion element, and signals of B component in proportion to electric charges generated in the B photoelectric conversion element, whereby a color image can be obtained. This mode enables thinning the photoelectric conversion part, so that resolution can be enhanced and a false color can be reduced. Also, the opening ratio can be made large irrespective of the lower circuit and therefore, high sensitivity can be achieved. Furthermore, a microlens can be omitted and this is effective in reducing the number of components.

In this embodiment, the organic photoelectric conversion film needs to have a maximum absorption wavelength in the green light region and have an absorption region over the entire visible light, but this can be preferably realized by the materials specified above of the present invention.

EXAMPLES

The present invention is described in greater detail below by referring to Examples, but the present invention is of course not limited to these Examples.

Synthesis examples of the compounds for use in the present invention are described below.

[Synthesis of Compound 1]

First, 2.0 g of 4-hydroxycoumarin and 2.4 g of N,N'-diphenylformamidine were refluxed under heating for 7 hours in 20 ml of ethanol and after cooling to room temperature, the resulting solution was filtered and dried to obtain 2.55 g of Intermediate 1a. Then, 0.5 g of Intermediate 1a, 0.7 g of 1,2,3,3-tetramethylindolenium iodide and 0.32 ml of triethylamine were refluxed under heating for 6 hours in 10 ml of acetonitrile and after cooling to room temperature, the resulting solution was filtered and dried to obtain 0.5 g of Compound 1. This compound had absorption characteristics ($CHCl_3$) of λmax: 491 nm and ∈: 102,000 $Lmol^{-1}cm^{-1}$.

Intermediate 1a:

Intermediate 1a:

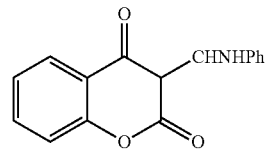

[Synthesis of Compound 3]

In the synthesis of Compound 1, 0.7 g of 1,2,3,3-tetramethylindolenium iodide was replaced by 0.7 g of 3-ethyl-2-methylbenzothiazolium iodide to obtain 0.68 g of Compound 3. This compound had absorption characteristics ($CHCl_3$) of λmax: 500 nm and ∈: 113,000 $Lmol^{-1}cm^{-1}$.

[Synthesis of Compound 6]

In the same manner as in the synthesis of Compound 1, 0.62 g of Compound 6 was obtained except for only replacing 0.7 g of 1,2,3,3-tetramethylindolenium iodide by 0.9 g of 3-ethyl-2-methylnaphth[2,3-d]oxazolium tosylate. This compound had absorption characteristics ($CHCl_3$) of λmax: 500 nm and ∈: 113,000 $Lmol^{-1}cm^{-1}$.

[Synthesis of Compound 8]

First, 3 g of 1-hydroxy-2-acetonaphthone and 20 ml of diethyl carbonate were added to a solution obtained by dispersing 2.3 g of sodium hydride in 30 ml of tetrahydrofuran, and the mixture was refluxed under heating for 5 hours, Then, 10 ml of methanol was added, and the system was further refluxed under heating for 1 hour. The resulting solution was cooled to room temperature and after pouring dilute hydrochloric acid, crystals obtained were filtered and dried to obtain Intermediate 8a. Subsequently, 2.5 g of Intermediate 8a and 2.5 g of N,N'-diphenylformamidine were refluxed under heating for 2 hours in 40 ml of ethanol, and the resulting solution was cooled to room temperature, filtered and dried to obtain 2.1 g of Intermediate 8b. Furthermore, 0.8 g of Intermediate 8b, 0.9 g of 3-ethyl-2-methylbenzothiazolium iodide and 0.42 ml were refluxed under heating for 4 hours in 10 ml of ethanol and after cooling to room temperature, the resulting solution was filtered and dried to obtain 1.0 g of Compound 8. This compound had absorption characteristics (CHCl$_3$) of λmax: 505 nm and ∈: 136,000 Lmol$^{-1}$cm$^{-1}$.

Intermediate 8b:

Intermediate 8b:

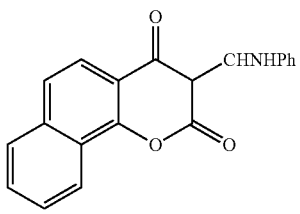

[Synthesis of Compound 9]

In the same manner as in the synthesis of Compound 8, 0.79 g of Compound 9 was obtained except for only replacing 0.9 g of 3-ethyl-2-methylbenzothiazolium iodide by 1.1 g of 3-ethyl-2-methylnaphth[2,3-d]oxazolium tosylate. This compound had characteristics (CHCl$_3$) of λmax: 479 nm and ∈: 167,000 Lmol$^{-1}$cm$^{-1}$.

According to Bull. Chem. Soc. Jpn., 56, 1775 (1983), the absorption characteristics (DMSO) of quinacridone as a comparative compound were λmax: 525 nm and ∈: 16,000 Lmol$^{-1}$cm$^{-1}$.

Example 1

With the configuration of FIG. 12, amorphous ITO of 30 nm was film-formed on a CMOS substrate by sputtering, and a pixel electrode 11 was formed through patterning by photolithography such that one pixel was present on each photodiode (PD) on the CMOS substrate. Thereon, m-MTDATA of 100 nm as a subbing and electron-blocking layer, Compound 1 of 100 nm as a photoelectric conversion layer, Alq of 20 nm as a hole-blocking and buffering layer and SiO of 20 nm were film-formed each by vacuum heating vapor deposition to stack an intermediate layer 12. Furthermore, amorphous ITO was film-formed as an upper electrode to a thickness of 5 nm by sputtering to stack a transparent electrode 13, whereby a solid-state image device was produced. The vacuum vapor deposition of the intermediate layer 12 was performed at a vacuum degree of 4×10$^{-4}$ Pa or less for all layers.

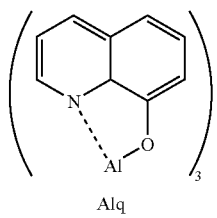

Alq

Example 2

A solid-state image device was produced in the same manner as in Example 1 except for changing Compound 1 in the photoelectric conversion film to Compound 3 and changing m-MTDATA to EB-3.

Example 3

A solid-state image device was produced in the same manner as in Example 2 except for changing Compound 3 in the photoelectric conversion film to Compound 6.

Example 4

A solid-state image device was produced in the same manner as in Example 1 except for changing Compound 1 in the photoelectric conversion film to Compound 6.

Example 5

A solid-state image device was produced in the same manner as in Example 2 except for changing Compound 3 in the photoelectric conversion film to Compound 8.

Example 6

A solid-state image device was produced in the same manner as in Example 1 except for changing Compound 1 in the photoelectric conversion film to Compound 9.

Comparative Example 1

A solid-state image device was produced in the same manner as in Example 2 except for changing Compound 3 in the photoelectric conversion film to quinacridone.

Comparative Example 2

A solid-state image device was produced in the same manner as in Example 2 except for changing Compound 3 in the photoelectric conversion film to Comparative Compound A shown below. Absorption characteristics (CHCl₃) of Comparative Compound A were λmax: 443 nm and ∈: 84,000 Lmol⁻¹ cm⁻¹.

Comparative Example A

Comparative Example A:

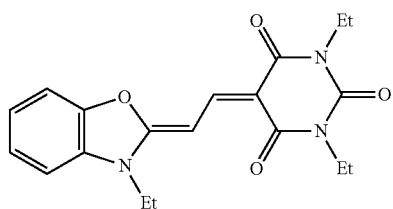

The external quantum efficiency at a wavelength of maximum sensitivity at a dark current of 1 nA/cm² and the relative response speed of each of the photoelectric conversion elements produced in Examples 1 to 6 and Comparative Examples 1 and 2 are shown in Table 1. Incidentally, when measuring the photoelectric conversion performance of each element, an appropriate voltage was applied.

TABLE 1

| | Compound Used for Light Absorption and Photoelectric Conversion | External Quantum Efficiency at Wavelength of Maximum Sensitivity at Dark Current of 1 nA/cm² (relative value) | Rising Time from 0 to 98% Signal Strength (relative value) |
|---|---|---|---|
| Example 1 | Compound 1 | 0.9 | 0.1 |
| Example 2 | Compound 3 | 1.7 | 0.1 |
| Example 3 | Compound 6 | 1.0 | 0.3 |
| Example 4 | Compound 6 | 1.1 | 0.2 |
| Example 5 | Compound 8 | 1.7 | 0.7 |
| Example 6 | Compound 9 | 1.5 | 0.6 |
| Comparative Example 1 | quinacridone | 1.0 | 1 |
| Comparative Example 2 | Comparative Compound A | 0.1 | — |

As seen from the absorption characteristic date in the form of a solution, the material of the present invention exhibits a high extinction coefficient (e) and is useful as a dye for photoelectric conversion elements in which signals are obtained in proportion to the light absorbed. This property is important from the standpoint that the light absorption amount can be ensured particularly even when formed as a thin layer. It is seen from Table 1 that by using the photoelectric conversion film-containing image device of the present invention, imaging can be performed at a high response speed and a high S/N.

According to the present invention, an organic semiconductor composed of a novel thin film, a photoelectric conversion element using the organic semiconductor and exhibiting high photoelectric conversion efficiency, low dark current and high-speed response, a solid-state image device containing the photoelectric conversion element, and a compound useful for the organic semiconductor can be obtained.

The entire disclosure of each and every foreign patent application from which the benefit of foreign priority has been claimed in the present application is incorporated herein by reference, as if fully set forth.

What is claimed is:

1. A photoelectric conversion element, comprising:

a photoelectric conversion part that contains:

a first electrode and a second electrode; and a non-polymeric organic photoelectric conversion film disposed between the first and second electrodes, wherein the organic photoelectric conversion film contains an organic semiconductor comprising a compound represented by formula (I):

Formula (I):

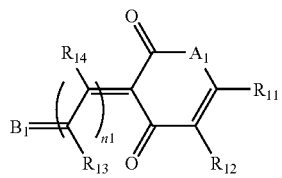

wherein $A_1$ represents O, S or N—$R_{15}$;

each of $R_{11}$, $R_{12}$, $R_{13}$, $R_{14}$ and $R_{15}$ independently represents a hydrogen atom or a substituent W selected from the group consisting of a halogen atom, an alkyl group, an alkenyl group, an alkynyl group, an aryl group, a heterocyclic group, a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group, an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boronic acid group, a phosphato group and a sulfato group, $R_{11}$ and $R_{12}$ may be linked to form a ring;

$B_1$ represents a ring structure containing at least one nitrogen atom; and n1 represents an integer of 0 to 2.

2. The photoelectric conversion element according to claim 1, wherein one of the first and second electrodes is an electrode on a light incident side, and the electrode on the light incident side is a transparent electrode.

3. The photoelectric conversion element according to claim 2, wherein the transparent electrode contains a transparent electrically conductive oxide.

4. The photoelectric conversion element according to claim 1, further comprising:

a hole-blocking layer between the organic photoelectric conversion film and at least one of the first and second electrodes.

5. The photoelectric conversion element according to claim 1, further comprising:
   an electron-blocking layer between the organic photoelectric conversion film and at least one of the first and second electrodes.

6. The photoelectric conversion element according to claim 1, further comprising:
   a semiconductor substrate in which at least one of the photoelectric conversion part is stacked on an upper side of the semiconductor substrate;
   an electric charge accumulating part formed inside of the semiconductor substrate, the electric charge accumulating part accumulating electric charges generated in the organic photoelectric conversion film contained in the photoelectric conversion part; and
   a connection part that electrically connects one of the first and second electrodes for collecting the electric charges to the electric charge accumulating part.

7. A solid-state image device, comprising:
   a plurality of the photoelectric conversion elements according to claim 6 disposed in an array manner; and
   a plurality of signal readout parts, each of the plurality of signal readout parts reading out signals in proportion to the electric charges accumulated in a respective one of the electric charge accumulating parts of the plurality of the photoelectric conversion elements.

8. An image device, comprising:
   the photoelectric conversion element according to claim 1.

* * * * *